United States Patent [19]
Scott

[11] Patent Number: 5,171,739
[45] Date of Patent: * Dec. 15, 1992

[54] TREATMENT OF ENDOTOXIN-ASSOCIATED SHOCK AND PREVENTATION THEREOF USING A BPI PROTEIN

[75] Inventor: Randal W. Scott, Cupertino, Marian N. Marra, San Mateo, all of Calif.

[73] Assignee: Incyte Pharmaceuticals, Inc., Redwood City, Calif.

[*] Notice: The portion of the term of this patent subsequent to Feb. 18, 2009 has been disclaimed.

[21] Appl. No.: 681,551

[22] Filed: Apr. 5, 1991

Related U.S. Application Data

[63] Continuation-in-part of Ser. No. 567,016, Aug. 13, 1990, which is a continuation-in-part of Ser. No. 468,696, Jan. 22, 1990, Pat. No. 5,089,274, which is a continuation-in-part of Ser. No. 310,842, Feb. 14, 1989, abandoned.

[51] Int. Cl.⁵ .............................................. A61K 37/02
[52] U.S. Cl. ...................................... 514/12; 514/921
[58] Field of Search ........................................... 514/12

[56] References Cited

U.S. PATENT DOCUMENTS 84,335  8/1987  Elsbach .

FOREIGN PATENT DOCUMENTS 0272489    6/1988   European Pat. Off. .
WO/8802700 8/1988   World Int. Prop. O. .
WO/9000837 2/1990   World Int. Prop. O. .

OTHER PUBLICATIONS

M. N. Marra, et al., (1990) J. Immunol., 144:662–666, (Exhibit A).
P. Elsbach, et al., (1988) Bacteria–Host Cell Interaction, pp. 47∝60 (Exhibit B).
P. Gray et al., (1988) Clinical Research, 36(3):620A (Exhibit C).
P. Gray et al., (1989) The Journal of Biological Chemistry 264(16):9505 (Exhibit D).
J. Weiss et al., (1982) The American Society of Clinical Investigation, Inc. 69:959 (Exhibit F).
J. Weiss et al., (1985) The American Society of Clinical Investigation, Inc., 76:206 (Exhibit G).
S. Leong, et al., J. Cell Biochem. Suppl. 13:66 (1989) (Exhibit J).
J. Weiss, et al., Infection and Immunity, 38:1149–1153 (1982) (Exhibit K).
K. Muello, et al., Clinical Research, 31:371A (Exhibit L).
J. Weiss et al., J. Clin. Invest., 71:540–549 (1983) (Ex. M).
W. M. Shafer, et al., Infection and Immunity, 45:29–35 (1984) (Exhibit N).
C. J. Hovde, et al., Infection and Immunity, 54:142–148 (1986) (Exhibit O).
J. Weiss, et al., Infection and Immunity, 51:594–599 (1986) (Exhibit P).
J. K. Spitznagel, et al., J. Immunol. 139:1291–1296 (1987) (Exhibit Q).
M. M. Shafer, et al., Infection and Immunity, 55:1536–1539 (1987) (Exhibit R).
G. I. Veld, et al., Infection and Immunity, 56:1203–1208 (1988) (Exhibit S).
M. M. Farley, et al., Infection and Immunity, 56:1589–1592 (1988) (Exhibit T).
B. A. Mannion et al., J. Immunol. 142:2807–2812 (1989) (Ex U).
J. Weiss et al., (1985) ASCI Metabolism, 33(2):567(A) (Ex. V).
B. A. Mannion et al., J. Cin. Invest. 85:853–860 (1990) (Exhibit W).
A. H. Pereira, et al., Blood 76:825–834 (1990) (Exhibit X).
R. R. Schumann, et al., Science 249:1429–1431 (1990) (Exhibit Y); and.

Primary Examiner—Merrell C. Cashion, Jr.
Assistant Examiner—Choon P. Koh
Attorney, Agent, or Firm—John P. White

[57] ABSTRACT

The present invention provides a method for preventing endotoxin-associated shock in a subject which comprises administering to the subject an amount of a BPI protein effective to bind to endotoxin so as to prevent endotoxin associated shock in the subject. This invention further provides a method for treating a subject suffering from endotoxin-associated shock which comprises administering to the subject an amount of a BPI protein effective to bind endotoxin so as to treat the subject suffering from endotoxin-associated shock.

6 Claims, 51 Drawing Sheets

LPS STIMULATION OF GRANULOCYTES CR1

NEUTRILIZATION OF LPS BY CRUDE AZUROPHIL EXTRACT

LPS INHIBITION BY RPLC PURIFIED AZUROPHIL GRANULE EXTRACT

FIGURE 3A₁
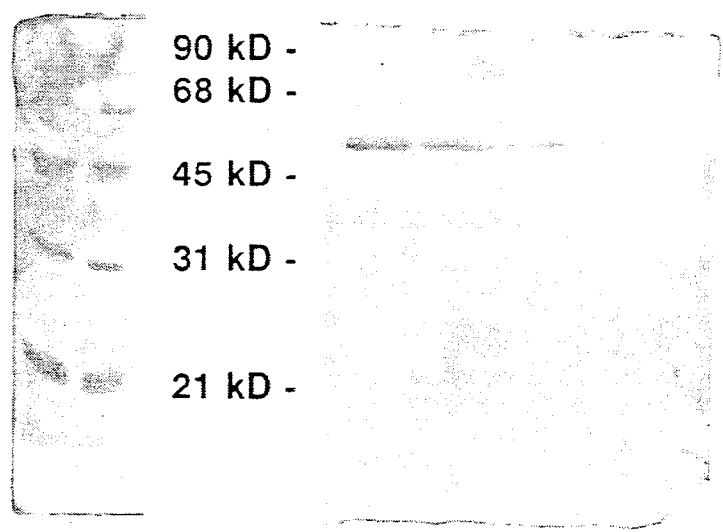

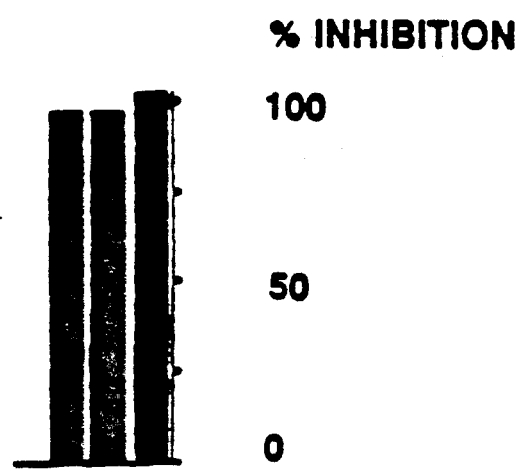
Figure 3A$_2$

LPS INHIBITORY ACTIVITY OF 3X PURIFIED BPI

O.D. 214 nm

FRACTION NUMBER

DOSE RESPONSE OF BPI VS 10 NG/ML 0111:B4 LPS

% INHIBITION

BPI (NG/ML)

LPS NEUTRALIZATION BY POLYMIXIN B

CR3 EXPRESSION ON STIMULATED NEUTROPHILS

TIMECOURSE OF LPS INHIBITION BY BPI AND POLYMYXIN B

BPI BINDS TO LPS IN THE PRESENCE OF SERUM

Data from "LPS BINDING 6.4"

Linear scale of ng/ml

Figure 25

BPI MUTAGENIC PRIMERS

C-TERMINAL TRUNCATION OF BPI

25KD Pro 212 TGA

```
AA.  205                        210       212
     Ile  Asn  Tyr  Gly  Leu  Val  Ala  Pro  Ter.Bam HI

TAG  AAC  TAT  GGT  CTG  GTG  GCA  CCT  TGA  GGATCCGCG

COMP
        3'   ATA  CCA  GAC  CAC  CGT  GGA  ACT  CCTAGGCGC 5'

OLIGO 459:
     5' CGCGGATCC    TCA  AGG  TGC  CAC  CAG  ACC  ATA  3'
```

Figure 26

BPI MUTAGENIC PRIMERS

C-TERMINAL TRUNCATION OF BPI

38KD Pro 337 TGA

```
AA.  330                      335        337
     Pro Thr Gly Leu Thr Phe Tyr Pro Ter    Bam HI
     CCC ACC GGC CTT ACC TTC TAC CCT TGA GGATCCGCG

COMP:
         3' CCG     GAA TGG AAG ATG GGA ACT CCTAGGCGC 5'

OLIGO 460:
      5'   CGCGGATCC   TCA AGG GTA GAA GGT AAG GCC   3'
```

Figure 27

BPI MUTAGENIC PRIMERS

C-TERMINAL TRUNCATION OF BPI

PREFERED ATG 5'HIND III:

AA.      -31                  -26
    HINd III    Start     Met  Arg  Glu  Asn  Met  Arg
    CCCAAGCTT  GCC ACC  ATG  AGA  GAG  AAC  ATG  GCC

OLIGO 458:
5' CCCAAGCTT GCC ACC ATG AGA GAG AAC ATG GCC 3'

No sites for: SmaI, PstI, BglII, XbaI, SstI

The nucleotide sequence presented above was determined by V.A. Luckow.

Figure 31A

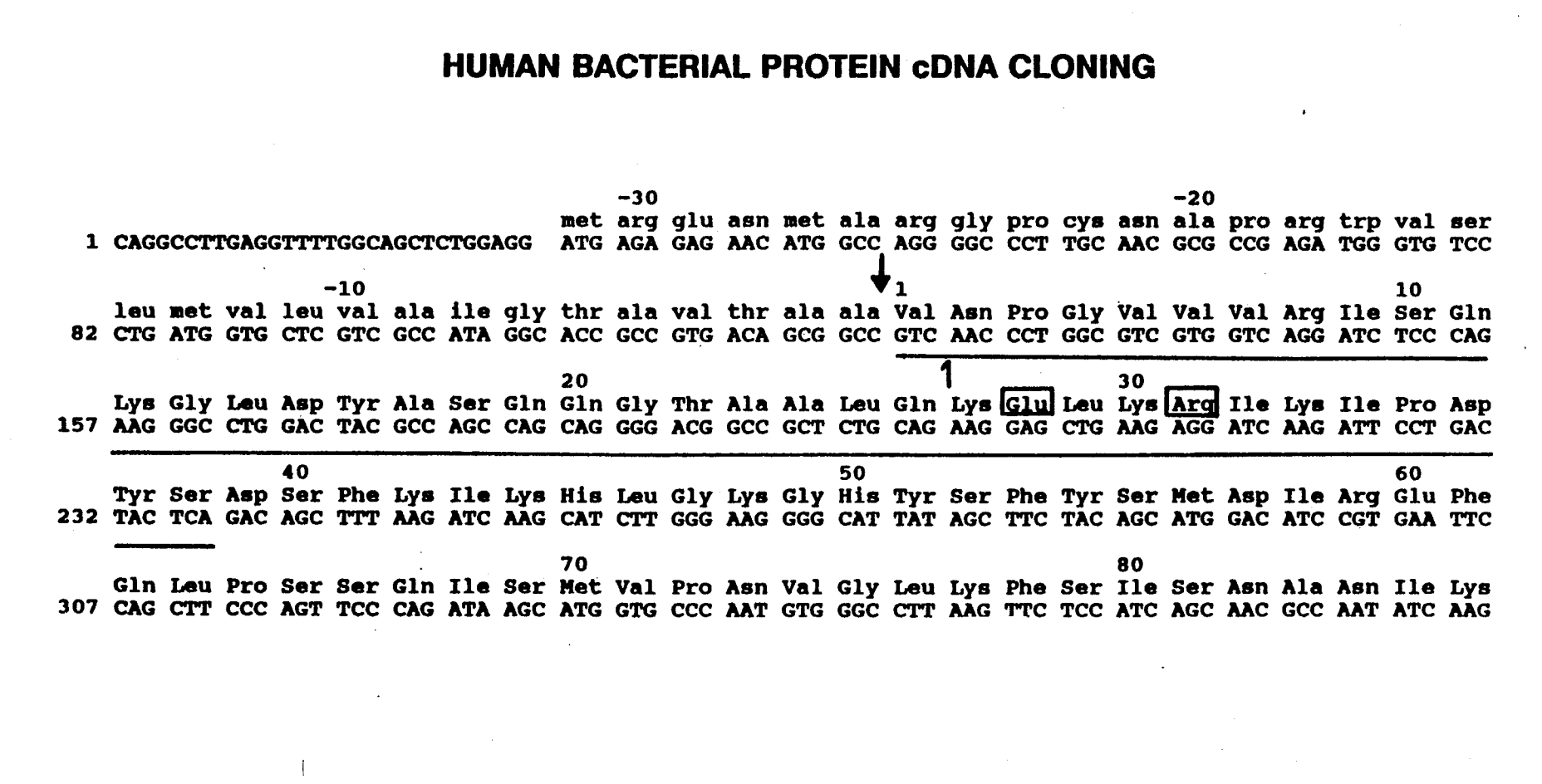

HUMAN BACTERIAL PROTEIN cDNA CLONING

```
                                                        -30
                                          met arg glu asn met ala arg gly pro cys asn ala
  1 CAGGCCTTGAGGTTTGGCAGCTCTGGAGG          ATG AGA GAG AAC ATG GCC AGG GGC CCT TGC AAC GCG
                                                                              -20
    leu met val leu val ala ile gly thr ala val thr ala ala val asn pro gly val val arg ile ser gln
                   -10                                          ↓1                                10
 82 CTG ATG GTG CTC GTC GCC ATA GGC ACC GCC GTG ACA GCG GCC GTC AAC CCT GGC GTC GTG AGG ATC TCC CAG lys gly leu asp tyr ala ser gln gly thr ala ala leu gln lys gln lys leu[glu]leu lys[arg]ile lys pro asp
                              20                                        30
157 AAG GGC CTG GAC TAC GCC AGC CAG GGC ACG GCC GCT CTG CAG AAG CAG AAG CTG GAG CTG AAG AGG ATC AAG CCT GAC tyr ser asp ser phe lys ile lys his leu gly lys gly tyr his leu tyr ser phe tyr ser met asp ile arg glu phe
                      40                                        50                                60
232 TAC TCA GAC AGC TTT AAG ATC AAG CAT CTT GGG AAG GGG CAT TTA TAC AGC TTC TAC AGC ATG GAC ATC CGT GAA TTC gln leu pro ser ser gln ile ser gln ile ser met val pro asn val gly leu lys phe ser ile ser asn ala asn ile lys
                              70                                        80
307 CAG CTT CCC AGT TCC CAG ATA TCC CAG ATA AGC ATG GTG CCC AAT GTG GGC CTT AAG TTC TCC ATC AGC AAC GCC AAT ATC AAG
```

Figure 31B

```
      Ile Ser Gly Lys Trp Lys Ala Gln Lys Arg Phe Leu Lys Met Ser Gly Asn Phe Asp Leu Ser Ile Glu Gly Met
              90                                 100                                110
382   ATC AGC GGG AAA TGG AAG GCA CAA AAG AGA TTC TTA AAA ATG AGC GGC AAT TTT GAC CTG AGC ATA GAA GGC ATG

Ser Ile Ser Ala Asp Leu Lys Leu Gly Ser Asn Pro Thr Ser Gly Lys Pro Thr Ile Thr Cys Ser Ser Cys Ser
                             120                                 130
457   TCC ATT TCG GCT GAT CTG AAG CTG GGC AGT AAC CCC ACG TCA GGC AAG CCC ACC ATC ACC TGC AGC TCC AGC

Ser His Ile Asn Ser Val His Val Gly Ser Lys Val Ser Lys Leu Ile Gln Leu Phe His Lys Lys
              140                                150
532   AGC CAC ATC AAC AGT GTC CAC GTG GGC AGC AAG GTC AAA AGC CTG ATC CAA CTC TTC CAC AAA AAA

Ile Glu Ser Ala Leu Arg Asn Lys Met Asn Ser Gln Val Cys Glu Lys Val Thr Asn Ser Val Ser Lys Leu
                     170                                180
607   ATT GAG TCT GCG CTT CGA AAC AAG ATG AAC AGC CAG GTC TGC GAG AAA GTG ACC AAT TCT GTA TCC AAG CTG

Gln Pro Tyr Phe Gln Thr Leu Pro Val Met Thr Lys Ile Asp Ser Val Ala Gly Ile Asn Tyr Gly Leu Val Ala
              190                                200                                210
682   CAA CCT TAT TTC CAG ACT CTG CCA GTA ATG ACC AAA ATA GAT TCT GTG GCT GGA ATC AAC TAT GGT CTG GTG GCA

Pro Pro Ala Thr Thr Ala Glu Thr Leu Asp Val Gln Met Lys Gly Glu Phe Tyr Ser Glu Asn His His Asn Pro
                             220                                230
757   CCT CCA GCA ACC ACG GCT GAG ACC CTG GAT GTA CAG ATG AAG GGG GAG TTT TAC AGT GAG AAC CAC CAC AAT CCA
```

Figure 31C

|     |     | 240 |     |     |     |     |     |     |     | 250 |     |     |     |     |     |     |     |     | 260 |     |     |
| --- | --- | --- | --- | --- | --- | --- | --- | --- | --- | --- | --- | --- | --- | --- | --- | --- | --- | --- | --- | --- | --- |
|     | Pro | Pro | Phe | Ala | Pro | Pro | Val | Met | Glu | Phe | Pro | Ala | Ala | His | Asp | Arg | Met | Val | Tyr | Leu | Gly | Leu | Ser | Asp | Tyr |
| 832 | CCT | CCC | TTT | GCT | CCA | CCA | GTG | ATG | GAG | TTT | CCC | GCT | GCC | CAT | GAC | CGC | ATG | GTA | TAC | CTG | GGC | CTC | TCA | GAC | TAC |

|     |     |     |     |     |     | 270 |     |     |     |     |     |     |     |     |     | 280 |     |     |     |     |
| --- | --- | --- | --- | --- | --- | --- | --- | --- | --- | --- | --- | --- | --- | --- | --- | --- | --- | --- | --- | --- |
|     | Phe | Phe | Asn | Thr | Ala | Gly | Leu | Val | Tyr | Gln | Glu | Ala | Gly | Val | Leu | Lys | Met | thr | Leu | Arg | Asp | Asp | Met | Ile | Pro |
| 907 | TTC | TTC | AAC | ACA | GCC | GGG | CTT | GTA | TAC | CAA | GAG | GCT | GGG | GTC | TTG | AAG | ATG | ACC | CTT | AGA | GAT | GAC | ATG | ATT | CCA |

|     |     | 290 |     |     |     |     |     |     |     | 300 |     |     |     |     |     |     |     |     | 310 |     |
| --- | --- | --- | --- | --- | --- | --- | --- | --- | --- | --- | --- | --- | --- | --- | --- | --- | --- | --- | --- | --- |
|     | Lys | Glu | Ser | Lys | Phe | Arg | Leu | Thr | Thr | Lys | Phe | Phe | Gly | Thr | Phe | Leu | Pro | Glu | Val | Ala | Lys | Lys | Phe | Pro | Asn |
| 982 | AAG | GAG | TCC | AAA | TTT | CGA | CTG | ACA | ACC | AAG | TTC | TTT | GGA | ACC | TTC | CTA | CCT | GAG | GTG | GCC | AAG | AAG | TTT | CCC | AAC |

|     |     |     |     |     |     | 320 |     |     |     |     |     |     |     |     |     | 330 |     |     |     |     |
| --- | --- | --- | --- | --- | --- | --- | --- | --- | --- | --- | --- | --- | --- | --- | --- | --- | --- | --- | --- | --- |
|      | Met | Lys | Ile | Gln | Ile | His | Val | Ser | Ala | Ser | Thr | Pro | Pro | His | Leu | Ser | Val | Gln | Pro | Thr | Gly | Leu | Thr | Phe | Tyr |
| 1057 | ATG | AAG | ATA | CAG | ATC | CAT | GTC | TCA | GCC | TCC | ACC | CCG | CCA | CAC | CTG | TCT | GTG | CAG | CCC | ACC | GGC | CTT | ACC | TTC | TAC |

|      | 340 |     |     |     |     |     |     |     |     | 350 |     |     |     |     |     |     |     |     | 360 |     |
| ---  | --- | --- | --- | --- | --- | --- | --- | --- | --- | --- | --- | --- | --- | --- | --- | --- | --- | --- | --- | --- |
|      | Pro | Ala | Val | Asp | Val | Gln | Ala | Phe | Ala | Val | Leu | Pro | Ser | Ser | Asn | Leu | Ala | Ser | Leu | Phe | Leu | Ile | Gly | Met | His |
| 1132 | CCT | GCC | GTG | GAT | GTC | CAG | GCC | TTT | GCC | GTC | CTC | CCC | TCC | TCC | AAC | CTG | GCT | TCC | CTC | TTC | CTG | ATT | GGC | ATG | CAC |

Figure 31D

```
     Thr Thr Gly Ser Met Glu Val Ser Ala Glu Ser Asn Arg Leu Val Gly Glu Leu Lys Leu Asp Arg Leu Leu
1207 ACA ACT GGT TCC ATG GAG GTC AGC GCC GAG TCC AAC AGG CTT GTT GGA GAG CTC AAG GAT AGG CTG CTC CTG
                                             370                                 380                              410
     Glu Leu Lys His Ser Asn Ile Gly Pro Phe Pro Val Glu Leu Leu Gln Asp Ile Met Asn Tyr Ile Val Pro Ile
1282 GAA CTG AAG CAC TCA AAT ATT GGC CCC TTC CCG GTT GAA TTG CTG CAG GAT ATC ATG AAC TAC ATT GTA CCC ATT
                    390                              400

Leu Val Leu Pro Arg Val Asn Glu Lys Leu Gln Lys Gly Phe Pro Leu Pro Thr Pro Ala Arg Val Gln Leu Tyr
1357 CTT GTG CTG CCC AGG GTT AAC GAG AAA CTA CAG AAA GGC TTC CCT CTC CCG ACG CCG GCC AGA GTC CAG CTC TAC
                         420                                 430                                 460

Asn Val Val Leu Gln Pro His Gln Asn Phe Leu Leu Phe Gly Ala Asp Val Val Tyr Lys
1432 AAC GTA GTG CTT CAG CCT CAC CAG AAC TTC CTG CTG TTC GGT GCA GAC GTT GTC TAT AAA TGA AGGCACCAGGGGTGCC
                    440                                 450

1511 GGGGGCTGTCAGCCGCACCTGTCCTGATGGGCTGTGGGCACCGCTGCCTTCCCCAGGAATCCTCTCCAGATCTTAACCAAGAGCCCCTTGCAAAC

1611 TTCTTCGACTCAGATTCAGAAATGATCTAAACACGAGGAAACATTATTCATTGGAAAAGTGCATGGTGTATTTTAGGGATTATGAGCTTCTTCAAGG

1711 GCTAAGGCTGCAGAGATATTTCCTCCAGAATCGTGTTTCAATTGTAACCAGAAATTTCATTGTGCTTCATGAAAAAAAACTTCTGGTTTTTTCAT

1811 GTG---poly-A tail
```

BPI Serum Half-Life

TREATMENT OF ENDOTOXIN-ASSOCIATED SHOCK AND PREVENTATION THEREOF USING A BPI PROTEIN

This application is a continuation-in-part of U.S. Ser. No. 567,016, filed Aug. 13, 1990, which is a continuation-in-part of U.S. Ser. No. 468,696, filed Jan. 22, 1990, U.S. Pat. No. 5,089,274, which is a continuation-in-part of U.S. application Ser. No. 310,842 filed Feb. 14, 1989, abandoned, the contents of all of which are hereby incorporated by reference.

BACKGROUND OF THE INVENTION

Gram negative infections are a major cause of morbidity and mortality especially in hospitalized and immunocompromised patients. [Duma, R. J., Am. J. of Med., 78 (Suppl. 6A): 154–164 (1985); and Kreger B. E., D. E. Craven and W. R. McCabe, Am. J. Med., 68: 344–355 (1980)] Antibiotics are presently being used to contain infections.

LPS is a major component of the outer membrane of gram negative bacteria and is released when the organisms are lysed. [Shenep, J. L. and K. A. Morgan, J. Infect. Dis., 150 (3): 380–388 (1984)] Although available antibiotics are generally effective in containing the infection, they do nothing to neutralize the pathophysiological effects associated with lipopolysaccharide (LPS).

LPS released during antibiotic therapy is a potent stimulator of the inflammatory response. Many detrimental effects of LPS in vivo result from soluble mediators released by inflammatory cells. [Morrison D. C. and R. J. Ulevich, Am. J. Pathol., 93 (2): 527–617 (1978)] LPS induces the release of mediators by host inflammatory cells which may ultimately result in disseminated intravascular coagulation (DIC), adult respiratory distress syndrome (ARDS), renal failure, and irreversible shock.

Soluble LPS causes decreased neutrophil chemotaxis, increased adhesiveness, elevated hexose monophosphate shunt activity and $O_2$ radical production, upregulation of surface receptors for complement, and release of granule proteins into the surrounding medium. [Morrison and Ulevich (1978)]

Endotoxemia is a condition associated with the presence of endotoxins, i.e. heat stable bacterial toxins, in the blood. Endotoxins elicit an inflammatory response that is beneficial in fighting the infection but can be damaging to the host if uncontrolled. Endotoxemia induces production of LPS binding proteins from the liver and causes release of microbicidal proteins from leukocytes. Our studies show that one of these leukocytes proteins (BPI) previously known only for its bactericidal activity in vitro, inhibits the ability of LPS to stimulate neutrophils and monocytes and reduces death due to endotoxin or bacterial challenge when given in vivo.

Monocytes and neutrophilic granulocytes play a key role in host defense against bacterial infections and also participate in the pathology of endotoxemia. These cells ingest and kill microorganisms intracellularly and also respond to LPS in vivo and in vitro by releasing soluble proteins with microbicidal, proteolytic, opsonic, pyrogenic, complement activating and tissue damaging effects.

Tumor necrosis factor (TNF), a cytokine released by LPS stimulated monocytes mimics some of the toxic effects of LPS in vivo. Injecting animals with TNF causes fever, shock and alterations in glucose metabolism. TNF is also a potent stimulator of neutrophils.

Despite improvements in antibiotic therapy, morbidity and mortality associated with endotoxemia remains high. Antibiotics alone are not effective in neutralizing the toxic effects of LPS. Therefore, the need arises for an adjunct therapy with direct LPS neutralizing activity. Current methods for treatment of endotoxemia use antibiotics and supportive care. Most available adjunct therapies treat symptoms of endotoxic shock such as low blood pressure and fever but do not inactivate endotoxin. Other therapies inhibit inflammatory host responses to LPS. As indicated below, present therapies have major limitations due to toxicity, immunogenicity, or irreproducible efficacy between animal models and human trials.

PMB is a basic polypeptide antibiotic which has been shown to bind to, and structurally disrupt, the most toxic and biologically active component of endotoxin, Lipid A. PMB has been shown to inhibit LPS activation of neutrophil granule release in vitro and is an effective treatment for gram negative sepsis in humans. However, because of its systemic toxicity, this drug has limited use except as a topical agent.

Combination therapy using antibiotics and high doses of methylprednisolone sodium succinate (MPSS) has been shown to prevent death in an experimental model of gram negative sepsis using dogs. Another study using MPSS with antibiotics in a multicenter, double blind, placebo-controlled, clinical study in 223 patients with clinical signs of systemic sepsis concluded that mortality was not significantly different between the treatment and placebo groups. Further, the investigators found that resolution of secondary infection within 14 days was significantly higher in the placebo group.

A relatively new approach to treatment of endotoxemia is passive immunization with endotoxin neutralizing antibodies. Hyperimmune human immunoglobulin against E. coli J5 has been shown to reduce mortality in patients with gram negative bacteremia and shock by 50%. Other groups have shown promising results in animal models using mouse, chimeric, and human monoclonal antibodies. Although monoclonal antibodies have advantages over hyperimmune sera, e.g. more consistent drug potency and decreased transmission of human pathogens, there are still many problems associated with administering immunoglobulin to neutralize LPS. Host responses to the immunoglobulins themselves can result in hypersensitivity. Tissue damage following complement activation and deposition of immune complexes is another concern in the use of therapies involving anti-endotoxin antibodies in septic patients.

BPI was first discovered in 1975 [Weiss, J., R. C. Franson, S. Becherdite, K. Schmeidler, and P. Elsbach, J. Clin. Invest., 55:33 (1975)] and was first obtained in highly purified form from human neutrophils in 1978 and shown to be bactericidal against gram negative bacteria when assayed in phosphate buffered saline in vitro [Weiss, J., P. Elsbach, I. Olson and H. Odeberg, J. Biol. Chem., 253 (8): 2664–2672 (1978)]. The mechanism of bacterial killing was not defined but proposed to be mediated through changes in membrane permeability (thus the name bactericidal/permeability increasing protein). However, BPI is inhibited by Mg, Ca, heparin [Weiss et al. J. Biol. Chem., 253 (8): 2664–2672 (1978)], and serum albumin [Mannion et al. J. Clin. Invest. 85:

853-860 (1990)] suggesting that it is not bactericidal in vivo. Weiss et al. [J. Biol. Chem. 254 (21): 11010-11014 (1979)], further showed that BPI increased phospholipase A2 activity suggesting a proinflammatory activity for BPI in addition to its supposed bactericidal activity.

Rabbit BPI was purified in 1979 [Elsbach et al. J. Biol. Chem. 254 (21): 11000-11009] and shown to have identical bactericidal and permeability increasing properties as human BPI providing a further source of material for study. Both rabbit and human BPI were shown to be effective against a variety of gram negative bacteria in vitro, including K1-encapsulated *E. coli* [Weiss et al. Infection and Immunity 38 (3): 1149-1153, (1982)].

A role for lipopolysaccharide in the in vitro bactericidal action of BPI was proposed in 1984 by Weiss et al. [J. Immunol. 132 (6): 3109-3115, (1984)] who demonstrated that BPI bound to the outer membrane of gram-negative bacteria and caused extracellular release of LPS and selectively stimulated biosynthesis of LPS. In 1984 a 57 kD protein with similar properties was isolated from human neutrophils and designated CAP 57 [Shafer, W. M., C. E. Martin and J. K. Spitznagel, Infect. Immun., 45:29 (1984)] This protein is identical to BPI protein as determined by the N-Terminal amino acid sequence, amino acid composition, molecular weight and source [Spitznagel et al Blood 76:825-834, 1990]. Another group, Hovde and Gray reported a 55kDa bactericidal glycoprotein with virtually identical properties to BPI in 1986 [Hovde and Gray Infection and Immunity 54(1): 142-148 (1986)].

BPI retains its in vitro bactericidal activity after cleavage of BPI with neutrophil proteases suggesting that fragments of the molecule retain activity [Ooi and Elsbach Clinical Research 33 (2):567A, (1985). All of the in vitro bactericidal and permeability increasing activities of BPI were later shown to be present in the N-terminal 25 kD fragment of the protein. [Ooi, C. E., J. Weiss, P. Elsbach, B. Frangione, and B. Marrion, J. Biol. Chem., 262: 14891 (1987)]

The fact that BPI is an LPS binding protein is evidenced by: (1) increased sensitivity of rough strains of permeability increasing activities of BPI [Weiss, J., M. Hutzler and L. Kao, Infect. Immun., 51:594 (1986)]; (2) mutations in the Lipid A domain of LPS caused decreased binding and increased resistance to bactericidal activity of both polymyxin B and BPI [Farley, M. M., W. M. Shafer and J. K. Spitznagel, Infect. Immun., 56:1536-1539 (1987) and Farley et al. Infect. Immun. 58:1589-1592 (1988)]; (3) BPI competed with polymyxin B (PMB) for binding to *S. typhimurium* [Farley 1988]; (4) BPI protein sequence homology and immunocrossreactivity to another LPS binding protein termed Lipopolysaccharide Binding Protein (LBP) [Tobias et al. J. Biol. Chem. 263 (27): 13479-13481 (1988). LBP-LPS complexes have been shown to stimulate the oxidative burst of neutrophils in response to formylated peptides [Vosbeck et al. Eur. J. Clin. Invest. 18 A50 (1988)]. In addition, LBP-LPS complexes bind back to a cell surface receptor on monocytes (CD 14) resulting in the induction of tumor necrosis factor (TNF) [Schumann et al. Science 249:1429-1431]. Thus LBP mediates the immunostimulatory activity of LPS and therefore stimulates the toxic response to endotoxin. BPI has exactly the opposite effects of LBP, binding to LPS and inhibiting neutrophil activation and blocking TNF production by monocytes.

BPI binding to gram negative bacteria was reported originally to disrupt LPS structure, alter microbial permeability to small hydrophobic molecules and cause cell death (Weiss, et al., 1978). More recently these same authors have demonstrated that such effects occur only in the absence of serum albumin. If bacteria are cultured in the presence of serum albumin BPI, in fact, has no bactericidal activity thus proving that BPI does not kill bacteria in vivo [Mannion et Clin. Invest. 85: 853-860 (1990) and Mannion et al. J. Clin. Invest. 86: 631-641)]. Therefore, prior to the subject invention, it has been understood in the art that the beneficial effects of BPI protein are limited to in vitro bactericidal effects. Here we show that BPI protein binds endotoxin in the presence of serum and plasma and, unlike other known LPS binding proteins such as LBP, BPI inhibits the immunostimulatory and toxic activities of LPS both in vitro and in vivo respectively. Thus BPI has a novel and distinct use in the therapeutic and prophylactic treatment of endotoxin-related disorders including endotoxemia and endotoxic shock.

Furthermore BPI is described by Gray et al. [J. Biol. Chem. 264 (16) 9505-9509 (1989)] as a membrane protein which must be cleaved to the 25 kDa fragment to be released from the neutrophil granule membrane in soluble form. The present invention provides for a method of producing full length soluble BPI in active form. Further the present invention separates for the first time two molecular forms of the molecule apparantly unresolved by Gray et al. representing glycosylated and nonglycosylated forms of the molecule which appear to have different serum half-life profiles in vivo and thus different therapeutic potential. Natural BPI from neutrophils is a mixture of the glycoslyated and nonglycosylated forms.

SUMMARY OF THE INVENTION

This invention provides a method for preventing endotoxin-associated shock in a subject which comprises administering to the subject an amount of a BPI protein effective to bind to endotoxin so as to prevent endotoxin associated shock in the subject.

The present invention further provides a method for treating a subject suffering from endotoxin-associated shock which comprises administering to the subject an amount of a BPI protein effective to bind endotoxin so as to treat the subject suffering from endotoxin-associated shock.

The present invention provides a composition comprising a BPI protein and an anionic compound which composition (1) exhibits no bactericidal activity and (2) inhibits endotoxin activity.

Additionally, the present invention provides a variant BPI protein which specifically binds to a lipid A binding site of LPS and competes with BPI protein for the lipid A binding site and which protein increases the L.D.50 of *E. coli* O11:B4 LPS in CD1 mice.

Further, this invention provides a recombinant BPI protein as shown in FIG. 31, which migrates as a single-band on a SDS gel at about 55,000 MW.

This invention additionally provides a method for producing and secreting full length soluble BPI protein from a cell which comprises (a) constructing a vector comprising DNA encoding BPI; (b) transfecting the cell with the vector; and (c) culturing the cell so transfected in culture medium under conditions such that full length soluble BPI protein is secreted.

After three washes, 100 μl of polyclonal rabbit anti-BPI protein IgG was added to the wells and incubated for 1 hour at 37 degrees centigrade. The wells were washed three times and developed with goat-anti-rabbit Ig alkaline phosphate conjugate, followed by three more washes and PNPP substrate (Sigma). Color development at 405 nm was monitored.

FIG. 20: Photographs of transformed plates of JM109(DE3) with the T7 promoter/BPI protein plasmid constructs. Photographs were taken with f8 at 1/125 second exposure.

A. pT7BPI-F (+) contains the full-length BPI protein sequence (including the signal sequence) placed in the correct orientation behind the T7 promoter for expression.

B. pT7BPI-F (−) contains the full-length BPI protein sequence (including the signal sequence) placed in the incorrect orientation behind the T7 promoter (resulting protein is a fusion protein with the 260 amino acid leader peptide of T7 gene 10).

C. pT7BPI-S contains the full-length BPI protein sequence (without the signal sequence) placed in the correct orientation behind the T7 promoter for expression.

D. pT7212-F contains the proline-212 truncated BPI protein sequence (including the signal sequence) placed in the correct orientation behind the T7 promoter for expression.

E. pT7212-S contains the proline-212 truncated BPI protein sequence (without the signal sequence) placed in the correct orientation behind the T7 promoter for expression.

Figure 21:
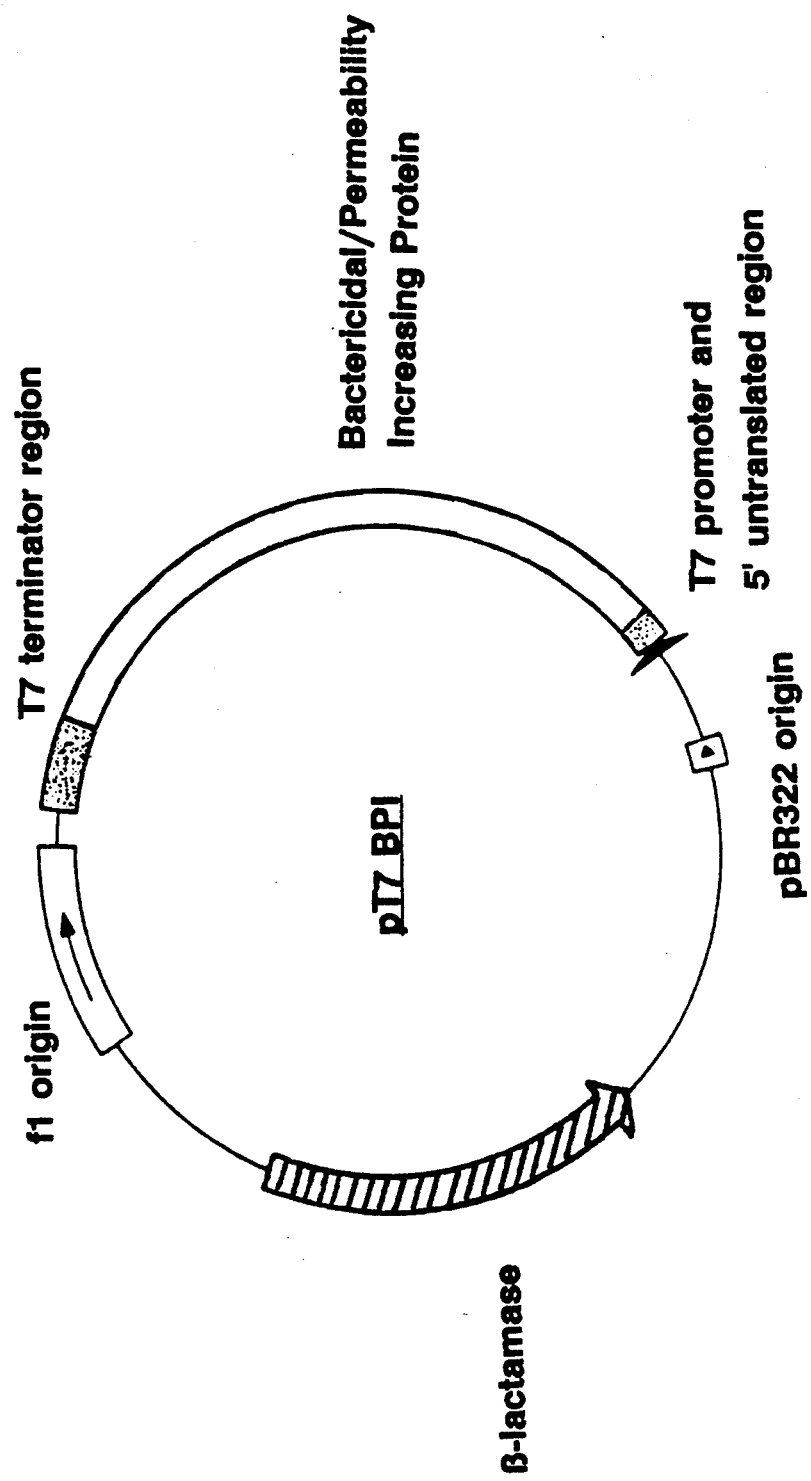

FIG. 21: Schematic of the pT7BPI protein plasmid construct.

Figure 22:
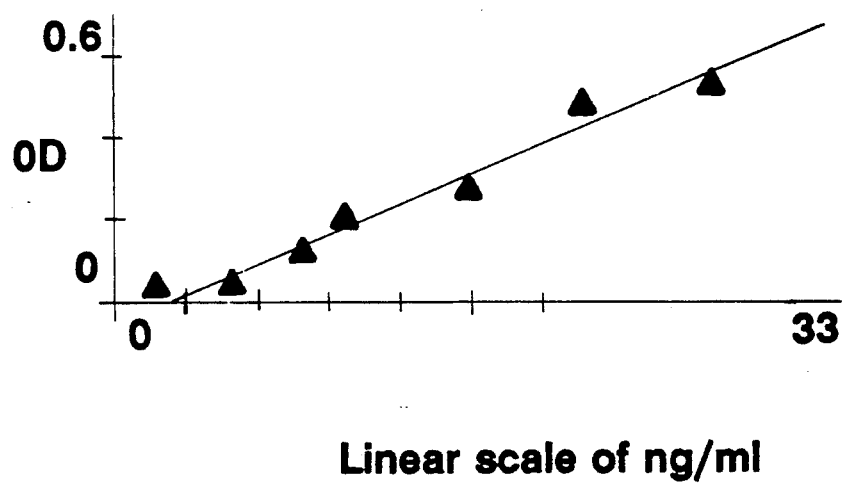

FIG. 22: Standard curve showing BPI protein activity in ELISA Assay.

Figure 23:
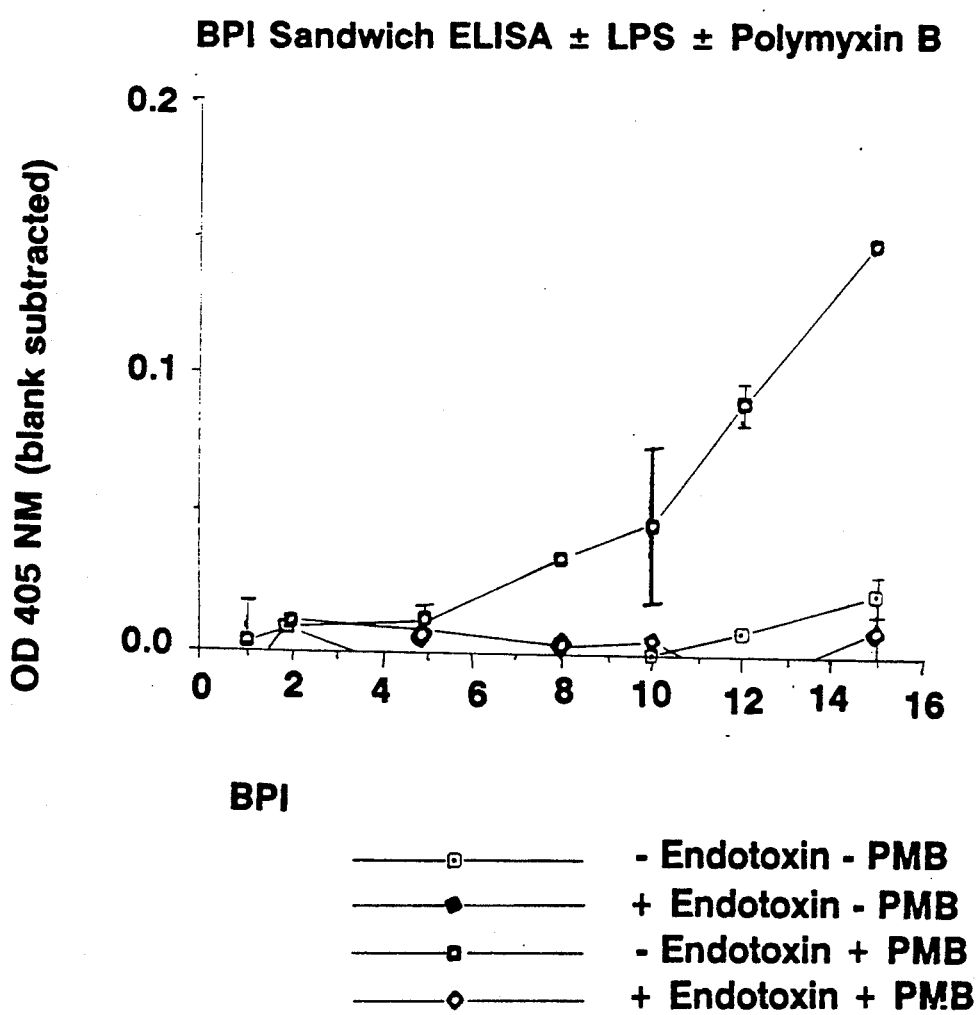

FIG. 23: BPI protein Sandwich ELISA±LPS±-Polymyxin B. The protocol is as follows: BPI protein was performed in the presence and absence of 1 μg/ml of polymyxin B sulfate and the presence or absence of 1 μg/ml *E. coli* 0111 B4 LPS using PBS+1% BSA as diluent.

Figure 14:
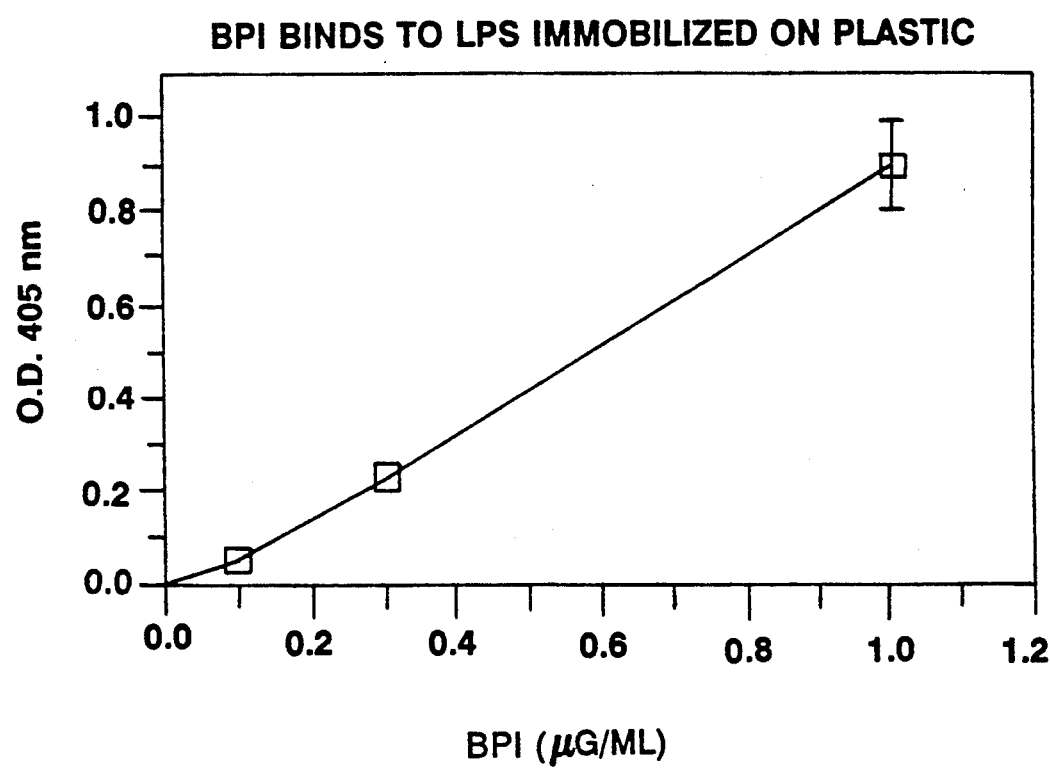
FIG. 14: A line graph showing BPI protein directly binds to LPS.

FIG. 14: Schematic drawing of cDNA encoding BPI protein.

Figure 15:
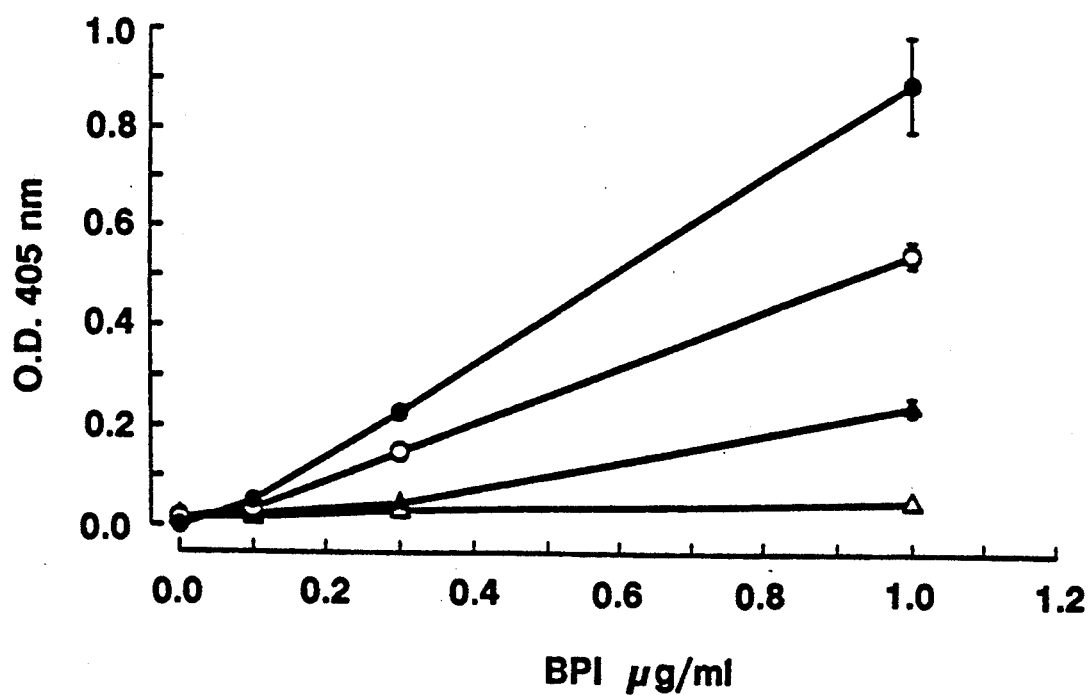
FIG. 15: A line graph showing BPI protein binding to immobilized LPS was inhibited by polymyxin B.

FIG. 15: A nucleotide and amino acid sequence of BPI protein mutagenic primer 25 kDa Pro 212 TGA which is a C-terminal truncation of BPI protein.

FIG. 26: A nucleotide and amino acid sequence of BPI protein mutagenic primer 38 kDa Pro 337 TGA which is a C-terminal truncation of BPI protein.

FIG. 27: A nucleotide and amino acid sequence of BPI protein mutagenic primer: Preferred ATG 5' HindIII which is a C-terminal truncation of BPI protein.

Figure 28:
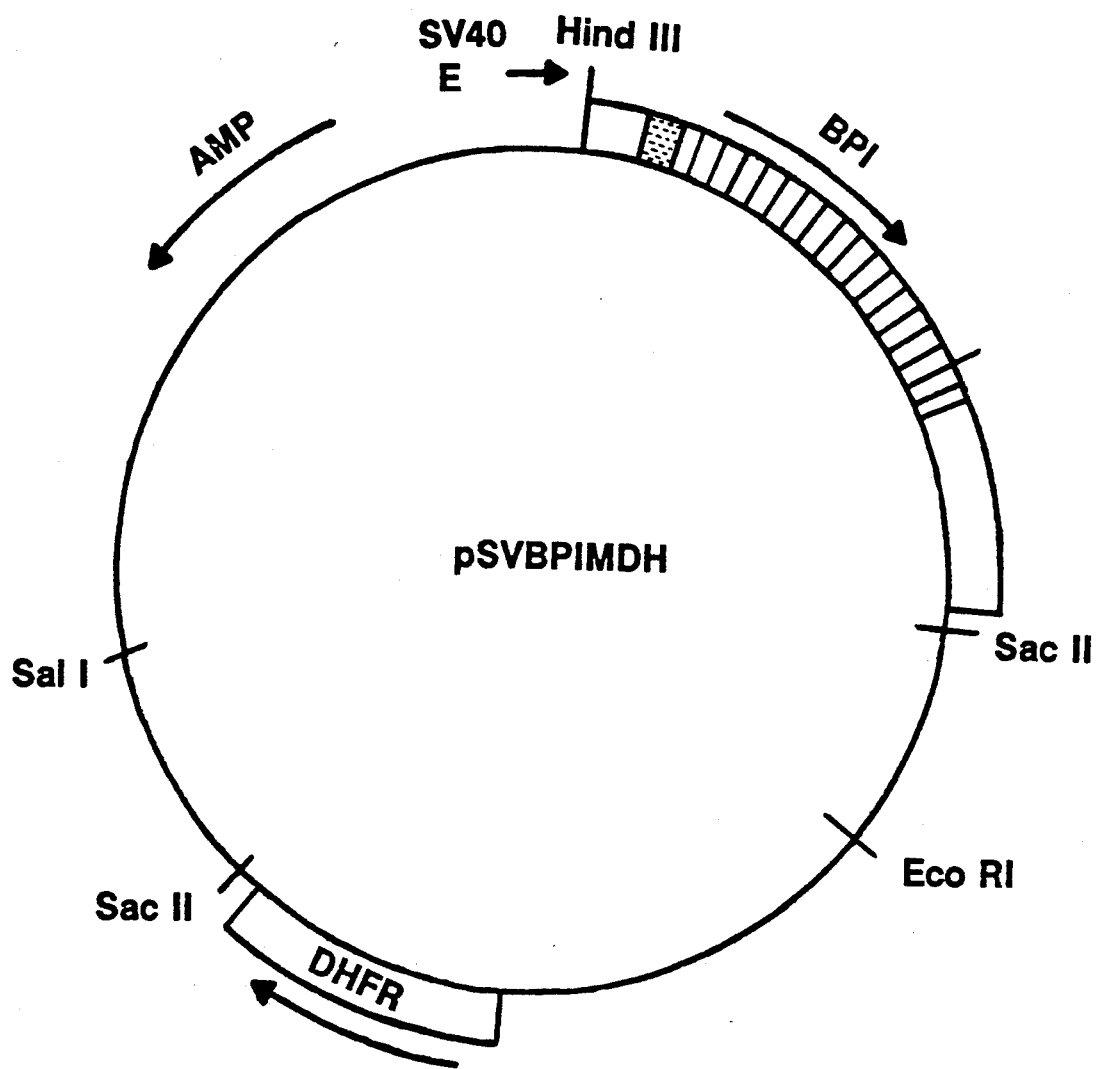

FIG. 28: A schematic drawing of pSVBPIMDH.

Figure 29A:
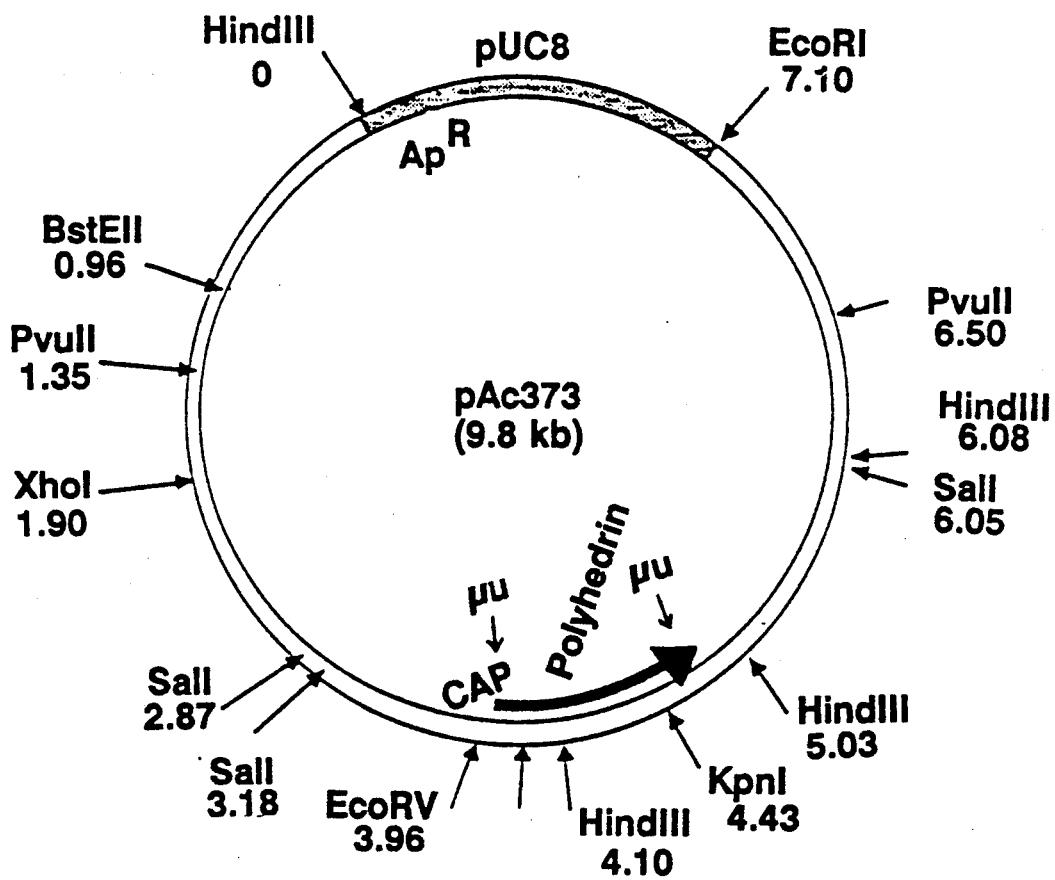
Figure 29B:
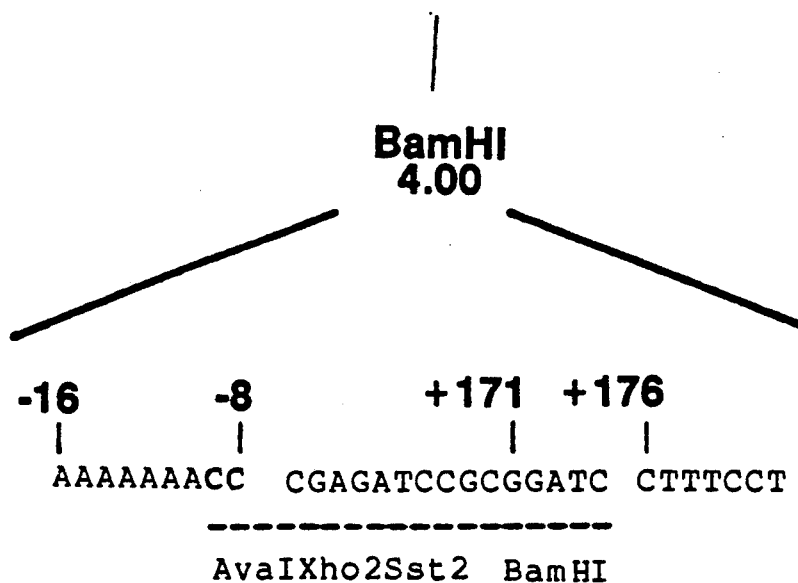

FIG. 29(A and B): A schematic drawing of pAc373.

Figure 30:
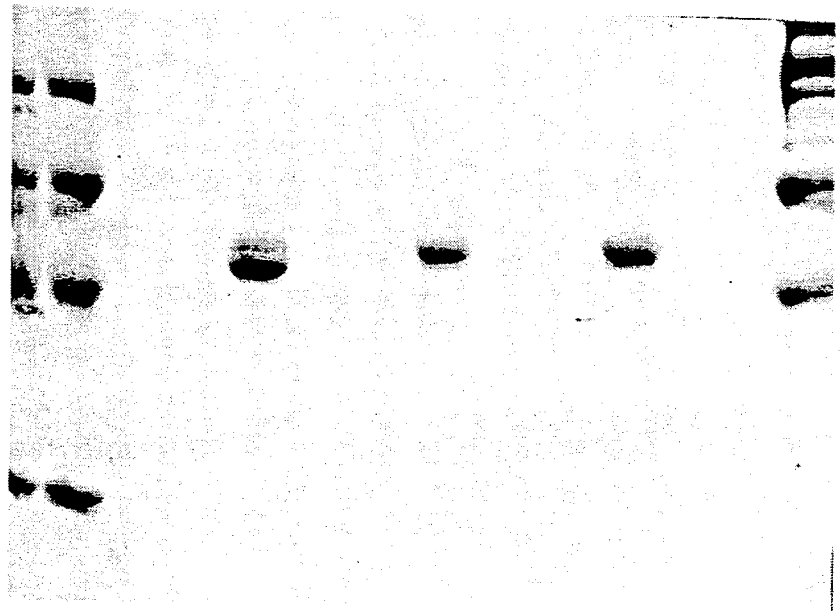

FIG. 30: SDS-PAGE analysis of (1) nBPI protein (#148104), (2) rBPI protein (#148159), and (3) rBPI protein (#148179).

FIG. 31(A-D): cDNA sequence of BPI.

Figure 32:
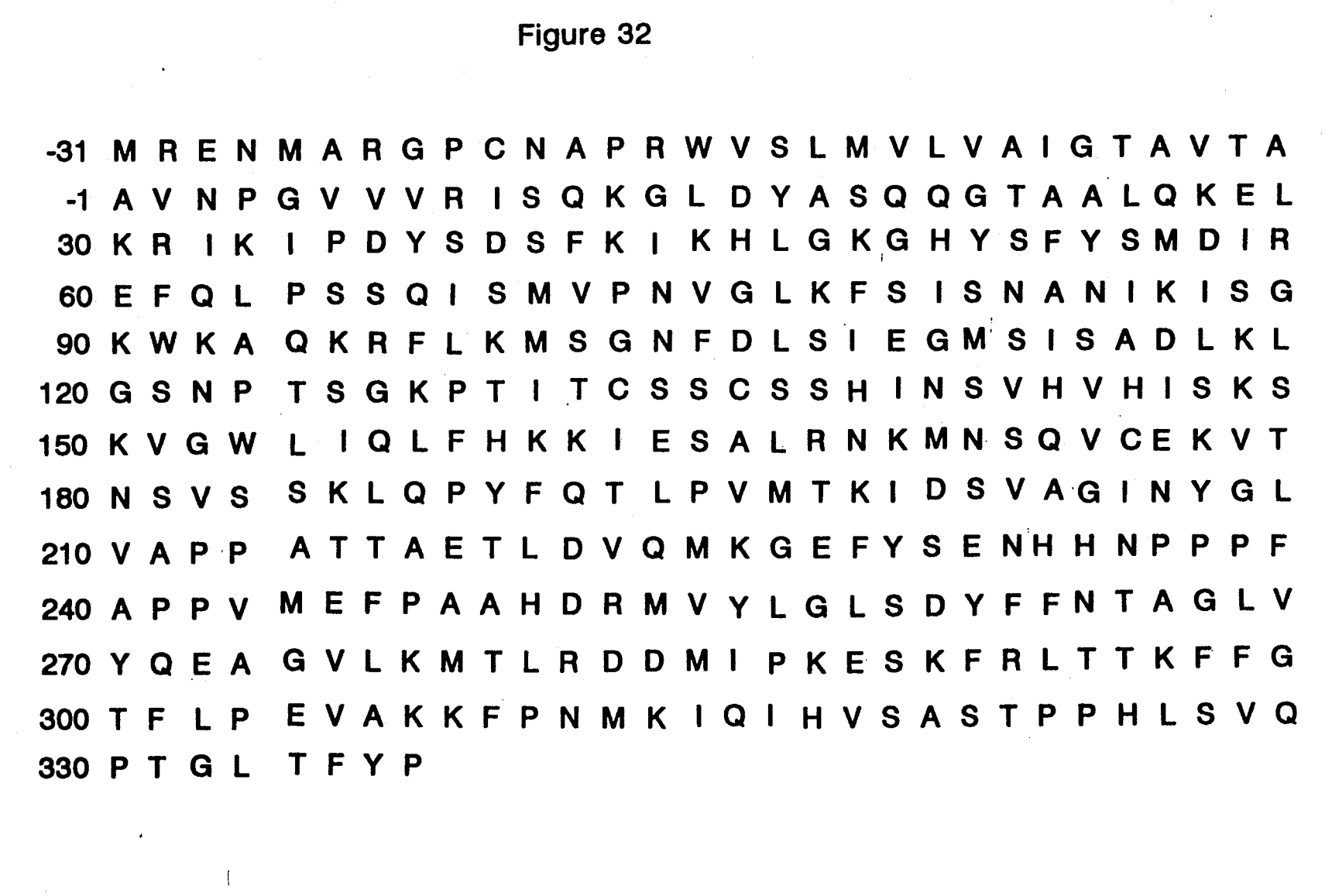

FIG. 32: Protein sequence for p337.

Figure 33:
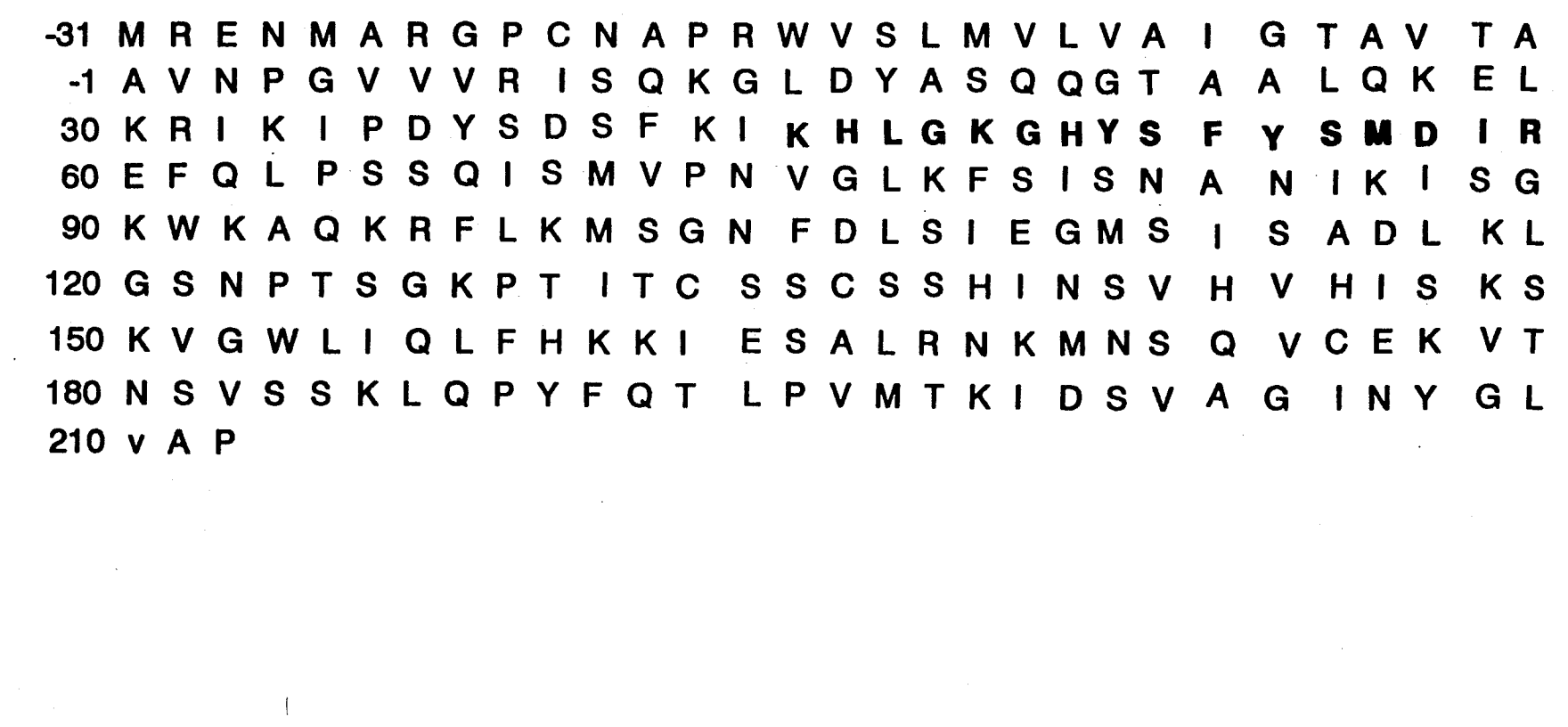

FIG. 33: Protein sequence for p212.

Figure 34:
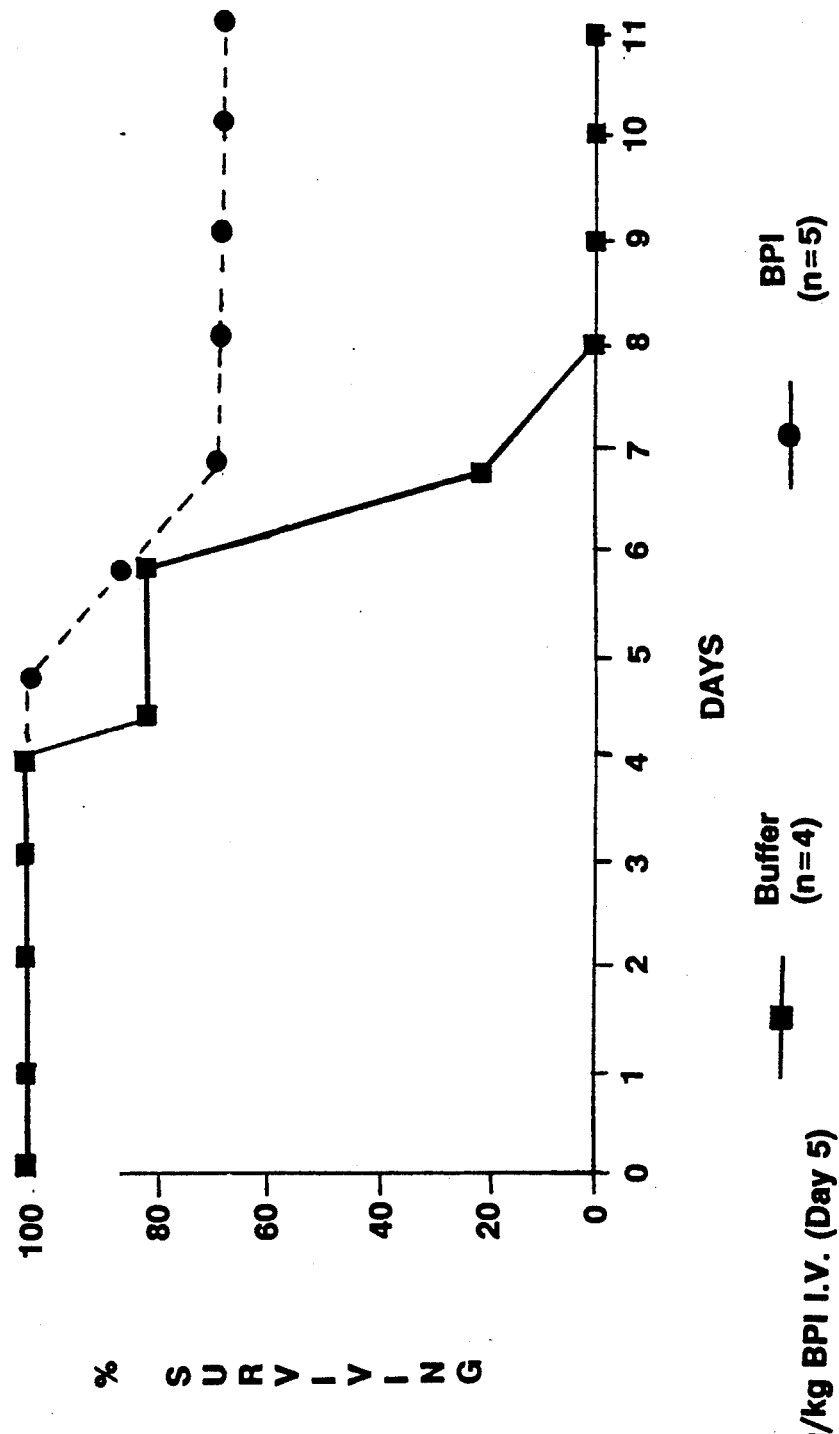

FIG. 34: Line graph showing BPI efficacy using neutropenic rat models.

Figure 35:
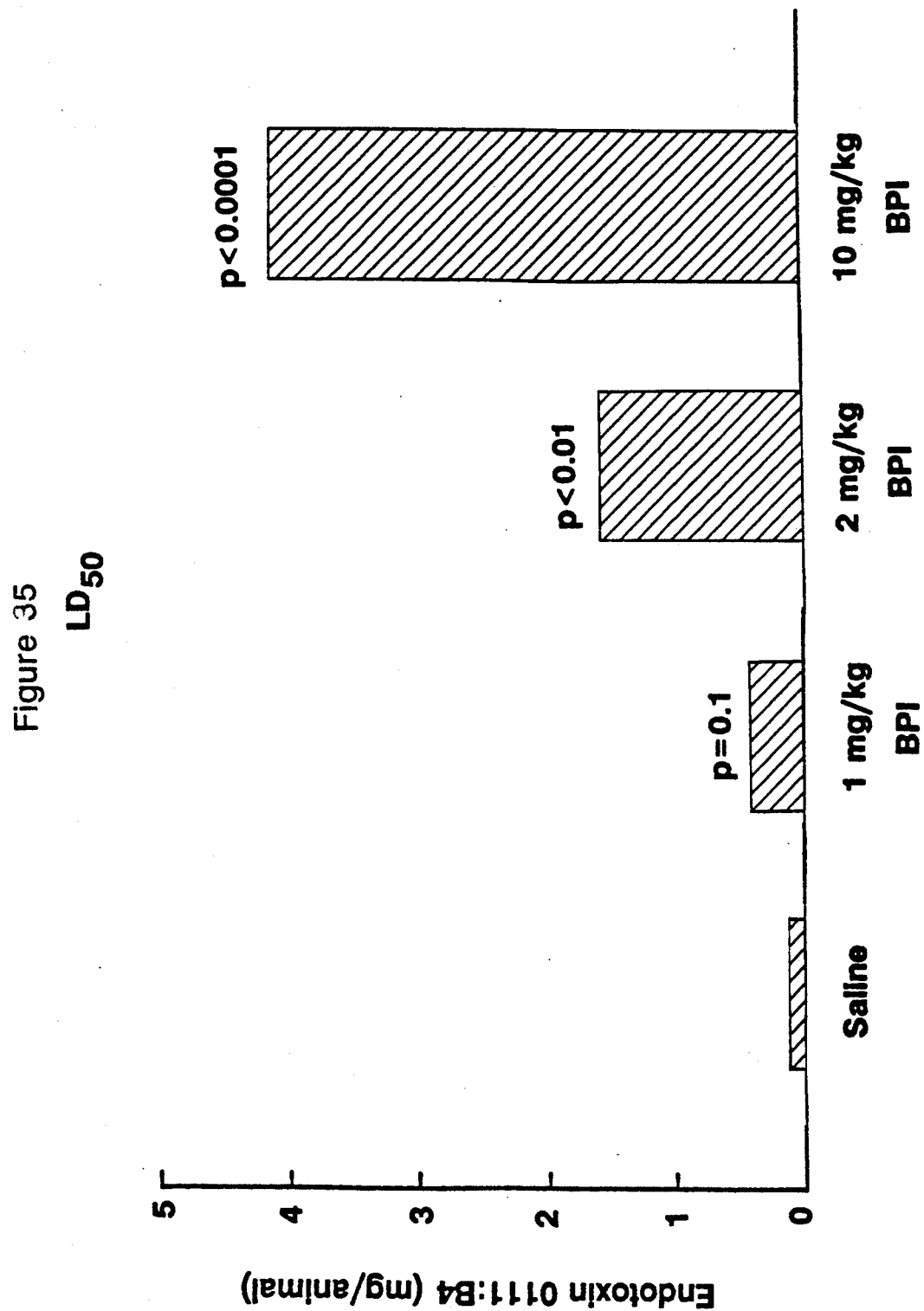

FIG. 35: Bar graph showing BPI efficacy in vivo.

Figure 36:
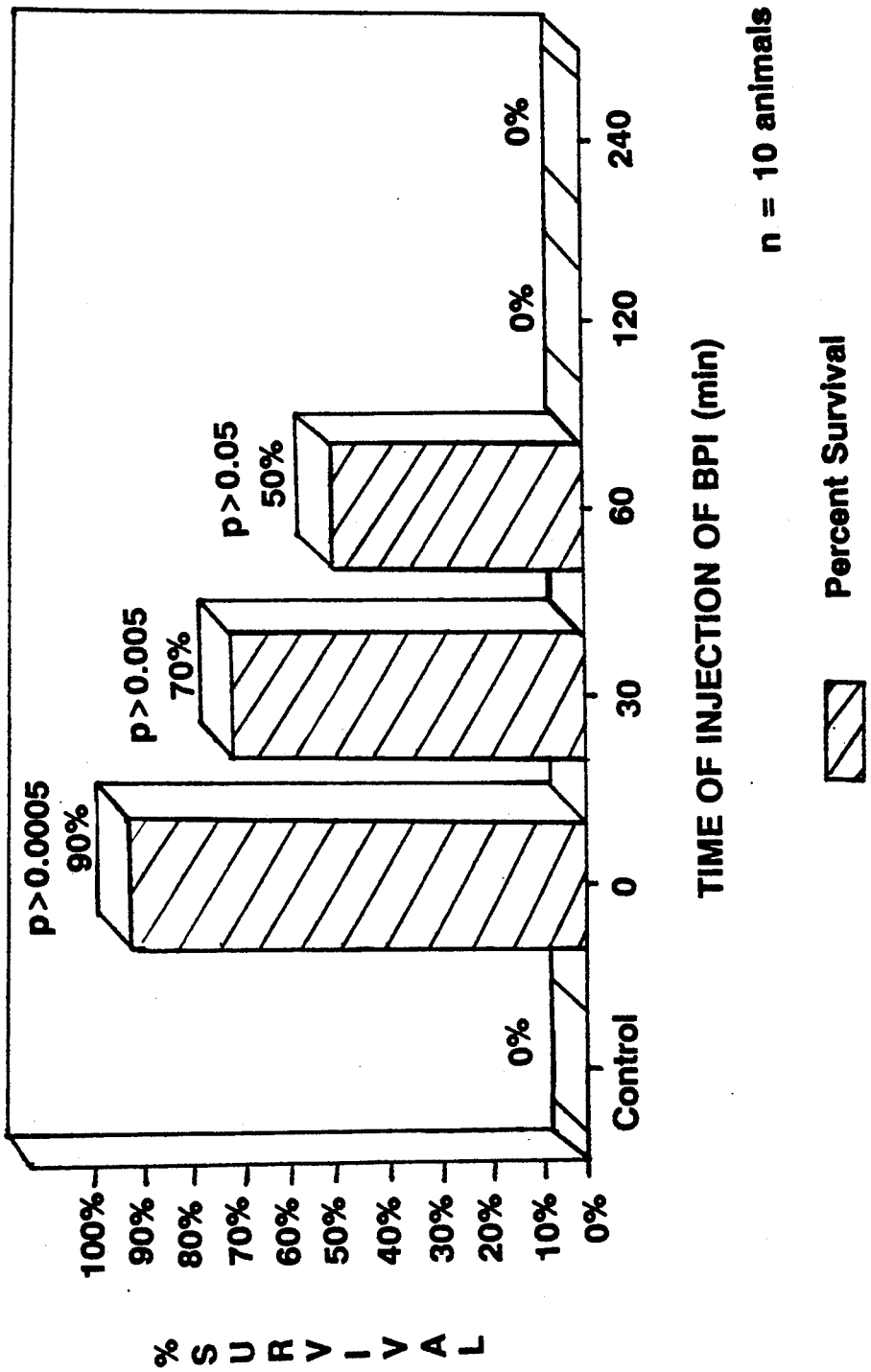

FIG. 36: Bar graph showing BPI efficacy.

Figure 37:
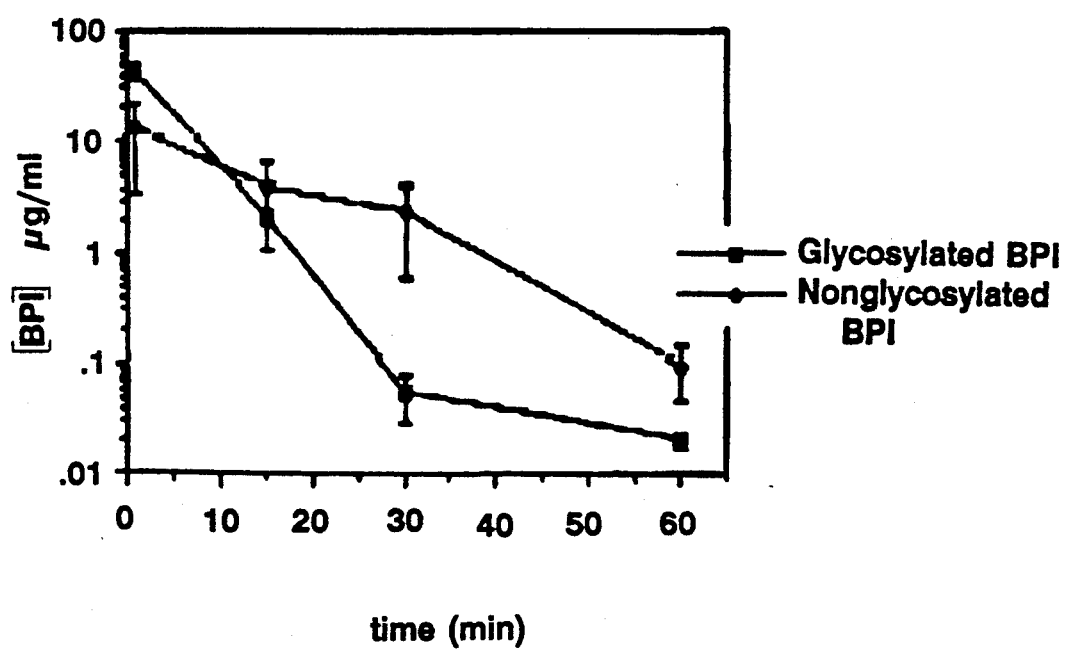

FIG. 37: Bar graph showing glycosylated and non-glycosylated BPI serum half-life.

DETAILED DESCRIPTION OF THE INVENTION

As used herein, BPI protein includes (1) recombinant BPI and polypeptide fragments of BPI, (2) biologically active polypeptide analogs of BPI, (3) biologically active genetically engineered variants of BPI, and (4) natural variants of BPI. One suitable analog of BPI comprises a polypeptide which has a molecular weight of about 25 kD and corresponds to the N-terminal amino acid sequence of BPI. As defined herein, a biologically active polypeptide analog of BPI protein means a polypeptide which has substantially the same amino acid sequence as, and endotoxin neutralizing activity of naturally-occurring BPI. Endotoxin neutralizing activity is assayed by the ability of BPI protein to inhibit $E.$ $coli$ 011:B4 LPS in the rabbit pyrogenicity test, or alternatively to increase the L.D.50 of $E.$ $coli$ 011:B4 LPS in CD1 mice. A genetically engineered variant of BPI is defined herein as a polypeptide which has a portion of the BPI amino acid sequence and substantially the same endotoxin neutralizing activity of naturally-occurring BPI. For example, a genetically engineered variant of BPI includes a portion of the BPI molecule so as to form a fused molecule with endotoxin neutralizing activity.

This invention provides a method for preventing endotoxin-associated shock in a subject which comprises administering to the subject an amount of a BPI protein effective to bind to endotoxin so as to prevent endotoxin associated shock in the subject. In accordance with the practice of this invention, the effective amount of the BPI protein is between about 0.1 and about 10 mg/kg body weight of subject. In one example, the effective amount is an amount between about 1 and about 10 mg/kg body weight of subject.

The present invention further provides a method for treating a subject suffering from endotoxin-associated shock which comprises administering to the subject an amount of a BPI protein effective to bind endotoxin so as to treat the subject suffering from endotoxin-associated shock. In accordance with the practice of this invention, the effective amount of the BPI protein is between about 0.1 and about 10 mg/kg body weight of subject. In one example, the effective amount is an amount between about 1 and about 10 mg/kg body weight of subject.

Examples of endotoxin associated shock include septic shock, bacteremia-induced shock, and circulatory shock induced by endotoxin.

The present invention provides a composition comprising a BPI protein or BPI variant and an anionic compound which composition (1) exhibits no bactericidal activity and (2) inhibits LPS-induced lethality.

In one example of the present invention, the anionic compound comprises serum albumin. Alternatively, the anionic compound is a protein. Further, the anionic compound may be a synthetic polymer such as polyglutamic acid or a dextran sulfate. Also, the anionic compound may be a proteoglycan such as heparin.

In the practice of the method of this invention the amount of BPI protein or a biologically active polypeptide analog thereof incorporated in the composition may vary widely. Methods for determining the precise amount are well known to those skilled in the art and depend inter alia upon the subject being treated, the specific pharmaceutical carrier and route of administration being employed, and the frequency with which the composition is to be administered. Preferably the amount of BPI protein is between 0.1 mg/kg body weight to 100 mg/kg body weight, and more preferably the amount of BPI protein is between 1 mg/kg body weight to 10 mg/kg body weight.

In cases of severe sepsis it is possible that antibiotics may reduce an infection; however, antibiotics may also cause an increase in endotoxin release by causing bacterial lysis which increases the risk of shock. In this instance, it would be advantageous to provide for a composition, such as that described hereinabove, which would inhibit endotoxin-induced lethality by binding to endotoxin but would not cause bacterial lysis.

The invention also provides for a BPI protein variant which (1) specifically binds to LPS, (2) competes with BPI protein for binding to LPS, and (3) inhibits LPS-induced lethality. In one example the BPI protein variant is that which is shown in FIG. 32.

In accordance with this invention, the protein variant may be a BPI protein fragment. Alternatively, the protein may be a protein variant of BPI. Specifically, said BPI protein variant could be a BPI protein fragment comprising the amino acid sequence shown in FIG. 31 beginning with a valine at amino acid position 1 and ending with a proline at amino acid position 212. Alternatively, the variant could be a BPI protein fragment comprising the amino acid sequence shown in FIG. 31 beginning with a valine at amino acid position 1 and ending with a proline at amino acid position 337 (FIG. 31). Additionally, the variant BPI protein may be the fragment shown in FIG. 26.

This invention also provides a BPI protein variant which (1) specifically binds to LPS, (2) competes with BPI protein for binding to LPS, (3) inhibits LPS lethality, and (4) does not exhibit bactericidal activity. In one example of this invention, the protein variant is that which is shown in FIG. 33.

Further, the invention provides a method for producing and secreting full-length, soluble BPI protein or protein variant thereof from a cell which comprises (a) constructing a vector comprising DNA encoding BPI; (b) transfecting the cell with the vector; and (c) culturing the cell so transfected in culture medium under conditions such that full length soluble BPI protein is secreted. In accordance with the practice of the invention, the cell is a eucaryotic cell, e.g. a mammalian cell. A chinese hamster ovary cell is preferred. Alternatively, the cell is a procaryotic cell, e.g. a yeast cell or a bacterial cell.

Gray et. al (J. Biol. Chem. 264:9505-9509, 1989) reported that the BPI protein contains three membrane spanning domains in the carboxy terminus; thus, the BPI protein is thought to be a membrane protein. Although Gray et al. were able to tansiently express BPI in human kidney cells the BPI thus made required detergent extraction from cells in order to be detected by western blotting techniques as expected for a membrane protein. Further evidence suggests that BPI protein is found intracellularly in neutrophils and HL60 cells but presently BPI protein is not known to be secreted by any mammalian cells. Thus it would be unexpected for a recombinant BPI protein to be secreted in a mammalian host (J. Weiss/I. Olsson 1984 *Blood* 69(2) 652-659.

Further, methods described in Experimental Methods results in a new molecular form of BPI, for example 148159, 148129 (FIG. 30). Specifically, BPIs produced in Chinese hamster ovary cells exhibit a slightly altered migration pattern relative to natural material on Sodium Dodecyl Sulfate -Poly Acrylamide Gel Electropharesis SDS-PAGE indicating that the molecule may be processed differently in mammalian cells than in neutrophils or HL60 cells. Such processing may be either responsible for, the molecule being secreted rather than packaged into granule membranes.

This invention further provides a method for producing a BPI protein or protein variant thereof from a gram negative bacterial cell which comprises (a) constructing a vector comprising DNA encoding BPI to which no leader peptide sequence is attached; (b) transfecting the cell with the vector; and (c) culturing the cell so transfected in culture medium under conditions such that the BPI protein or protein variant is produced.

Further, the invention provides a method for producing a BPI protein or protein variant thereof from an insect cell which comprises (a) constructing a vector comprising DNA encoding BPI; (b) transfecting the cell with the vector; and (c) culturing the cell so transfected in culture medium under conditions such that the BPI protein or protein variant is expressed. Such insect cells may function as hosts for a baculovirus vector containing the BPI protein sequence. Moreover, BPI protein derived from insect cells exhibit an even different migration pattern on SDS-PAGE than that derived from either mammalian cells or the BPI protein found naturally-occurring in neutrophils. Thus, the invention provides for a new molecular species of BPI protein as processed by baculovirus infected insect cells.

The present invention provides a BPI protein or protein variant produced by the aforementioned methods. The present invention further provides a BPI protein or protein variant produced by the aforementioned methods which is nonglycosylated.

Additionally, the present invention provides for a method for inhibiting LBP mediated-TNF production in a subject which comprises administering to the subject a suitable amount of BPI protein under conditions such that BPI protein binds to LPS so as to prevent LBP binding to LPS thereby inhibiting LBP-mediated TNF production. Ulevitch et al. (J. Biol. Chem. 263: 13479-13481, 1988) suggested that BPI protein and LBP have significant sequence homology and the re fore similar functions. In fact, BPI protein acts as an antagonist to LBP. LBP forms complexes with LPS which subsequently bind to monocytes resulting in TNF production. BPI protein on the other hand binds LPS and prevents it from binding LBP and inhibiting TNF production. Thus BPI protein is directly antagonistic to LBP.

Further, the invention provides BPI protein fragments or LBP fragments which would compete with BPI protein for binding to the lipid A domain of endotoxin, thereby, acting as LBP antagonists. Such fragments include BPI protein fragments or LBP fragments which contain only the amino terminal fragment of the molecule absent the carboxy terminal domain. The carboxy terminal domain of LBP is required for binding to and activation of monocytes resulting in an increase in TNF production. Alternatively the amino terminal fragment of LBP could be spliced to the carboxy terminal half of BPI to form a truncated molecule with endotoxin neutralizing activity.

The subject invention additionally provides a BPI protein variant which (1) specifically binds to a lipid A domain of LPS, (2) competes with BPI for binding to the lipid A binding site of LPS, and (3) neutralizes endotoxin. An example of the BPI protein variant is the protein variant as shown in FIG. 32. Another example of the BPI protein variant is the protein variant as shown in FIG. 33.

The subject invention additionally provides a BPI protein variant which (1) specifically binds to the lipid A domain of LPS, (2) competes with BPI for binding to the lipid A domain of LPS, (3) neutralizes endotoxin, and (4) does not exhibit bactericidal activity.

Also, the invention provides a method for producing a BPI protein or protein variant thereof from a gram negative bacterial cell which comprises (a) constructing a vector comprising DNA encoding BPI to which no leader peptide sequence is attached; (b) transfecting the cell with the vector; and (c) culturing the cell so transfected in culture medium under conditions such that the BPI protein or protein variant is produced.

Apparently, when the signal sequence is included in the expression plasmid as provided in a full length clone and reported by Gray et al. (1989) *J. Biol. Chem.*, 264:9505) no bacterial colonies are obtained, whereas, numerous colonies can be obtained if the signal sequence is deleted. Further, the method described hereinabove provide for expression of full length BPI protein in a nonglycosylated form. The invention further provides for a nonglycosylated form of BPI substantially free of glycosylated BPI. Further this method provides for expression of molecular variants of BPI protein including, but not limnited to, a fragment comprising amino acid residures 1-212 of BPI protein (BPIpro212).

Additionally, this invention provides a method for producing a BPI protein or protein variant thereof from an insect cell which comprises (a) constructing a vector comprising DNA encoding BPI; (b) transfecting the cell with the vector; and (c) culturing the cell so transfected in culture medium under conditions such that the BPI protein or protein variant is expressed.

This invention also provides a BPI protein variant produced by the above-described methods including nonglycosylated forms of the BPI protein variant substantially free of glycosylated forms of the BPI protein variant.

Additionally, this invention provides a full length, soluble BPI protein produced and secreted by the above-described methods.

The present invention further provides a purified BPI protein variant as described hereinabove. In one example, the purified BPI protein variant has the amino acid sequence shown in FIG. 32. Alternatively, the purified BPI protein variant has the amino acid sequence shown in FIG. 33.

This invention also provides a nucleic acid molecule encoding the purified BPI protein variant having the amino acid sequence shown in FIG. 32. Also, the invention provides a nucleic acid molecule encoding the purified BPI protein variant having the amino acid sequence shown in FIG. 33.

This invention further provides a cDNA encoding the BPI protein variants described herein. Further, this invention provides a plasmid which comprises the nucleic acid molecule encoding the purified BPI protein variant having the amino acid sequence shown in FIG. 32 and nucleic acid molecule encoding the purified BPI protein variant having the amino acid sequence shown in FIG. 33.

This invention further provides a host vector system, comprising a plasmid, which comprises a nucleic acid molecule encoding the purified BPI protein variant having the amino acid sequence shown in FIG. 32 or a nucleic acid molecule encoding the purified BPI protein variant having the amino acid sequence shown in FIG. 33, in a suitable host cell.

In one example, the suitable host cell is a bacteria cell. In another example, the suitable host cell is a eucaryotic cell.

The present invention also provides a method for producing a BPI protein or protein variant thereof comprising growing the above-described host vector system so as to produce the protein in the host and recovering the protein so produced.

Further, this invention provides a method for preventing septic shock associated with the presence of endotoxin in a subject which comprises administering to the subject a purified, endotoxin-free, human Bactericidal/Permeability Increasing Protein or any of the BPI protein variant described herein under conditions such that the BPI or protein variant thereof binds to endotoxin and thereby inhibits LPS-induced lethality so as to thereby prevent septic shock.

The invention further provides a method for preventing bacteremia-induced shock associated with the presence of endotoxin in a subject which comprises administering to the subject a purified, endotoxin-free, human Bactericidal/Permeability Increasing Protein or any BPI protein variant described herein under conditions such that the BPI or protein variant thereof binds to endotoxin and thereby inhibits LPS-induced lethality so as to thereby prevent bacteremia-induced shock.

The present invention also provides a method for treating a subject suffering from septic shock associated with the presence of endotoxin-associated LPS in a subject which comprises administering to the subject a purified, endotoxin-free, human Bactericidal/Permeability Increasing Protein or any BPI protein variant described herein under conditions such that the BPI or protein variant thereof binds to endotoxin and thereby inhibits LPS-induced lethality so as to thereby treat the subject.

Additionally, this invention provides a method for treating a subject suffering from shock induced by bacteremia and associated with the presence of endotoxin in a subject which comprises administering to the subject a purified, endotoxin-free, human Bactericidal/Permeability Increasing Protein or any BPI protein variant described herein under conditions such that the BPI or protein variant thereof binds to endotoxin and thereby inhibits LPS-induced lethality so as to thereby treat the subject.

This invention is illustrated in the Experimental Details section which follows. This section is set forth to aid an understand of the invention but is not intended to, and should not be construed to, limit in any way the invention as set forth in the claims which follow.

Experimental Details

EXAMPLE 1

Purification and Characterization of BPI produced under non-endotoxin-free conditions.

Materials and Methods

Reagents

Lipopolysaccharide from *E. coli* 0111:B4, *S. typhimurium* wild type, glycolipid from *S. typhimurium* RE mutant, and Lipid A from *S. typhimurium* RE mutant, and LPS from *P. aeruginosa* were purchased from RIBI Immmunochem Research, Inc., Hamilton, Mont.; Fmet-Leu-Phe (FMLP) and polymyxin B Sulfate from Sigma Chemical Co., St. Louis, Mo.; Hank's Balanced Salt Solution without calcium, magnesium and phenol red (HBSS) from Hazelton Research Products, Denver, Pa.; Ficoll-Paque, Percoll and Macrodex from Pharmacia Inc., Piscataway, N.J.; TNF and anti-TNF from Endogen, Boston Mass.; Fluorescein conjugated goat-anti-mouse IgG from TAGO Inc., Burlingame, Calif.: IgG1 control antibody from Coulter Immunology, Hialeah, Fla.; Phycoerythrin (PE) conjugated anti CR3 (Leu-15) and IgG2a control from Becton Dickinson, Mountain View, Calif., Anti CR1 monoclonal antibody, Yz-1, was a kind gift from Dr. Rick Jack at Harvard University.

Azurophil Granule Isolation and Extraction

Granulocytes were isolated from buffy coats obtained from local blood banks. Buffy coats were diluted 3–4× in HBSS and granulocytes were separated from mononuclear cells by centrifugation through 64% Percoll. The pellet was subjected to diisopropylfluorophosphate (DFP), washed, and resuspended in ice cold lysis buffer (10 mM PIPES, pH 6.8, 100 mM KCL, 3 mM NaCl, 3.5 mM MgCl2) and disrupted by nitrogen cavitation (Parr Instrument Co., Moline, Ill.). Azurophil granules were isolated on discontinuous Percoll gradients as described by Borregaard. [Borregaard, N., J. M. Heiple, E. R. Simons, and R. A. Clark, J. Cell. Biol., 97: 52–61 (1983)] The azurophil granules were collected and Percoll was removed by centrifugation at 180,000×G for 2 hours. The granules were lysed by 4 cycles of freeze-thaw followed by 1 minute of sonication. The lysed granules were extracted in an equal volume of 100 mM glycine, pH 2 by vortexing intermittently for 1 hour at room temperature. The acid extract was clarified by centrifugation at 30,000×G for 20 minutes and at 200,000×G for 30 minutes.

Neutrophil Isolation

Venous blood was drawn from healthy volunteer donors into acid citrate dextrose anticoagulant and immediately placed on ice. Five parts of blood were mixed with 1 part of cold Macrodex, and allowed to settle for 1.5–2 hours at 4° C. Leukocyte-rich plasma was washed 1× in cold HBSS, then resuspended in HBSS and layered over Ficoll-Paque. If significant erythrocyte contamination was present, the granulocyte pellet was subjected to hypotonic lysis. The cells were washed 2× in HBSS and resuspended in HBSS+2% autologous plasma to give a final granulocyte concentration of $1 \times 10^6$/ml in the incubation mixture.

BPI protein Purification: Non endotoxin-free

Approximately 2 mg of crude azurophil granule extract was separated by size on a Biosil (TSK-250) (7.8 mm×600 mm) high performance size exclusion column using 50 mM glycine and 100 mM NaCl buffer, pH 2.0, under isocratic conditions of a flow rate of 1 ml/min. Column fractions with the greatest LPS inhibitory activity contained a large proportion of the 54 KD species as shown by SDS PAGE. These TSK fractions were pooled and run over an Aquapore weak cation exchange (WCX) column (2.1 mm×30 mm) using 50 mM citrate, pH 5.5, and eluted in a gradient of 0–75%, of 50 mM citrate and 1M NaCl (Buffer B) in 25 min, then 75–100% Buffer B in 5 min with a flow rate of 200 ml/min. Material of approximately 55 KD was recovered from cation exchange as judged by sodium dodecyl sulfate polyacrylamide gel electrophoresis (SDS-PAGE). In some experiments BPI protein was further purified by reverse phase HPLC on a Vydac C4 column loaded in 0.1% CH3CN plus 0.1% TFA, and eluted over 30 min with a linear gradient to 0.1% TFA plus 60% CH3CN.

BPI Inhibition of Neutrophil stimulation by LPS

The neutrophil complement receptor upregulation assay was performed essentially as previously described (*J. Immunol.* 144: 662–666). Isolated neutrophils were kept on ice until incubated with or without stimuli at 37° C. for 30 minutes. Following the incubation, cells were washed in a large volume of cold PBS+0.05% Na Azide+2% autologous plasma. Pellets were divided in two, one stained with 50 µl control IgG1 antibody (20 µg/1×10⁶ cells), the other with 50 µl of 20 µg/1×10⁶ cells anti-CR1 for 30 minutes at 0° C. Following this incubation the cells were washed 2× with PBS+autologous plasma, then stained with goat-anti-mouse IgG-FITC, and in some experiments, 20 µl of IgG2a-phycoerythrin (PE) in control wells, and 20 µl Leu-15 PE in test wells. Following a 30 minute incubation at 0° C. and 2 more washes, the cells were analyzed by flow cytometry on a Becton Dickinson FACStar flow cytometer (Becton Dickinson, Mountain View, Calif.). Neutrophil stimulation was measured by comparing mean fluorescence intensity of samples which had been incubated in HBSS+2% autologous plasma alone (control) to those incubated with LPS or LPS which had been preincubated for 30 minutes at 37° C. with BPI protein or polymyxin B. Data are expressed as % stimulation or % inhibition and were calculated using the mean fluorescence intensity (Fl), on a log scale, according to:

% Stimulation=[(Experimental−Control)/
(Maximum−control)]×100 and

% Inhibition=1−[(+Inhibitor)−(Control)]/
[(−Inhibitor)−(Control)]×100.

Amino Acid Analysis

Vapor phase hydrolysis of BPI protein and amino acid derivitization was performed using a Pico-tag Workstation (Waters, Milford Mass.) and chromatographic analysis of the phenylthiocarbamyl amino acids was performed on an applied Biosystems 130 A MPLC using Protocols provided by the manufacturer.

Sequence Analysis

BPI protein N-terminal sequence was analyzed by automated Edman degradation using an applied Biosystems 477A pulse liquid phase sequenator (Applied Biosystems, Foster city, Calif.). Phenyltheohydantion amino acid analysis was performed on line using an applied biosystems Model 120A liquid chromatograph.

Results

As previously discussed, BPI protein is a cationic 50–60,000 M.W. protein first purified from human neutrophil granules by Weiss et al. (Weiss, J., P. Elsbach, I. Olsson and H. Odegerg. 1978. J. Biol. Chem. 253:2664.). BPI protein alters bacterial cell membrane permeability and has bactericidal activity specifically against gram negative microorganisms in vitro. To date, the literature on BPI protein has focused exclusively on its bactericidal activity in vitro.

We report that BPI protein binds to LPS and inhibits both neutrophil and monocyte responses to soluble LPS in vitro. BPI protein also inhibits LPS activity in the Limulus Amebocyte Lysate (LAL) assay. Our research has identified BPI protein as a lead molecule for the development of novel therapies against endotoxic shock.

Figure 1A:
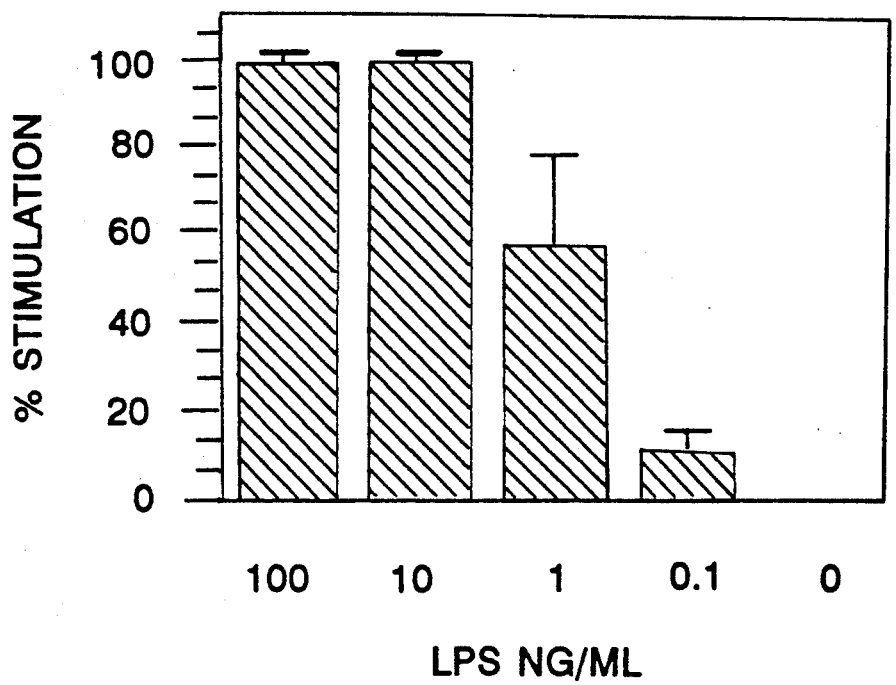
FIG. 1a: Mean fluorescence intensity of CR1 on freshly isolated neutrophils was measured by FACS analysis. Cells were stimulated with varying doses of *E. coli* 0111:B4 LPS as described in Materials and Methods. Since mean fluorescence intensity varies between individuals, the data is expressed as percent of the maximum response observed. Data shown represents the mean +/− Standard Error of three experiments.

Human neutrophils may be stimulated both in vivo and in vitro by lipopolysaccharide. Upon activation, surface expression of receptors for C3b and C3bi (CR1 and CR3 respectively), increases. Using the Fluorescence Activated Cell Sorter (FACS), fluorescence intensity of freshly isolated human neutrophils was measured following stimulation with increasing doses of 0111:B4 LPS (FIG. 1a). Because commonly observed maximum stimulation was at or above 10 ng/ml, experiments testing for inhibition of 0111:B4 LPS used 10 ng/ml as the stimulatory dose. All experiments were performed in duplicate. In most experiments, data is shown only for CR1 since we did not observe any condition where neutrophil stimulation caused upregulation of CR1 or CR3 alone (M. Marra et al. (1990) *J. Immunol.* 144(2):662–666).

Figure 1B:
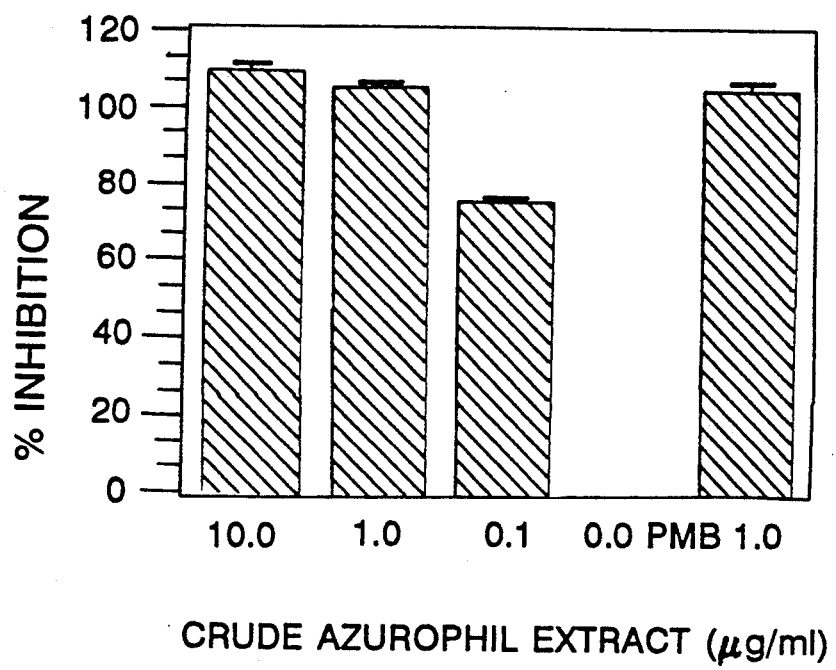
FIG. 1b: LPS (10 ng/ml) was preincubated with varying doses of crude azurophil extract for 30 minutes at 37° C. prior to testing for neutrophil stimulation. Data shown represents the mean +/− Standard Error of duplicates from a representative experiment. Values are expressed as % inhibition of the response to LPS alone.

To determine whether proteins found in neutrophil azurophil granules could interfere with the neutrophil response to LPS, crude acid extracts of azurophil granules were pre-incubated with LPS for 30 minutes at 37° C. The mixture was then tested for its ability to stimulate neutrophils. Azurophil protein (1 µg/ml) could effectively block stimulation of 1×10⁶ polymorphonuclear leukocytes (PMN)/ml by 10 ng/ml of LPS (FIG. 1b). This effect was not observed using glycine extraction buffer preincubated with LPS, nor was there any stimulation of neutrophils using crude extract or glycine buffer control.

To further investigate which of the proteins in the extract was/were responsible for inhibitory effect, crude acid extracts were separated by reverse phase HPLC; each peak was assayed separately for LPS inhibitory activity. The identity of each of the peaks was previously determined using a two-dimensional purification approach involving microbore reverse phase HPLC in first dimension followed by SDS PAGE, electroblotting and microsequencing. The azurophil proteins can be resolved into 10 discrete peaks whose identities are shown in Table 1. The amino acid sequences shown are for the first 15 amino acids of the N-terminal.

Figure 2:
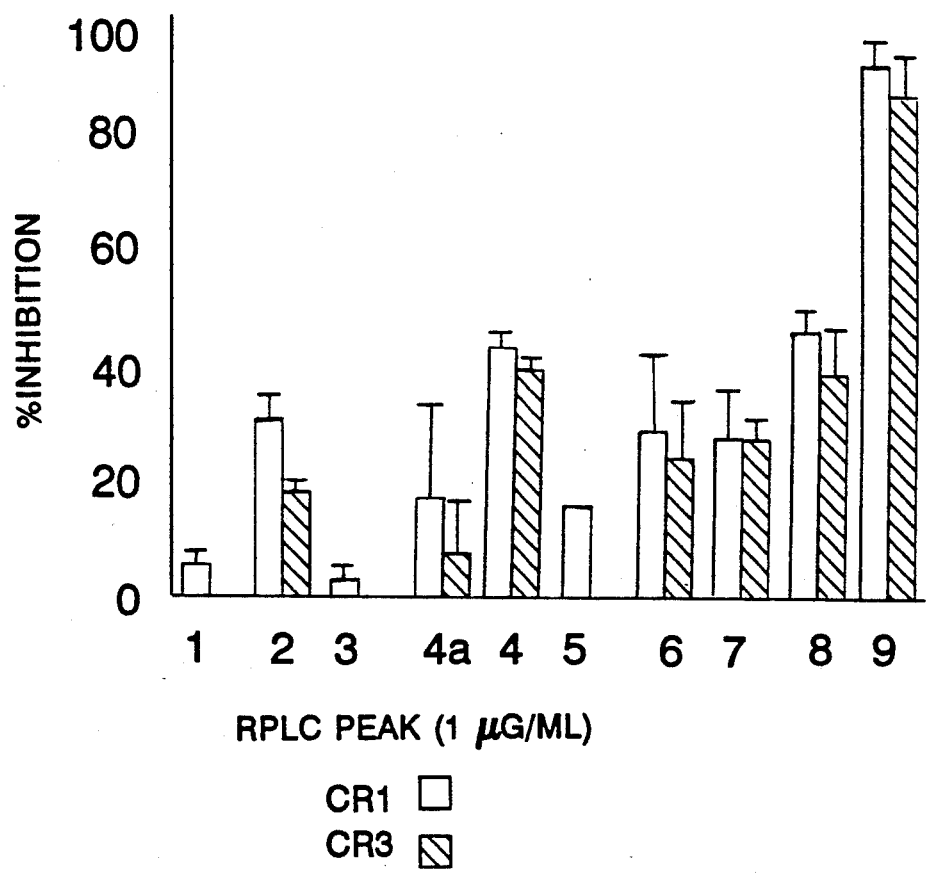
FIG. 2: Crude azurophil extract was separated by reverse phase HPLC. Each peak was collected manually and protein concentrations were determined by amino acid analysis. An aliquot (1 μg) of each peak was dried in the presence of low endotoxin BSA, then re-dried in the presence of pyrogen free 0.1% acetic acid. Data shown represent the mean +/− Standard Error of duplicates from a representative experiment.

LPS inhibitory activity of 1 μg of each peak is shown in FIG. 2. As shown, peak 9 had the highest LPS neutralizing activity. The major protein species in this peak has N-terminal identity with Bactericidal/Permeability Increasing Protein (BPI) described previously (Weiss, J., P. Elsbach, I. Olsson and H. Odeberg, *J. Biol. Chem*, 253 (8): 2664-2672 (1978)). BPI protein has been shown to contain the majority of the gram negative bactericidal activity in azurophil granule protein extracts.

showed that maximal CR1 upregulation is observed using 10 ng/ml LPS (FIG. 4). Neutrophil stimulation with LPS was not inhibited by exogenous anti-TNF antibodies, suggesting that LPS acted directly on neutrophils in this system.

Figure 4A:
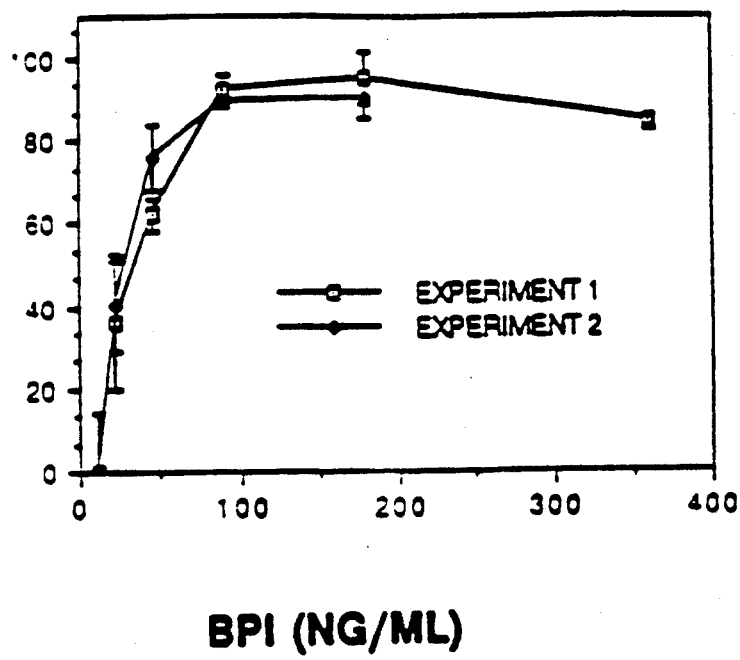
FIG. 4: 0111:B4 LPS (10 ng/ml) was preincubated with varying doses of (A) purified BPI, and (B) polymyxin B, then tested for neutrophil stimulatory activity. Results from two experiments shows inhibition of complement receptor expression on neutrophils with Standard Errors for replicate samples.

BPI protein inhibits the neutrophil response to LPS (FIG. 4a). Inhibition of CR upregulation was complete at a dose of approximately 1.8-3.6 nM (100-200 ng/ml) BPI protein. The neutrophil response to formulated peptide ($10^{-7}$M FMLP) was not inhibited by BPI protein demonstrating that the effect was specific for endotoxin.

Figure 4B:
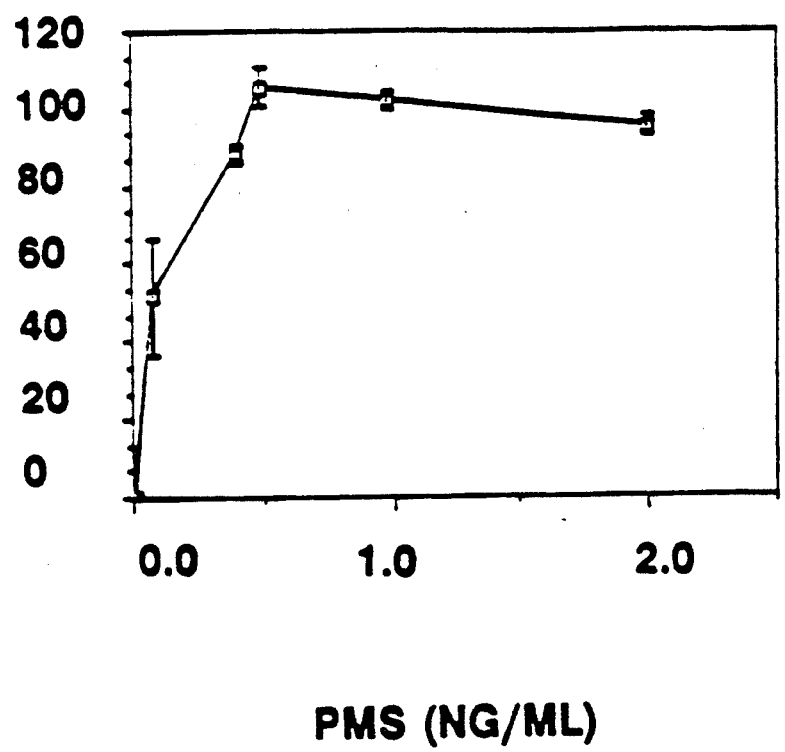

FIG. 4b shows a similar does response curve for the polypeptide antibiotic Polymyxin B (PMB). Polymyxin B binds to the Lipid A moiety of LPS and neutralizes some of its toxic effects both in vivo and in vitro. poly-

TABLE 1

| Peak | Identity | 1 | 5 | 10 | 15 |
|------|----------|---|---|----|----|
| 1 | Defensins (HNP-2) | C Y C R I | P A C I | A G E R R | Y |
| 2 | Granulocidin (HNP-4) | V C S C R | L V F C | R R T G L | R |
| 3 | Eosinophil Cationic Protein (ECP) | X P P Q F | T R A Q | W F A I | Q H |
| 4a | Eosinophil-Derived Neurotoxin (EDN) | K P P Q F | T X A Q | X F E T | Q X |
| 4b | Cathepsin G | I I G G R | E S R P | H S R P | Y M |
| 5a | Lysozyme | K V F E R | X E L A | R T L K | R L |
| 5b | Eosinophil Major Protein (MBP) | T C R Y L | L V R S | L Q T F | S Q |
| 6 | Unknown | I V G G R | K A R P | X Q F P | F L |
| 7 | Unknown | I V G G H | E A Q P | H S R P | Y M |
| 8a | Myeloperoxidase | V N C E T | S C V Q | Q P P C | F P |
| 8b | Elastase | I V G G R | R A R P | H A X P | F M |
| 9 | Bactericidal/Permeability Increasing Protein (BPI) | V N P G V | V V R I | S Q K G L | D |

Cathepsin G showed some inhibition of LPS, but the data between experiments were not as reproducible as for peak 9. Cathepsin G has been shown to bind to LPS in vitro and to kill gram negative organisms, although to a lesser extent than BPI. Other proteins which have demonstrated microbicidal activity against gram negative organisms are elastase and the defensins. However, these proteins (1 μg/ml) did not inhibit the stimulatory activity of LPS on neutrophils.

Figure 3A:
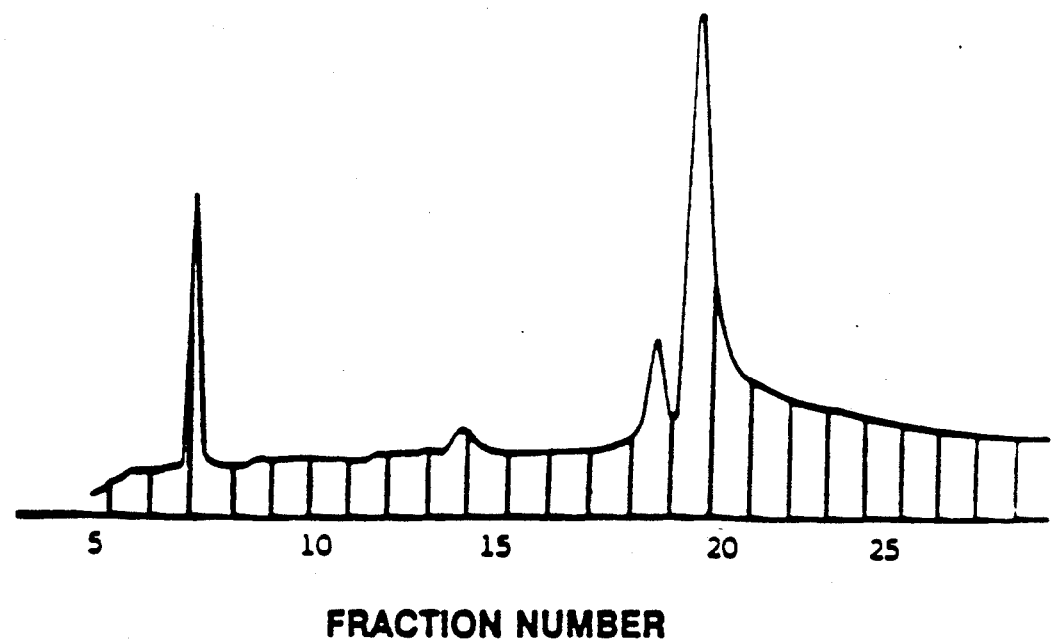
FIG. 3: (a1/a2/a3) BPI protein purified by size exclusion followed by cation exchange HPLC was subjected to reverse phase HPLC and fractions were tested for LPS inhibitory activity.
FIG. 3b: Data show the RPLC profile of the 2× purified material along with the inhibitory activity and SDS PAGE analysis of fractions 20, 22 and 23.
Figure 3B:
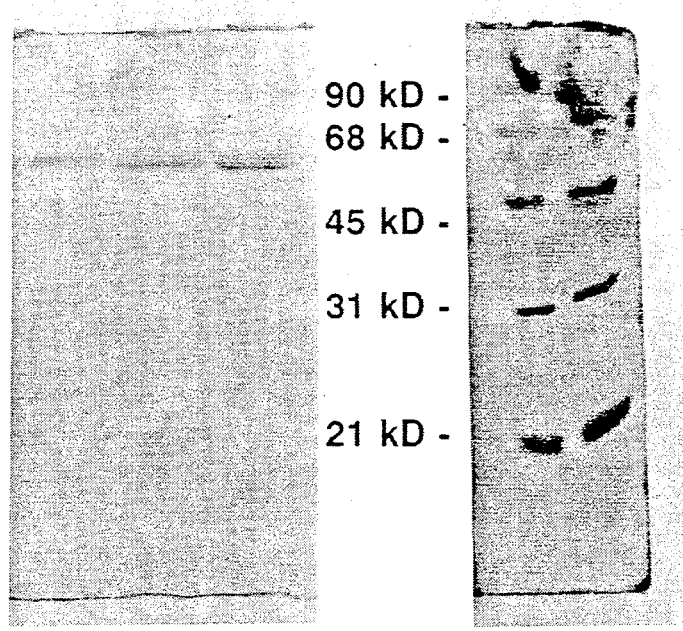

LPS inhibitory activity of crude azurophil extracts was further characterized and purified using size exclusion and ion exchange followed by reverse phase chromatography. LPS inhibitory activity comigrates with a pure approximately 55 KD band seen on SDS PAGE (FIG. 3b) and identified as BPI by N-terminal sequence analysis.

Figure 5A:
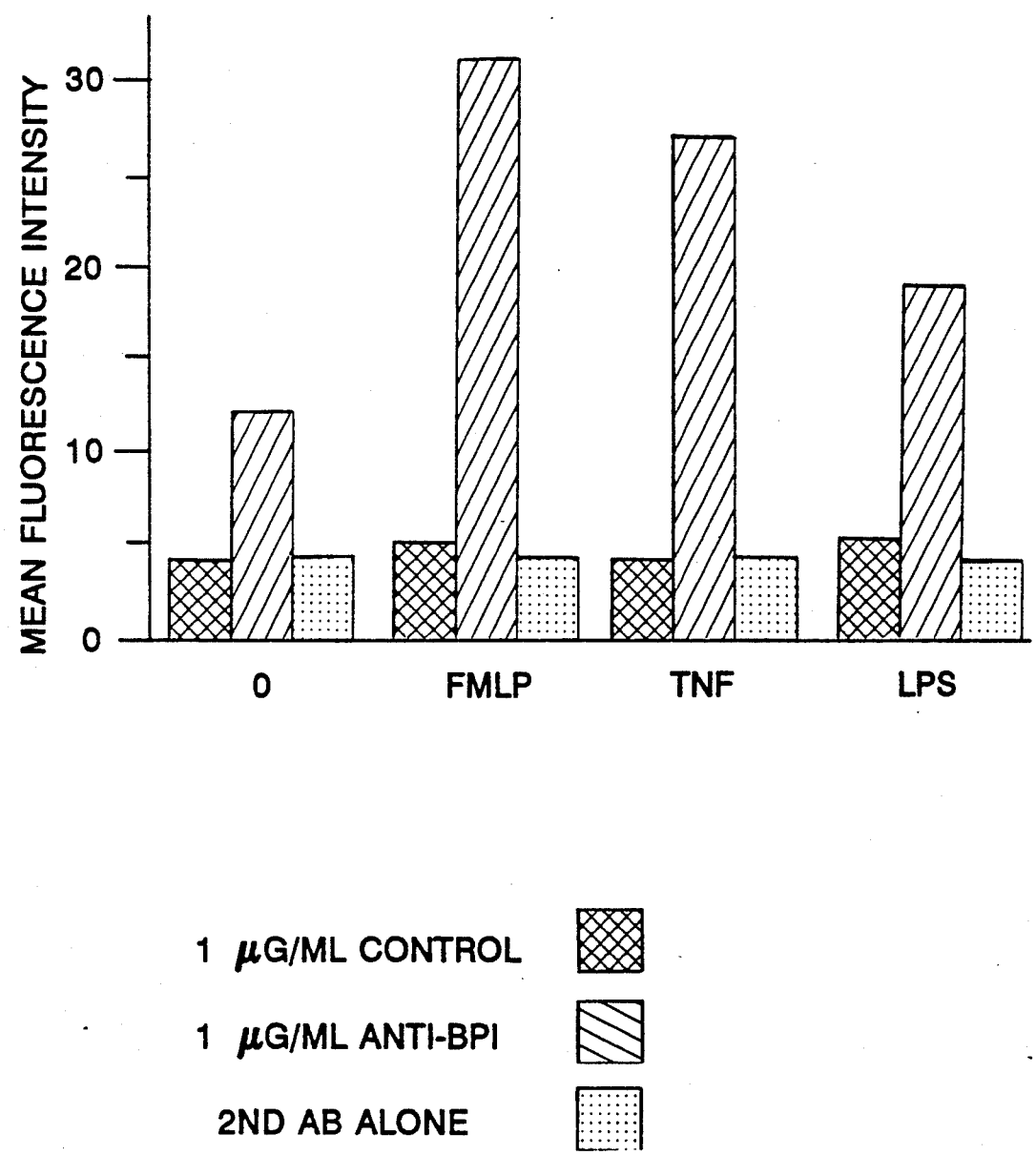
FIG. 5: (a). A bar graph illustrating BPI protein expression on the surface of neutrophils stimulated with FMLP, TNF, and LPS. (b) A bar graph illustrating maximal CR3 upregulation of human neutrophil cell surface expression.
Figure 5B:
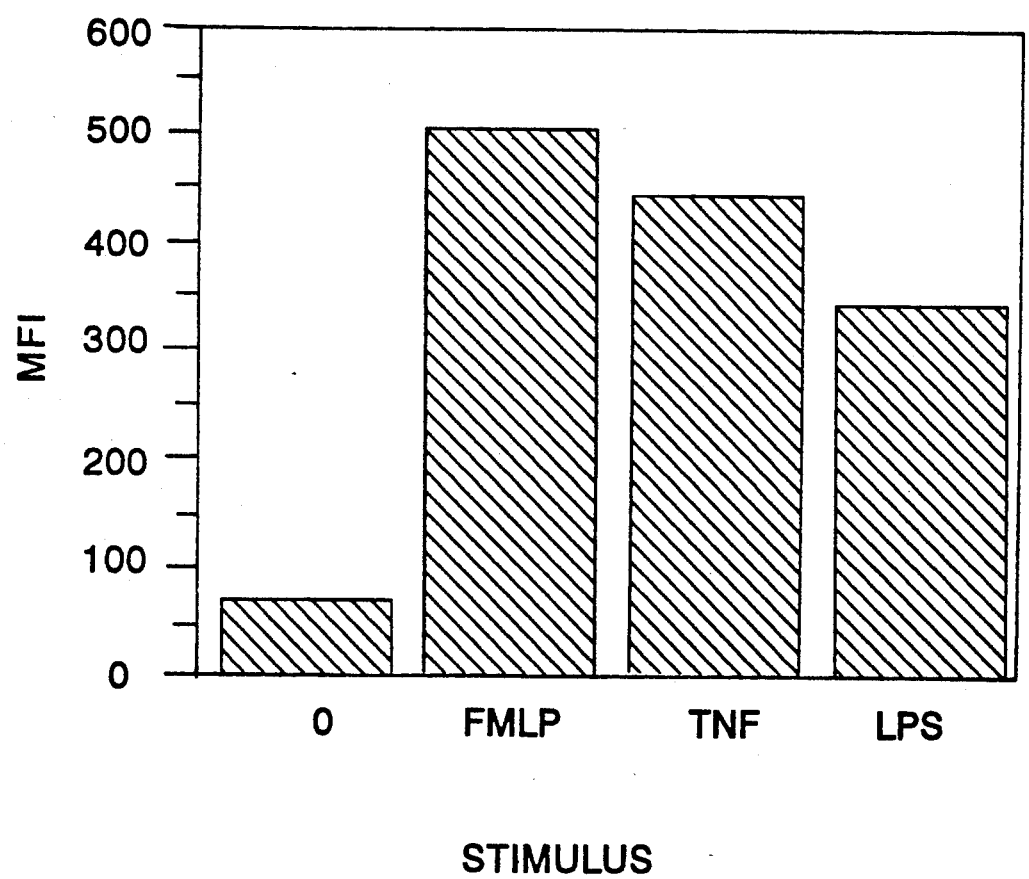

In response to LPS, human neutrophils upregulate cell surface expression of complement receptors CR1 and CR3 (FIGS. 1a and 5b). To measure this neutrophil response to LPS, we incubated freshly isolated human neutrophils with *E. coli* 0111:B4 LPS (FIG. 4a), and myxin B has been demonstrated to bind to LPS stoichiometrically (Morrison, D. C. and D. M. Jacobs, *Immunochem* 13: 813-818 (1976)). The calculated amount of PMB required to inhibit 10 ng/ml of smooth LPS is approximately 0.67 nM. In the subject experiments 0.4 ng/ml, or 0.36 nM of polymyxin B was required to completely inhibit neutrophil stimulation using 10 ng/ml of LPS. 90 ng/ml, or 1.58 nM BPI protein was required for 100% inhibition of 10 ng/ml LPS.

Therefore, on a molar basis the amount of BPI protein required to inhibit LPS stimulation of neutrophils vitro was approximately 4× the amount required for polymyxin B.

To test whether BPI protein can inhibit LPS from other gram negative organisms, LPS molecules with varying polysaccharide chain lengths and Lipid A were tested in the subject system against 90 ng/ml of purified BPI. Data shown in Table 2 demonstrates that although the stimulatory dose may vary between these molecules, LPS from both smooth and rough chemotypes as well as Lipid A are all inhibited by BPI.

TABLE 2

| LPS | 10 NG/ML | 1 NG/ML |
|---|---|---|
| E.COLI 0111:B4 | 97 | * |
| S. TYPHIMURIUM WILD TYPE | 103 | 113 |
| S. TYPHIMURIUM RE MUTANT | 113 | 109 |
| S. TYPHIMURIUM RE MUTANT LIPID A | 33 | 99 |
| P. AERUGINOSA | 112 | * |

*Low to no stimulation at this endotoxin concentration

BPI protein inhibits LPS-mediated neutrophil stimulation but not stimulation by either FMLP or TNF (Table 3). These data demonstrate that BPI protein inhibits LPS directly and does not disrupt neutrophil mechanisms involved in CR upregulation.

TABLE 3

Effect of BPI protein on Neutrophil Stimulation by Various Agents
Inhibition of CR Upregulation on Neutrophils

| Stimulus | Dose | % Inhibition CR1 | % Inhibition CR3 |
|---|---|---|---|
| LPS | 10 ng/ml | 109 | 102 |
| FMLP | $10^{-7}$ M | 9 | 11 |
| rTNF | 50 U/ml | 0 | 0 |

Figure 6:
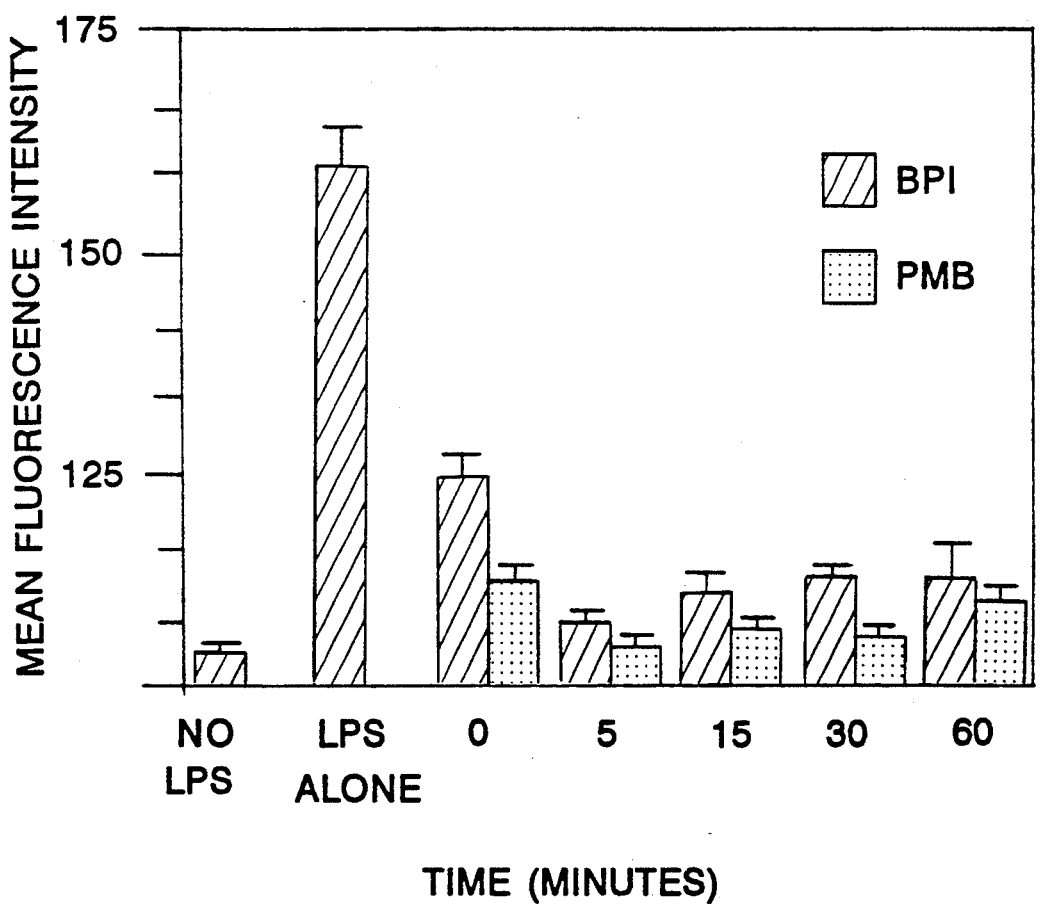
FIG. 6: A bar graph illustrating that BPI protein and polymyxin B inhibited more than 70% at time=0 of the neutrophil response to LPS.

Neutrophils were incubated with E. Coli 0111:B4 LPS, FMLP or TNF preincubated in the presence or absence of 2.7 nM BPI. Data is reported as percent inhibition of CR expression in response to each stimulus preincubated with buffer alone.
Neutralization of LPS by BPI protein occurred rapidly. Even without preincubation, both BPI protein (and polymyxin B) inhibited more than 70% of the neutrophil response to LPS (FIG. 6). Maximal inhibition was seen following only 5 minutes of preincubation.

BPI protein inhibits CR upregulation stimulated by LPS from smooth and rough bacterial strains, as well as lipid A (Table 4). Because of the broad range of BPI protein activity against these different forms of LPS, among which only lipid A and 2-keto-3-deoxy-octonate are shared determinants, it is likely that LPS inhibition by BPI protein is affected through lipid A.

TABLE 4

Inhibition of LPS and Lipid A induced Neutrophil Stimulation by BPI
Inhibition of CR Upregulation on Neutrophils

| Stimulus | Dose (ng/ml) | CR1 % Inhibition | CR3 % Inhibition |
|---|---|---|---|
| None | — | 0 | 0 |
| E. Coli 011:B4 LPS | 10 | 100 | 99 |
| S. typhimurium Wild Type LPS | 10 | 104 | 100 |
| S. typhimurium RE Mutant LPS | 1 | 97 | 95 |
| S. typhimurium RE Mutant Lipid A | 1 | 111 | 104 |

Neutrophils were stimulated with LPS and lipid A preincubated with and without 2.7 nM purified BPI. Results are expressed as percent inhibition of fluorescence intensity observed with each type of LPS alone.

Figure 7:
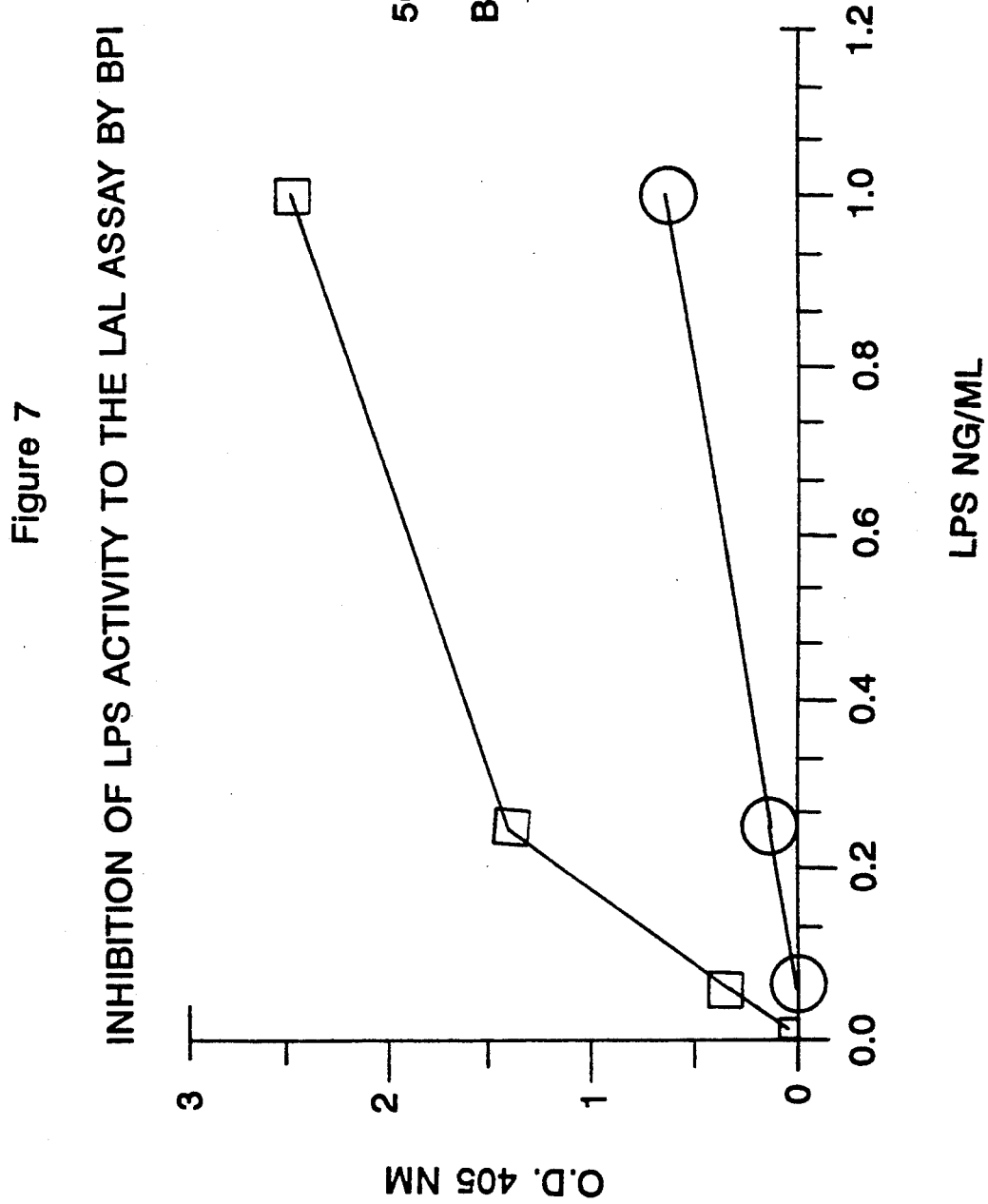
FIG. 7: A graph illustrating that BPI protein inhibits LPS activity on LAL assay.
Figure 8:
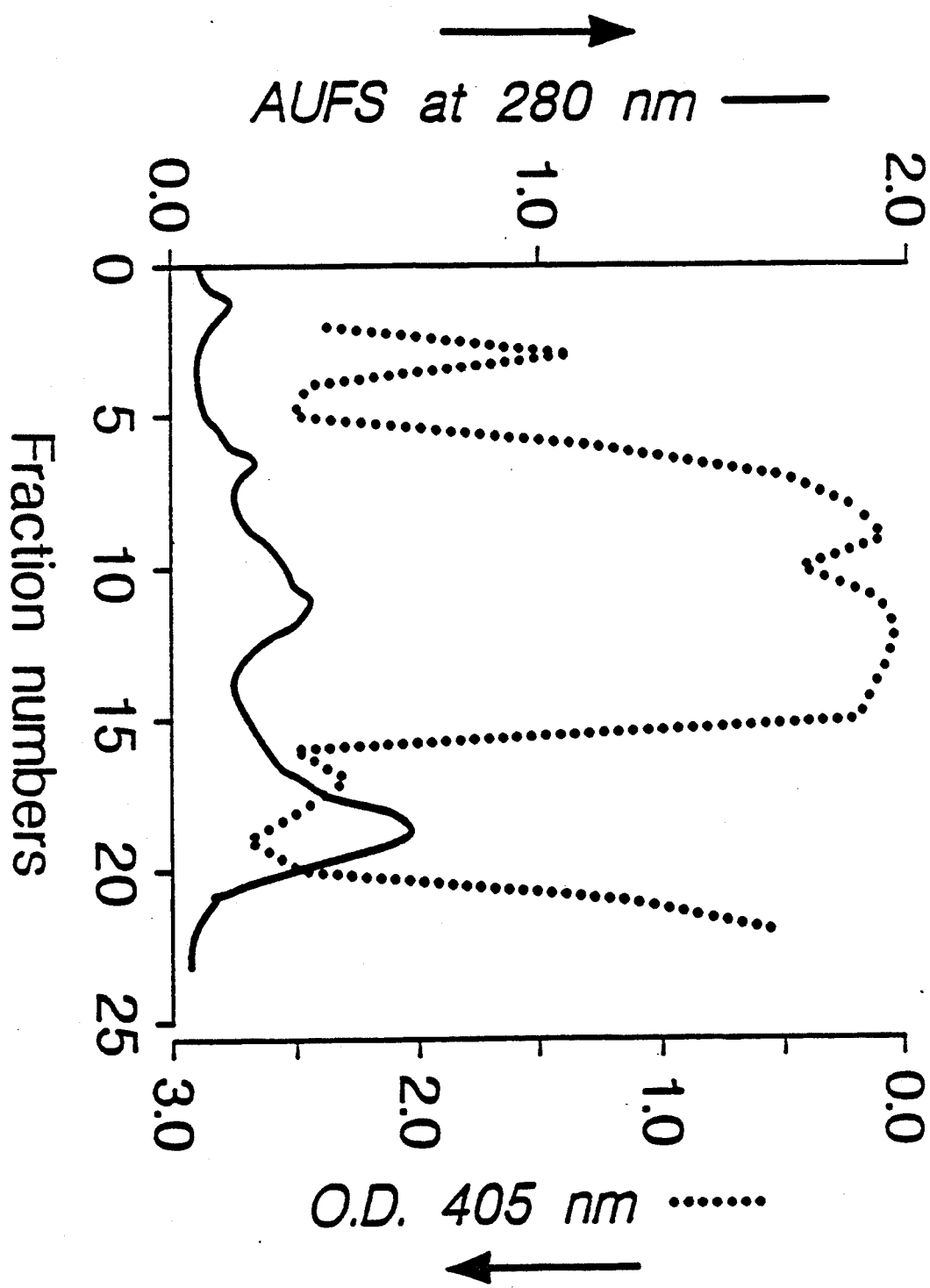
FIG. 8: A chromatogram showing a fractionated azurophile granule extract by cation exchange HPLC (step 1); the dotted line traces LPS inhibitory activity and the solid line traces protein absorbance.
Figure 9:
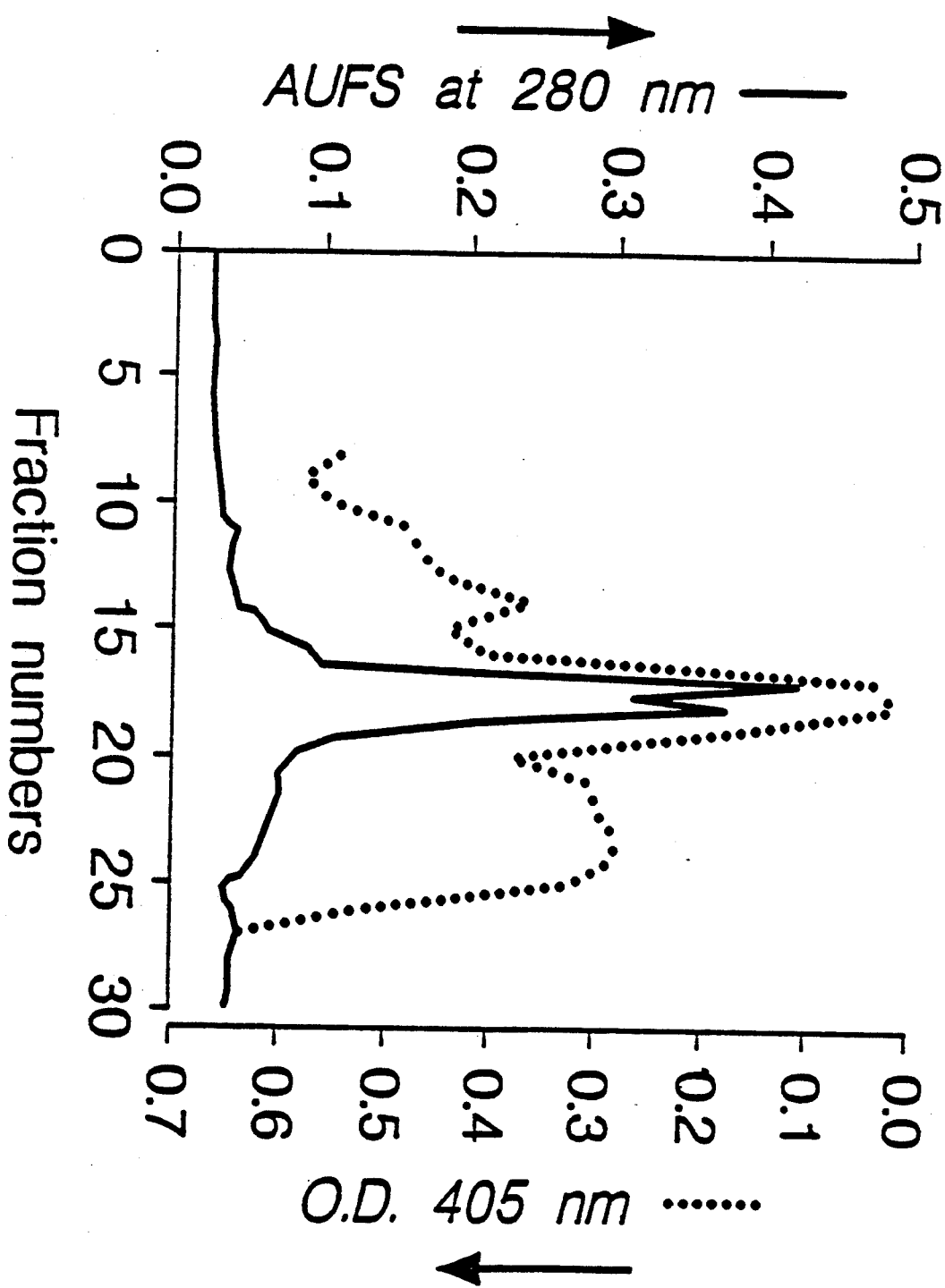
FIG. 9: A chromatogram showing a fractionated azurophile granule extract by cation exchange HPLC (step 2); the dotted line traces LPS inhibitory activity and the solid line traces protein absorbance.
Figure 10:
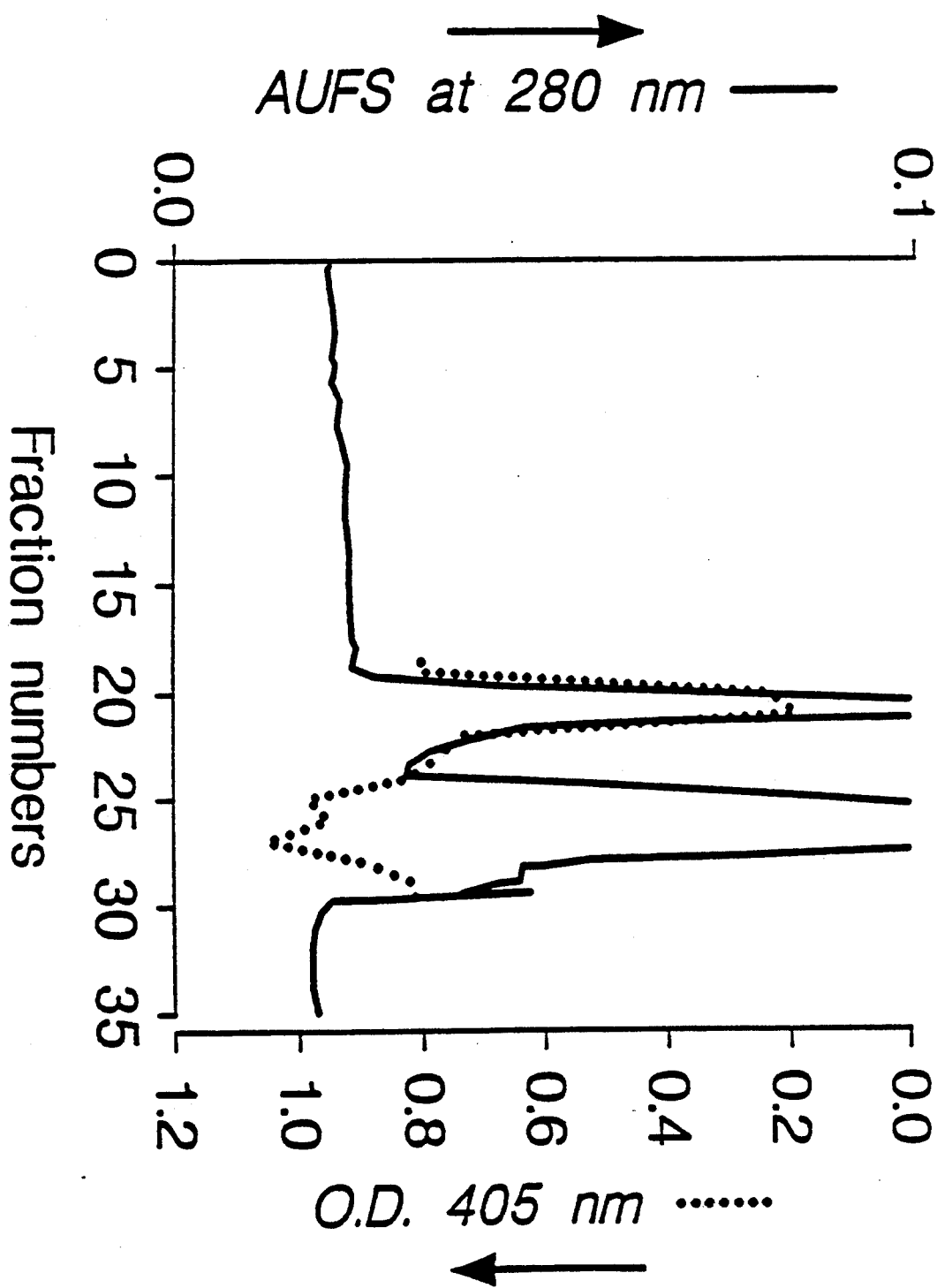
FIG. 10: A chromatogram showing a fractionated azurophile granule extract by size exclusion HPLC (step 3); the dotted line traces LPS inhibitory activity and the solid line traces protein absorbance.
Figure 11:
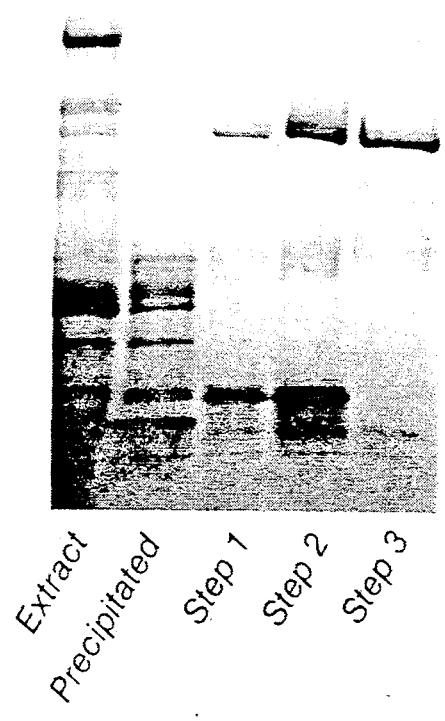
FIG. 11: An SDS-PAGE gel of the azurophil granule extract, the precipitated extract, and fraction pools from the three chromatographic steps.
Figure 12:
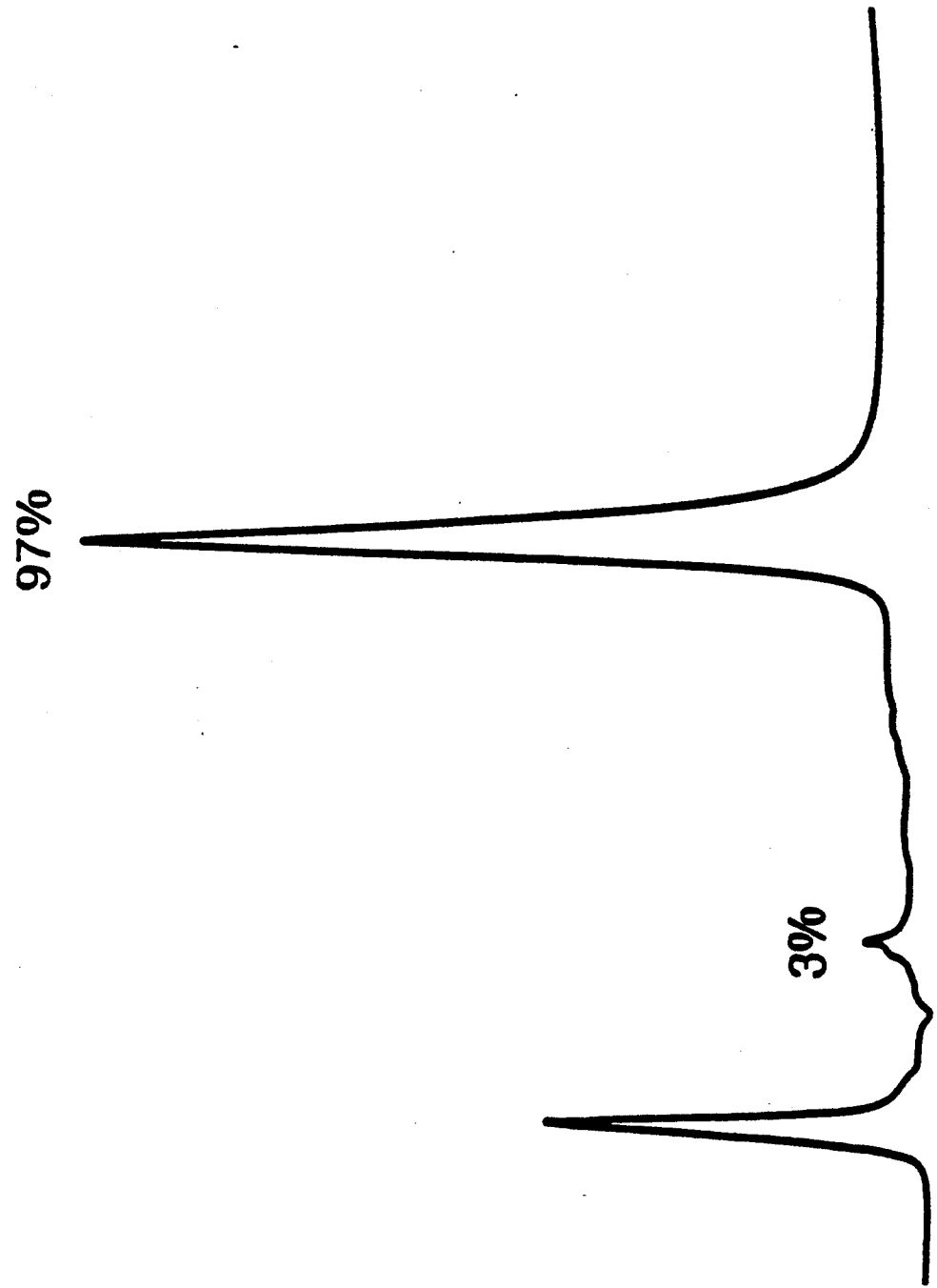
FIG. 12: Analysis of purified BPI protein by microbore reverse phase HPLC identifying a single major peak which accounts for 97% of the total protein.

BPI protein inhibits other LPS-mediated activities. At a concentration of approximately 9 nM, or 500 ng/ml, BPI protein significantly inhibited LPS activity in the LAL assay (FIG. 7). When LPS and BPI protein were added together without preincubation no inhibition was observed, indicating that BPI protein acted on LPS, and had no effect on the LAL assay system. BPI protein also inhibits LPS-mediated TNF production by human adherent mononuclear cells (Table 5).

TABLE 5

BPI protein Inhibits LPS-Induced TNF Production by Human Monocytes
TNF (pg/ml) Produced in Response to LPS Preincubated With*:

| LPS (ng/ml) | Medium Alone | 100 ng/ml Polymyxin B | 500 ng/ml Polymyxin B | 250 ng/ml BPI | Buffer BPI Control |
|---|---|---|---|---|---|
| 0 | 0 | 0 | 0 | 0 | 0 |
| 0.1 | 61 | 0 | 0 | 0 | 81 |
| 1 | 1051 | 96 | 0 | 0 | 1090 |
| 10 | 2053 | 2154 | 1490 | 1746 | 2325 |

*E. Coli 0111:B4 LPS, was preincubated with BPI protein or polymyxin B (PMB), than added to adherent peripheral blood mononuclear cells. TNF production was assayed by ELISA.

EXAMPLE 2

Materials and Methods

Immulon-2 96 well plates (Dynatech);
12-channel 50–200 μl pipettor;
P20, P200, P1000 pipettor;
Reagent reservoirs (Costar);
Racked 1 ml tubes (BioRad);
polypropylene 15 ml conical tubes.

REAGENTS FOR ELISA ASSAY

Solutions 25 mM Borate pH 9.5
Blocking solution=5% BSA ("Elisa grade") in PBS
Antibody diluent=1% BSA in PBS
Wash solution=1% BSA +0.05% Tween 20 in PBS
BPI protein standard (Lot 148104=104 μg/ml)
Standard and sample diluent=appropriate solution for unknown (e.g. if testing tissue culture supernatants, use REM+7.5% dFBS)
Substrate Buffer (recipe attached)
PNPP substrate tablets (5 mg/tablet: Sigma)

Antibodies

MM-1 IgG (4.9 mg/ml stock: use @3 μg/ml);
PIG8 SN (use @1:50);
Goat anti mouse IgG (BioRad) (use @1:2000).
I. ELISA PROTOCOL (FIG. 23)
  A. COAT 96-WELL PLATES WITH IgG (Note: Coat plates up to 1 month in advance. Store plates at 4° C. until needed.)
1. Dilute MM-1 IgG to 3 μg/ml in 25 mM Na Borate pH 9.5 (10 ml/plate);
2. add 100 μl MM-1 solution to each well of 96 well plate (Immulon-2);
3 incubate overnight at 37° C.; and
4. refrigerate until used.
  B. BLOCK 96-WELL PLATES WITH BSA
1. Flick MM-1 IgG from step A(1) hereinabove out of plates;
2. add 200 μl 5% BSA to each well;
3. incubate 2–4 hours 37° C.; and
4. wash plates 3× with wash solution and blot on paper towels.
  C. PREPARE BPI PROTEIN STANDARDS AND UNKNOWNS (Note: dilute BPI protein standards and unknowns in appropriate buffer for unknowns tested) at 100 ng/ml using the following protocol:

1. dilute 148104 BPI protein 1:100 (=1.4 μg/ml);
2. add 35.7 μl of 1.4 μg/ml solution to 464.3 μl (total vol.=0.5 ml)=100 ng/ml BPI protein "stock");
3. make 350 μl of each of the following standard concentrations as follows:

| μl of BPI 100 ng/ml | μl diluent | final [BPI] ng/ml |
|---|---|---|
| 140 | 210 | 40 |
| 105 | 245 | 30 |
| 70 | 280 | 20 |
| 35 | 315 | 10 |
| 28 | 322 | 8 |
| 17.5 | 332.5 | 5 |
| 7 | 343 | 2 |
| 0 | 350 | 0 |

4. add 100 μl standard (unknown)/well and incubate at RT for 2-4 hours, or overnight at 4° C.; and
5. wash plate 3×.

D. ATTACH AN ANTIBODY, I.E. P1G8, TO EACH WELL:
1. blot plate vigorously, after final wash, and add 100 μl of P1G8 supernatant at 1:50 (=200 μl in 10 ml of 1% BSA in PBS) to each well;
2. incubate at 37° C. for 1 hour; and
3. wash plate 3×.

E. ATTACH A REPORTER ANTIBODY TO ANTIBODY HEREINABOVE, I.E. P1G8, TO EACH WELL:
1. blot plate vigorously after final wash, i.e. D(3) hereinabove, and add 100 μl 1:2000 (=5 μl in 10 ml) goat-anti-mouse IgG- Alkaline Phosphate conjugate to each well;
2. incubate at 37° C. for 30 minutes; and
3. wash 3×.

F. PREPARE SUBSTRATE (Note: Make substrate up just before adding to plate):
1. blot plate vigorously after final wash, i.e. E(3) hereinabove, and add 100 μl substrate solution (see reagents); and
2. read plate at 405 nm using a spectrophotometer. Use quadratic fit. Keep plate in the dark between readings.

EXAMPLE 3

Purification of BPI Protein Under Rigorously Pyrogen-free Conditions

Materials and Methods

Reagents USP grade sterile irrigation water was obtained from Travenol Laboratories Inc., Deerfield Ill.; Pyrosart filters from Sartorius GmbH, W. Germany; CM Sepharose FF from Pharmacia, Upsala, Sweden; Polyaspartamide weak cation exchange HPLC column (100×4.6 mm) from the Nest Group, Southborough Mass.; Glycine and Bio-Sil G250 size exclusion HPLC column (600×7.5 mm) from Bio-Rad Laboratories, Richmond, Calif.; Polyacrylamide electrophoresis gels from Novex, Encitas, Calif.; Sequencing and amino acid analysis reagents and buffers from Applied Biosystems Inc., Foster City, Calif.; Trifluoroacetic acid, constant boiling HCL, hydrolyzate amino acid standard, and BCA protein assay reagents from Pierce Chemical Co., Rockford, Ill.; Limulus Amebocyte Lysate assay from Whittaker Bioproducts, Inc., Walkersville, Md.; Lipopolysaccharide from RIBI Immunochem Research, Inc., Hamilton, Mont.; HPLC grade Acetonitrile from J. T. Baker, Phillipsburg, N.J.; all other buffers and salts used were reagent grade. 18 megohm purity water was prepared by Lab Five ultrapure water system from Technic, Seattle, Wash. 0.5M NaOH for sanitization was prepared from reagent grade NaOH pellets and USP water.

Granule extracts from Neutrophils: were prepared as described (U.S. Ser. No. 199,206, filed May 26, 1988) except that the percoll separation of azurophil granules was omitted. Instead, whole granule fractions were obtained by centrifuging the post nuclear supernatant at 17,000 g for 20 minutes. The granule pellet was then suspended in a volume of 1 ml of 50 mM glycine pH 2 for every $4\times10^8$ cells lysed. Resuspended granules were lysed by five freeze/thaw cycles on dry ice ethanol followed by vigorous agitation for one hour at 4 degrees C. The soluble extract was obtained by centrifugation at 30,000g for 30 minutes.

Limulus Amebocyte Lysate assay: was performed as directed by the manufacturer. Where necessary the pH of samples was adjusted to neutrality by the addition of pyrogen free 0.5M phosphate buffer pH 7.4. and salinity was decreased to <150 mM by dilution with USP water (Desch, C. E., et al. (1989) *Infection and Immunity*, 57:1612-1614; Friberger, P. (1985) The design of a reliable endotoxin test. p. 139-149. In J. W. Cape (ed.). Bacterial endotoxins: structure, biomedical significance and direction with the Limulus amebocyte lysate test. Alan R. Liss, Inc., New York; Galanos, C., et al. (1979) Chemical, physiochemical and biologic properties of bacterial lipopolysaccharides, p. 321-332. In E. Cohen (ed.) Biomedical application of the horseshoe crab (Limulidae). Alan R. Liss, Inc., New York; Byaston, K. F. and J. Cohen (1990) *J. Med. Microbiol.*, 31:73-83; Tanaka, D., et al. (1982) *Biochem. Biophys. Res. Comm.*, 105:717-723; Morita, T., et al. (1985) *J. Biochem.*, 97:1611-1620).

LPS inhibition assay: was performed as previously described (M. Marra et al. (1990) *J. Immunol.* 144(2):662-666).

High salt fractionation of granule extracts: 200 mgs of extracted protein were pooled from various preparations and kept on ice. 1 volume of sterile 5M NaCl was added for every 4 volumes of extract. The resulting precipitate was pelleted by centrifugation at 20,000 g for 20 minutes at 4° C. This supernatant was prepared for CM sepharose chromatography by diluting with 4 volumes of USP irrigation water and adjusting the pH with enough 1M Tris pH 7.4 to give a final concentration of 50 mM. Only fresh, sterile, pyrogen free stock salts and buffers were used.

CM Sepharose chromatography: An XK-16 column (Pharmacia) was packed with sufficient resin to give a bed volume of 5 mls. The column was installed on a gradient FPLC equipped with a P1 pump for sample loading. Prior to use, all surfaces in contact with the mobile phase were extensively washed with 0.5M NaOH. The column was sanitized by washing at 0.2 mls/min. with 0.5M NaOH for 4 hrs. The column was then re-equilibrated and a blank run was performed. Fractions from the blank run and eluents were tested by LAL assay for pyrogenicity (Desch, C. E., et al. (1989) *Infection and Immunity*, 57:1612-1614; Friberger, P. (1985) The design of a reliable endotoxin test. p. 139-149. In J. W. Cape (ed.). Bacterial endotoxins: structure, biomedical significance and direction with the Limulus amebocyte lysate test. Alan R. Liss, Inc., New York; Galanos, C., et al. (1979) Chemical, physiochemical and biologic properties of bacterial lipopolysacchrides, p. 321-332. In E. Cohen (ed.) Biomedical application of the horseshoe crab (Limulidae). Alan R. Liss, Inc., New York; Byaston, K. F. and J. Cohen (1990) *J. Med. Microbiol.*, 31:73-83; Tanaka, D., et al. (1982) *Biochem. Biophys. Res. Comm.*, 105:717-723; Morita, T., et al. (1985) *J. Biochem.*, 97:1611-1620. Prepared extract was loaded at a flow rate of 400 mls/hr. Once loaded the column was washed with 2 to 3 column volumes of starting buffer. The granule extract was kept on ice during loading. The column was run at room temperature.

Weak cation exchange HPLC: was performed using an Eldex ternary gradient pump equipped with a Rheodyne injector and a Gilson model 111B U.V. detector. Wettable surfaces were washed with 0.5M NaOH followed by extensive rinsing with USP water to remove all traces of base prior to installing the column. Blank fractions and eluents were tested for pyrogenicity as above.

Gel permeation HPLC: was performed with the same precautions and equipment outlined for weak cation exchange HPLC.

Polyacrylamide gel electrophoresis: 8 to 16% acrylamide gradient gels were purchased from Novex and run according to the manufacturers specifications.

Protein sequence determination: An Applied Biosystems 477A pulsed liquid phase sequenator equipped with a 120A PTH amino acid analyzer was used for automated edmund degradation.

Microbore reverse phase HPLC: Material for protein sequencing was prepared by desalting on a 30×2.1 mm Aquapore butyl column. The gradient used was 30 to 100% B in 30 minutes at a flow rate of 200 ml/minute. Detector settings were 214 nm wavelength at 2.0 absorbance units full scale (see insert FIG. X). An HP 3396A was used to integrate and plot data.

Amino Acid Analysis: was performed on the system described above using the PTC column, buffers and separation conditions provided by ABI. Sample hydrolysis and PTC derivatives were prepared using a Pico-Tag workstation from the Waters chromatography division of Millipore using the manufacturer's protocols.

Protein assays: Protein concentrations were determined using BCA method instructions 23230, 23225 from Peirce Chemical Co. In order to minimize buffer interference, samples were diluted 10 fold and the micro reagent protocol was used.

Results

Purification of LPS neutralizing activity was enhanced by the observation that high concentrations of NaCl (1M) caused the reversible precipitation of about ninety percent of the protein present in the granule extract. Essentially all of the LPS inhibitory activity remained in the soluble supernatant. The soluble fraction was then diluted, to reduce the ionic strength, and further purified and concentrated by CM sepharose cation exchange chromatography. A broad peak of activity eluted which was subsequently further purified using a polyaspartamide high performance cation exchange column. A somewhat sharper peak of activity was recovered which co-migrated with a major protein of about 55,000 molecular weight by SDS-PAGE along with several lower molecular weight proteins. Gel permeation HPLC was used as the final purification step and identified a peak of activity which eluted with a single sharp protein peak. Purified BPI migrated as two closely spaced bands on SDS-PAGE at 55,000 molecular weight. 25% of the total endotoxin neutralizing activity was recovered with a 250 fold purification.

The purified BPI was subjected to reverse phase HPLC followed by N-terminal sequence analysis by automated Edman degradation. The sequence, shown in FIG. 6 was identified as bacterial permeability increasing protein by virtue of complete homology through 39 residues. In addition the amino acid composition of the purified molecule was virtually identical to that of BPI protein.

To investigate whether both closely spaced bands represented BPI protein the purified proteins were subjected to western blotting analysis using BPI-specific rabbit polyclonal antisera raised against a synthetic peptide comprising amino acids 1-20 of BPI. Both bands were immunoreactive. The differences likely arise from glycoslyation.

EXAMPLE 4

LPS inhibitory activities of purified endotoxin free BPI protein in vitro

Figure 13:
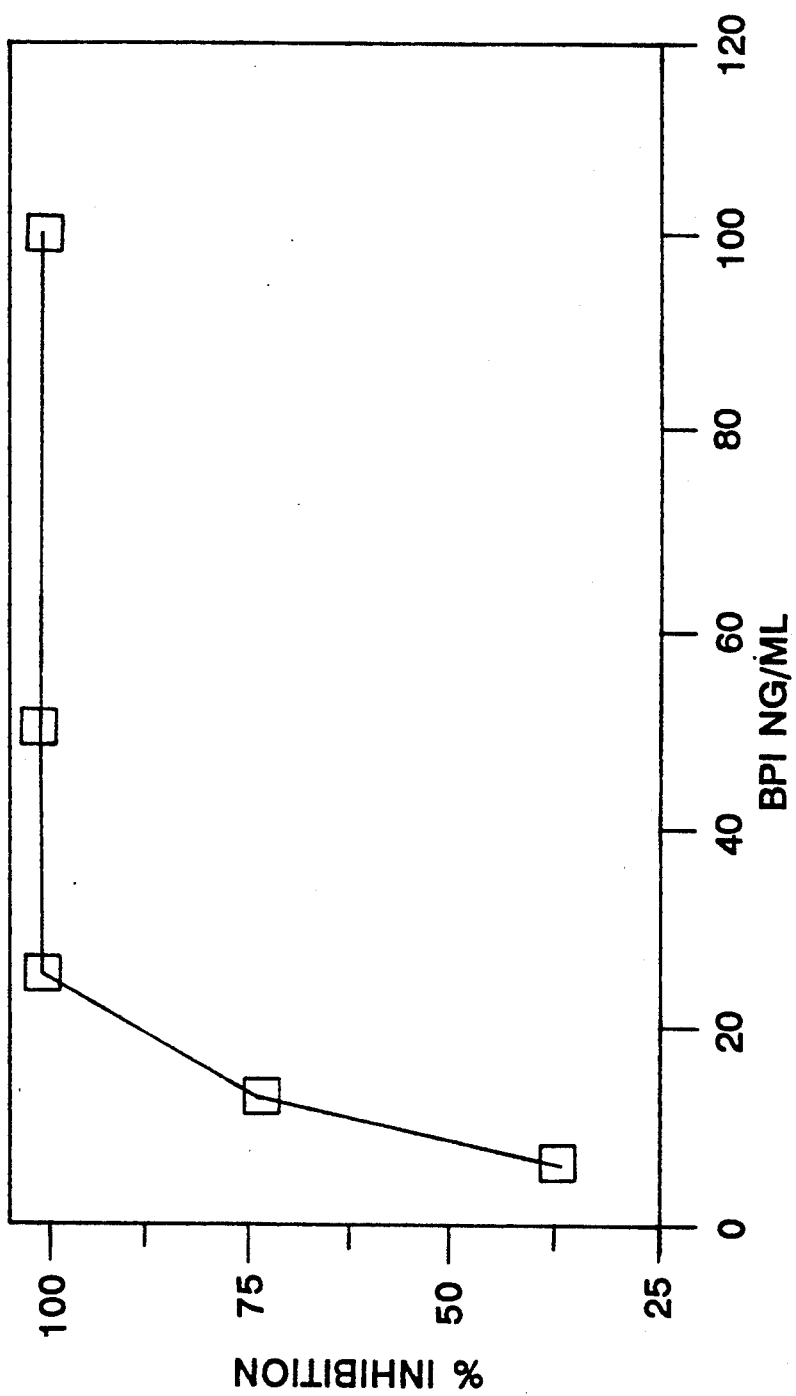
FIG. 13: A line graph illustrating inhibition of the neutrophil response to 10 ng/ml LPS by BPI.

Purification of BPI protein under rigorously pyrogen-free conditions, as described in example 3 resulted in a more potent BPI protein preparation as shown by the dose response curve in FIG. 13. Inhibition of LPS-mediated CR upregulation was complete at 25 ng/ml BPI, representing a 4-fold increase in activity compared to the material used in section I. On a molar basis this BPI protein preparation inhibited LPS at approximately stoichiometric proportions, equivalent to molar inhibitory concentrations of polymyxin B. BPI protein also inhibited LPS-mediated TNF production by human adherent mononuclear cells at a lower concentration following purification under pyrogen-free conditions (Tables 7 and 8).

Figure 16:
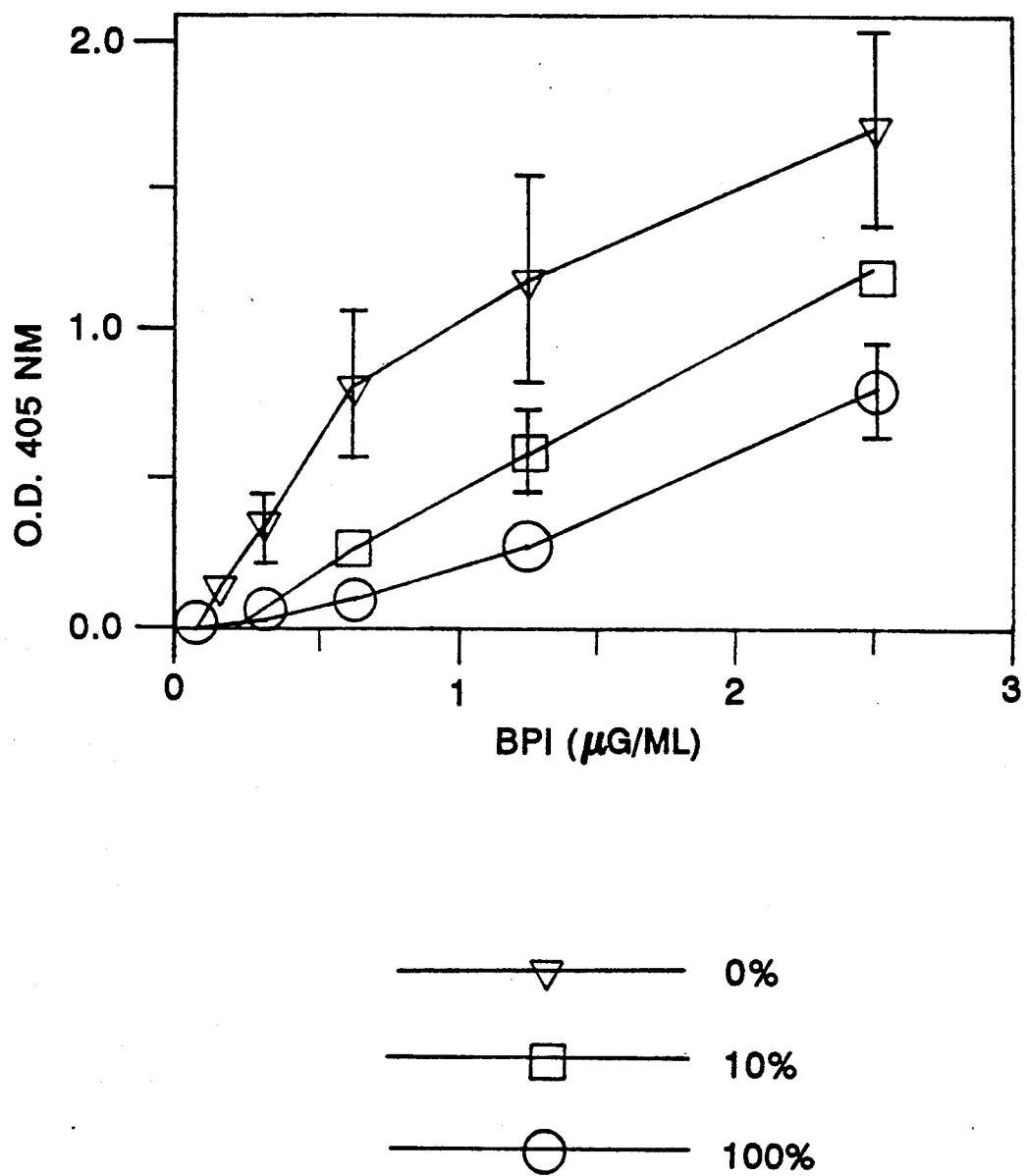
FIG. 16: A line graph showing that BPI protein binds to LPS in the presence of plasma.
Figure 17:
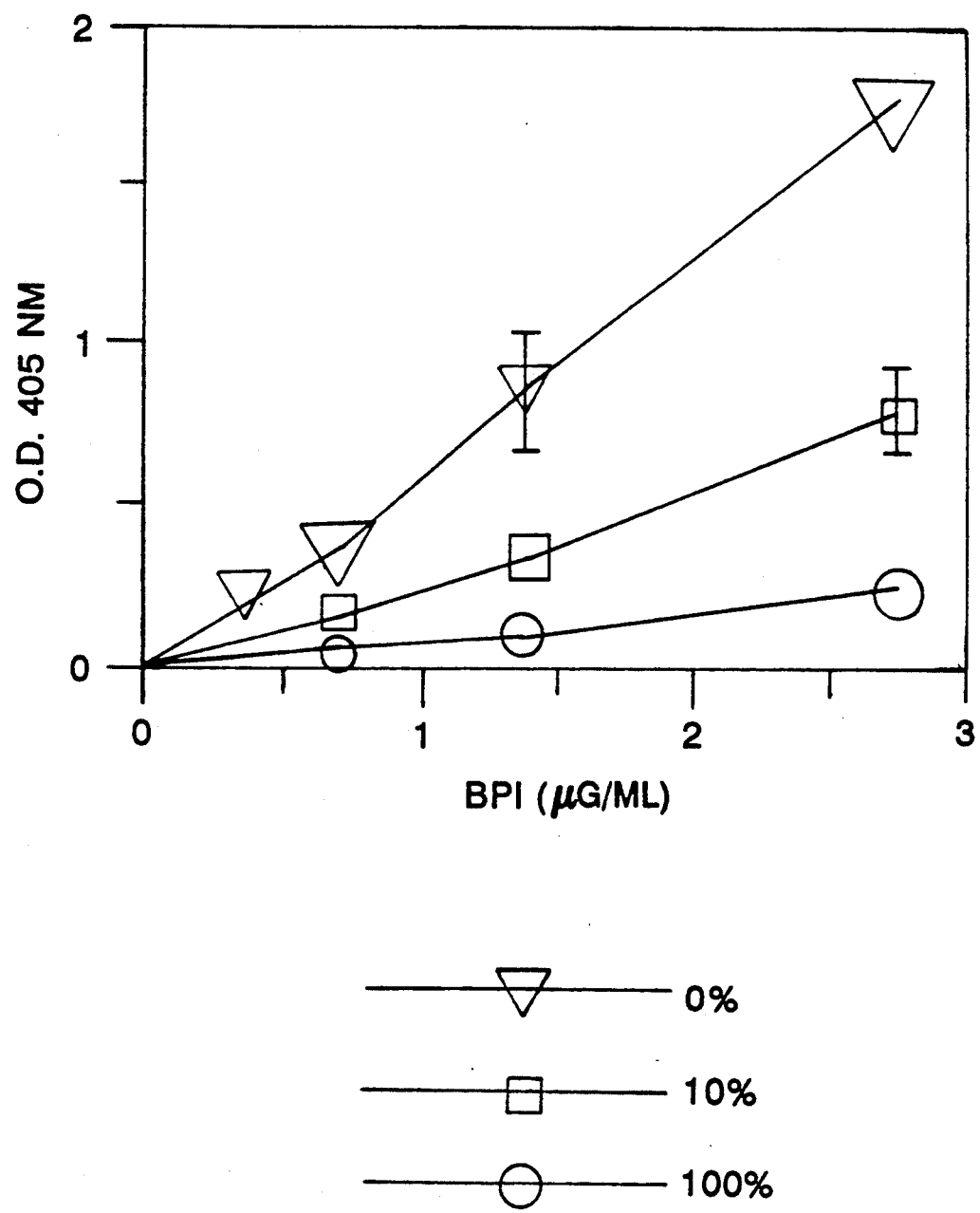
FIG. 17: A line graph showing BPI protein binds to LPS in the presence of serum.

BPI protein binds to LPS (FIG. 14). In these experiments, 4 μg of LPS/well was immobilized on 96 well plastic plates, then incubated with varying concentrations of BPI, and developed with anti-BPI protein polyclonal antisera. BPI protein binding to LPS was inhibited by polymyxin B (FIG. 15), demonstrating specificity of BPI protein binding. BPI protein binds to LPS in the presence of both plasma (FIG. 16) and serum (FIG. 17), demonstrating potential in vivo efficacy of BPI.

TABLE 7

BPI protein Inhibits LPS-Induced TNF Production by Human Monocytes
TNF (pg/ml) Produced in Response to LPS Preincubated with*:

| LPS ng/ml | Medium alone | 100 ng/ml PMB | 400 ng/ml BPI | 150 ng/ml BPI | 25 ng/ml BPI | Buffer Control |
|---|---|---|---|---|---|---|
| 0 | 0 | 0 | 0 | 0 | 0 | 0 |
| 0.1 | 98 | 79 | 0 | 0 | 0 | 269 |
| 1 | 1150 | 1207 | 0 | 0 | 0 | 1292 |
| 10 | 1370 | 1270 | 145 | 353 | 559 | 1413 |

*E. Coli 0111.B4 LPS. was preincubated with BPI protein or polymyxin B (PMB), then added to adherent peripheral blood mononuclear cells. TNF production was assayed by ELISA.

TABLE 8

INHIBITION OF LSP-INDUCED TNF PRODUCTION BY HUMAN MONOCYTES

TNF (pg/ml) Produced in Response to LPS Preincubated with*:

| LPS | 1000 ng/ml Polymyxin B | 100 ng/ml Polymyxin B | 250 ng/ml BPI | 50 ng/ml BPI | 10 ng/ml BPI | Buffer Control |
|---|---|---|---|---|---|---|
| 10 | 333 ± 18 | 601 ± 257 | 270 ± 67 | 270 ± 67 | 436 ± 38 | 697 ± 37 |
| 100 | 769 ± 101 | 1140 ± 73 | 834 ± 30 | 686 ± 84 | 1005 ± 50 | 892 ± 47 |
| 1000 | 844 ± 144 | 1016 ± 20 | 1130 ± 10 | 778 ± 189 | 1025 ± 71 | 723 ± 88 |
| S. aureus | 1685 ± 121 | 1541 ± 397 | 1558 ± 139 | 1268 ± 374 | 1554 ± 324 | 1423 ± 447 |

*BPI protein or polymyxin B sulfate were preincubated with 0–10 ng/ml E. Coli 0111:B4 LPS or 0.1% w/v killed S. aureus then added adherent peripheral blood mononuclear cells. TNF production was assayed by ELISA.

EXAMPLE 5

BPI/Endotoxin Pyrogenicity

Stage IA—Pyrogenicity of Glycine Buffer

305 μl of Glycine Buffer control (Supplied by Redwood City) was diluted to 7 ml in PBS (Redwood City) and mixed in polypropylene tubes (pyrogen-free). The tube was labeled with notebook #1990 and tested in a three rabbit USP Rabbit Pyrogen assay at a dose of 2 ml/rabbit (actual injection dose was 2.1 ml/rabbit).

The product was non-pyrogenic; it produced a total temperature rise for all three rabbit of 0.4 C.

State IB—Pyrogenicity of 2 μg of BPI

304 μl of BPI protein (Lot 78038, dated Aug. 19, 1989) was diluted to 7 ml using PBS (Redwood City) and mixed in polypropylene tubes (pyrogen-free). The Tube was labeled with notebook #20170 and tested in a three rabbit USP Pyrogen assay at a dose of 2.0 ml/rabbit.

The product was non-pyrogenic as demonstrated by a total temperature rise of 0.2° C.

Stage II—Pyrogenicity of BPI protein pre-incubated with endotoxin

Endotoxin from E. coli 055.B5 (Sigma Chemicals) was diluted in PBS (Redwood City) to 4096 EU/ml. This concentration was confirmed by the LAL Assay.

304 μl of BPI protein (Lot 78038, dated Aug. 19, 1989) was diluted to 7 ml with the PBS diluted endotoxin (4096 EU/ml) hereinabove using polypropylene tubes. The tube was mixed by vortexing to effect mixing. The BPI+Endotoxin and Endotoxin in PBS were incubated at 37° C. in a water bath for 30 minutes. Following incubation at 37° C. the BPI+Endotoxin showed an endotoxin concentration of 122 EU/ml. The endotoxin diluted in PBS did not show a change in the end point of 4096 EU/ml.

The BPI+Endotoxin and Endotoxin in PBS in PBS were tested in the three rabbit USP pyrogen assay. Endotoxin+BPI was significantly less pyrogenic then endotoxin alone with a total temperature rise of 4.6° C. and 7.5° C., respectively.

Stage II (Repeat)

To further investigate the inhibitory effects of BPI we increased the ratio of BPI to endotoxin, using the Official FDA Reference endotoxin.

A vial of EC-5 was rehydrated with PBS (Redwood City) to 2 ml to give a concentration of 5000 EU/ml. We verified by the label claim of 10,000 EU/ml by LAL assay.

The BPI+Endotoxin sample was prepared by adding 38 μl of BPI protein (Lot 78038) to 7.3 ml of PBS plus 320 μl of the 5000 EU/ml of EC-5 endotoxin. The preparation was mixed in a polypropylene tube(pyrogen-freed) and mixed well. An 8.0 ml sample of EC-5 endotoxin was prepared in PBS (Invitron Corporation, Redwood City) to the same concentration without the addition of BPI. Both samples was incubated at 37 C for 30 minutes in a water bath.

Figure 18:
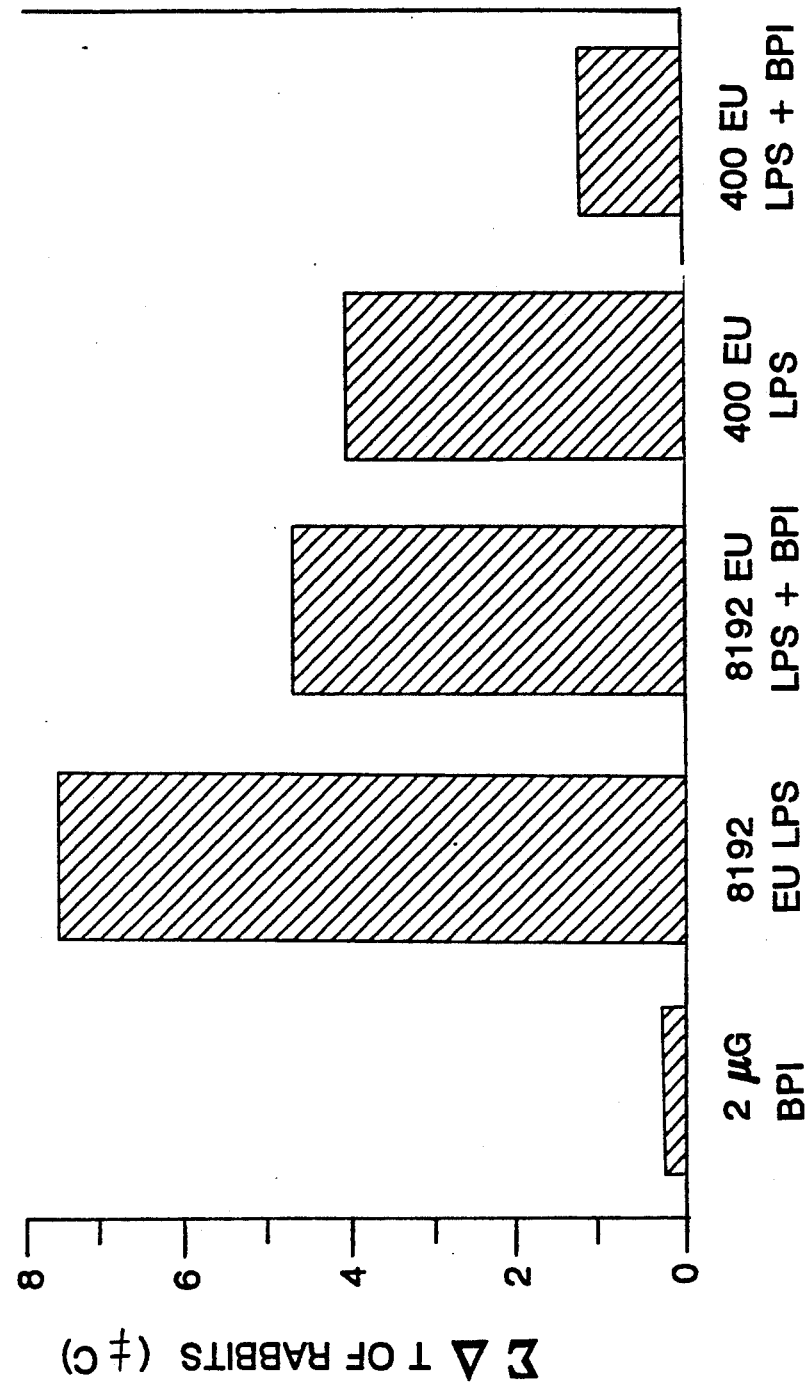
FIG. 18: A bar graph showing that BPI protein modulates pyrogenic response to LPS.
Figure 19:
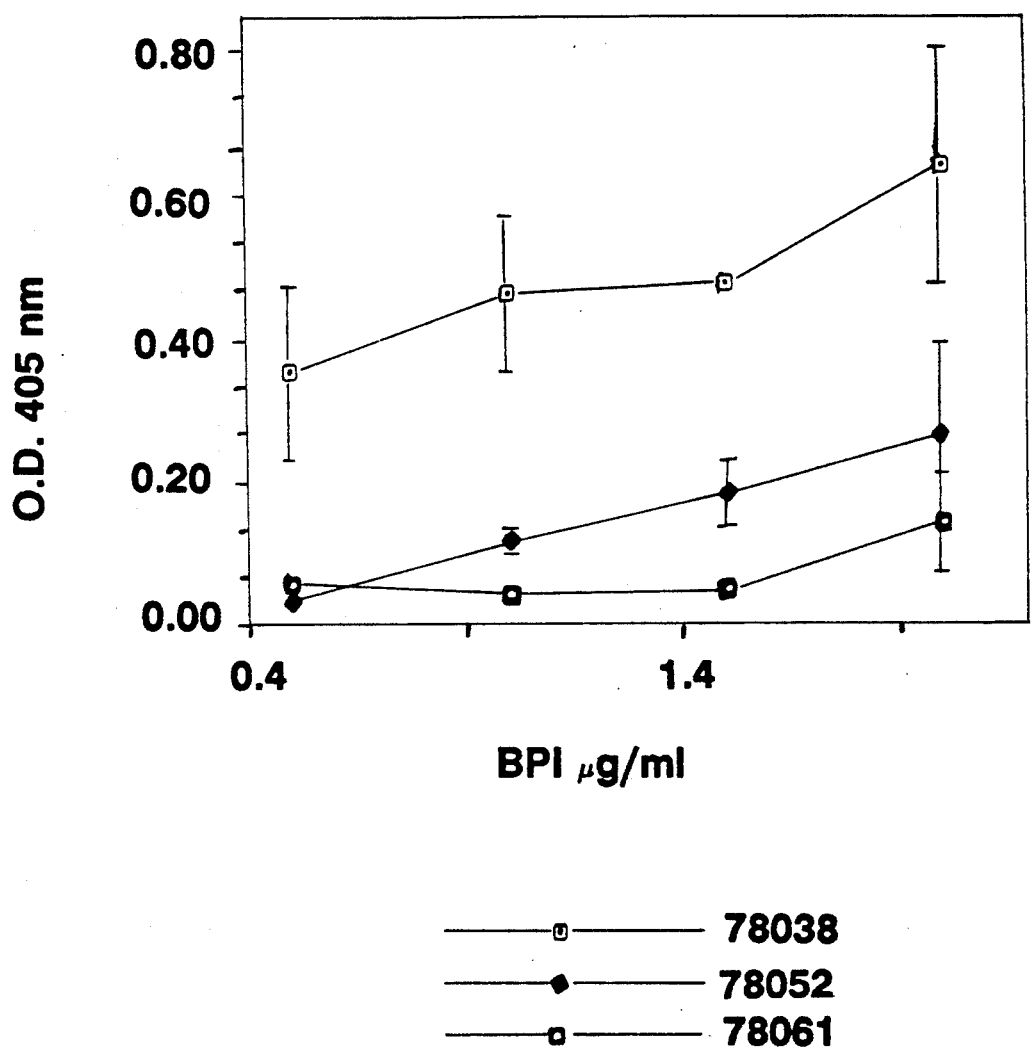
FIG. 19: A line graph showing data from "LPS binding 64." Protocol is as follows: Glycolipid from *S. typhumurium* RE mutant (4 μg/well) was immobilized on 96 well microtiter plates (Immulon 2, Dynatech Inc.) as previously described ( ). Wells were blocked with 200 μl low endotoxin BSA (Miles) for 2 hours at 37 μC, washed three times in pyrogen free PBS+1 mg/ml low endotoxin BSA (PF-PBS/BSA), and incubated with varying concentrations of BPI protein diluted in plasma or PF-PBS/BSA.
Figure 20A:
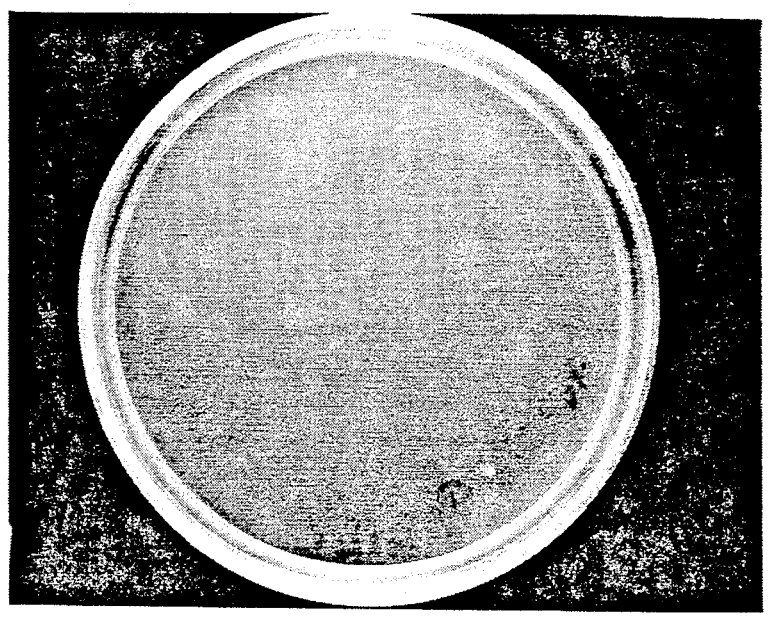
Figure 20B:
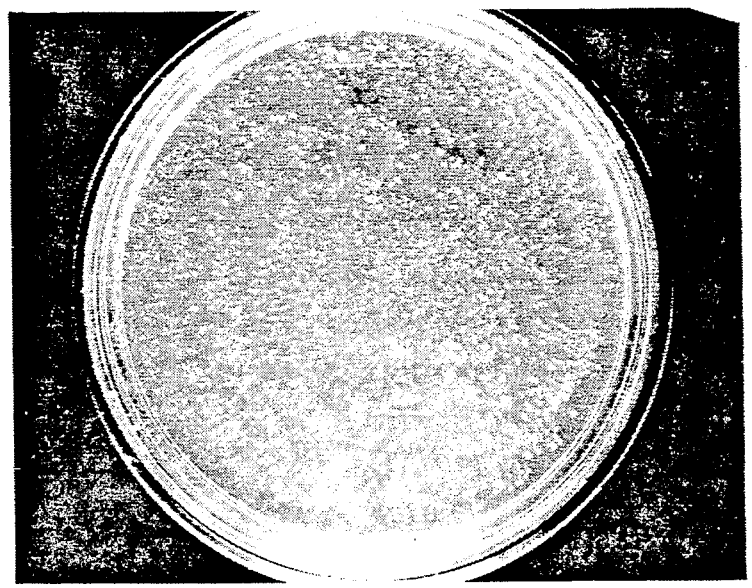
Figure 20C:
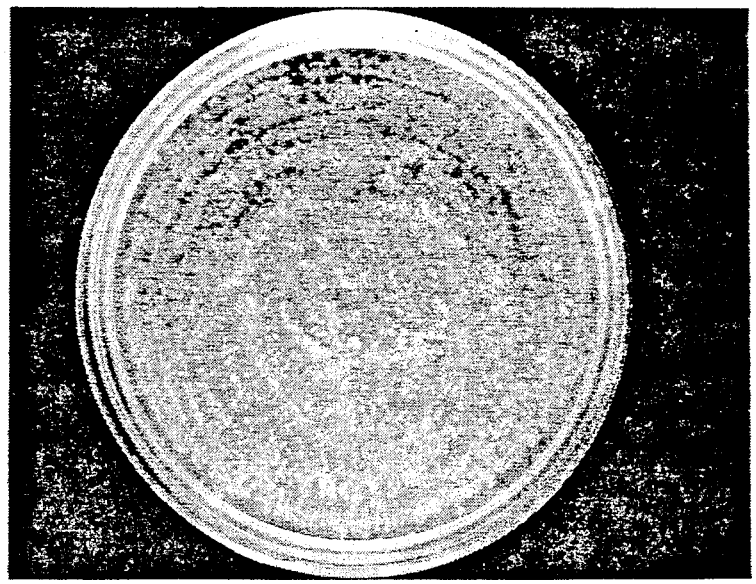
Figure 20D:
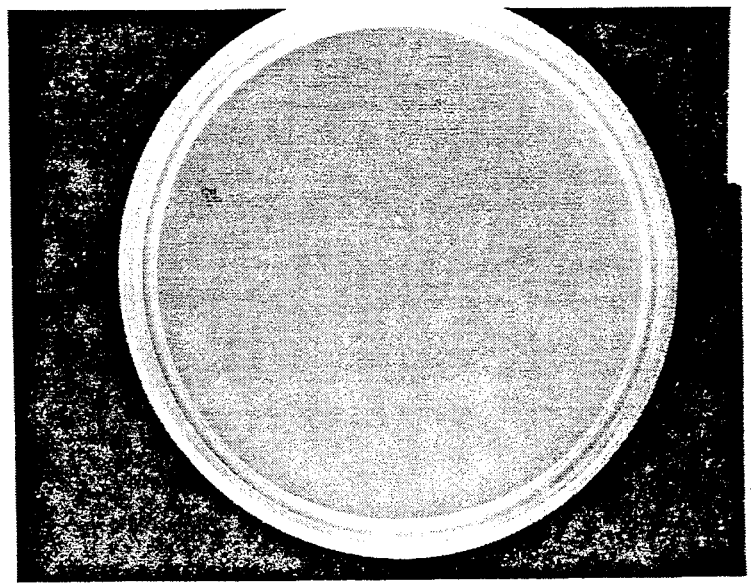
Figure 20E:
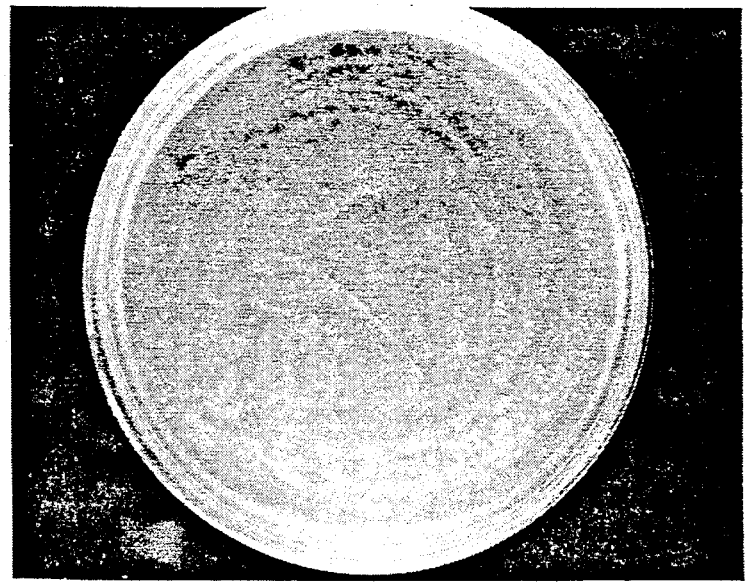

The two samples were tested for endotoxin activity using the LAL assay. The BPI+Endotoxin was negative. The endotoxin sample was positive at the target of 200 EU/ml (FIG. 18).

Both samples were tested in the three rabbit USP Pyrogen Assay at a dose of 2.0 ml/rabbit.

The BPI+Endotoxin was non-pyrogenic and caused a total temperature rise of only 1.1° C. The EC-5 endotoxin in PBS was pyrogenic and caused a total temperature rise of 3.9° C. Thus BPI blocks the pyrogenic response to endotoxin in vivo.

EXAMPLE 6

Inhibition of LPS-induced TNF Production by BPI

Human peripheral blood mononuclear cells were isolated on Ficoll-Paque (Pharmacia) gradients, washed 2× in pyrogen free HBSS (Hazelton), and resuspended at 5×10⁶/ml in RPMI (Gibco) media without serum. Two hundred μl of this cell suspension was incubated in each well of flat-bottom 96 well tissue culture dishes (Costar) for 2 hours at 37° C. Nonadherent cells were removed by washing 2× with RPMI+10% autologous heat inactivated serum. Adherent mononuclear cells were stimulated with E. coli 0111:B4 LPS which had been preincubated for 30 minutes at 37° C. with buffer, BPI protein or polymyxin B (Gibco; 7900 U/ml). Supernatants were harvested four hours after LPS mixtures were added. Secretion of TNFα was quantitated by ELISA (Endogen) (results at Table 9).

TABLE 9

| BP(nM): | 10 ng/ml LPS | | | | ng/ml LPS | | | | 0 LPS |
|---|---|---|---|---|---|---|---|---|---|
| | 0 | 7.3 | 1.4 | 0.3 | 0 | 7.3 | 1.4 | 0.3 | |
| 78038n | 626 | 129 | 159 | 203 | 334 | 153 | 187 | 165 | 113 |
| 148104n | | 98 | 104 | 162 | | 98 | 119 | 162 | |
| 148113n | | 92 | 114 | 151 | | 71 | 129 | 155 | |
| 148159r | | 82 | 158 | 155 | | 87 | 136 | 147 | |
| 148165r | | 124 | 128 | 138 | | 116 | 129 | 146 | |

TABLE 9-continued

| | 10 ng/ml LPS | | | | ng/ml LPS | | | |
|---|---|---|---|---|---|---|---|---|
| BP(nM): | 0 | 7.3 | 1.4 | 0.3 | 0 | 7.3 | 1.4 | 0.3 | 0 LPS |
| 148179r | | 85 | 139 | 134 | | 93 | 131 | 166 | | n = natural
r = recombinant

Normal anesthetized mice were challenged by the intranasal route with 10 ng/ml E. coli 0111:B4 LPS (results at Table 10). Twenty minutes before challenge, anesthetized mice were treated by the intranasal route with 50 μl saline, BPI protein or polymyxin B solution. At one hour after LPS challenge, mice were re-anesthetized, and 0.7 ml of saline containing 1% human serum albumin was added to the lungs via the trachea.

The lungs were gently kneaded. A 0.5 ml volume broncheoalveolar lavage (BAL) fluid was aspirated, cells were pelleted by centrifugation, and the BAL sample was stored at −70° C. The TNFα level in the BAL fluid was determined by measuring cytotoxicity towards WEHI clone 13 mouse fibrosarcoma cells. Human rTNFα (Chiron) was used as the standard.

TABLE 10

| Mouse | Saline Control | BPI 0.86 μg (15 pmol) | Polymyxin B 1.0 μg (782 pmol) |
|---|---|---|---|
| 1 | 1200 | 15 | 74 |
| 2 | 675 | 63 | 50 |
| 3 | 5560 | 425 | 132 |
| 4 | 2800 | 67 | 370 |
| 5 | 5250 | 1310 | 640 |
| Mean ± SD | 3097 ± 2250 | 376 ± 547 | 253 ± 251 |

TABLE 11

Amino Acid Composition of recombinant BPI 148179

| | recombinant | native |
|---|---|---|
| D + N | 27 | 38 |
| E + Q | 35 | 39 |
| S | 47 | 44 |
| G | 31 | 26 |
| H | 12 | 14 |
| R | 17 | 12 |
| T | 21 | 21 |
| A | 26 | 25 |
| P | 33 | 32 |
| Y | 16 | 14 |
| V | 33 | 37 |
| M | 10 | 15 |
| I | 26 | 26 |
| L | 50 | 47 |
| F | 25 | 25 |
| K | 42 | 36 |
| total | 451 | 451 |

(C,W not quantitated)

EXAMPLE 7

Expression of BPI Proteins and BPI-truncated Forms

A. Genetically Engineered Mammalian Cells Express BPI

In order to produce BPI protein and/or BPI protein variants in mammalian cells, the cDNA sequences must be inserted into a suitable plasmid vector. A suitable vector for such an application is pSV-1, which contains the origin of replication and early and late promoters of SV40, followed by multiple insert cloning sites, followed by the termination sequences from the hepatitis B surface antigen gene (FIG. 2). Also contained within the plasmid are an origin of bacterial DNA replication, and the genes encoding ampicillin resistance and dihydrofolate reductase. Similar vectors have been used to express other foreign genes (McGrogan, et al. Biotechnology 6, 172–177). Vector DNA was prepared for acceptance of BPI protein cDNA sequences by digestion with HindIII and Bam HI, and dephosphorylation with alkaline phosphatase.

Figure 24:
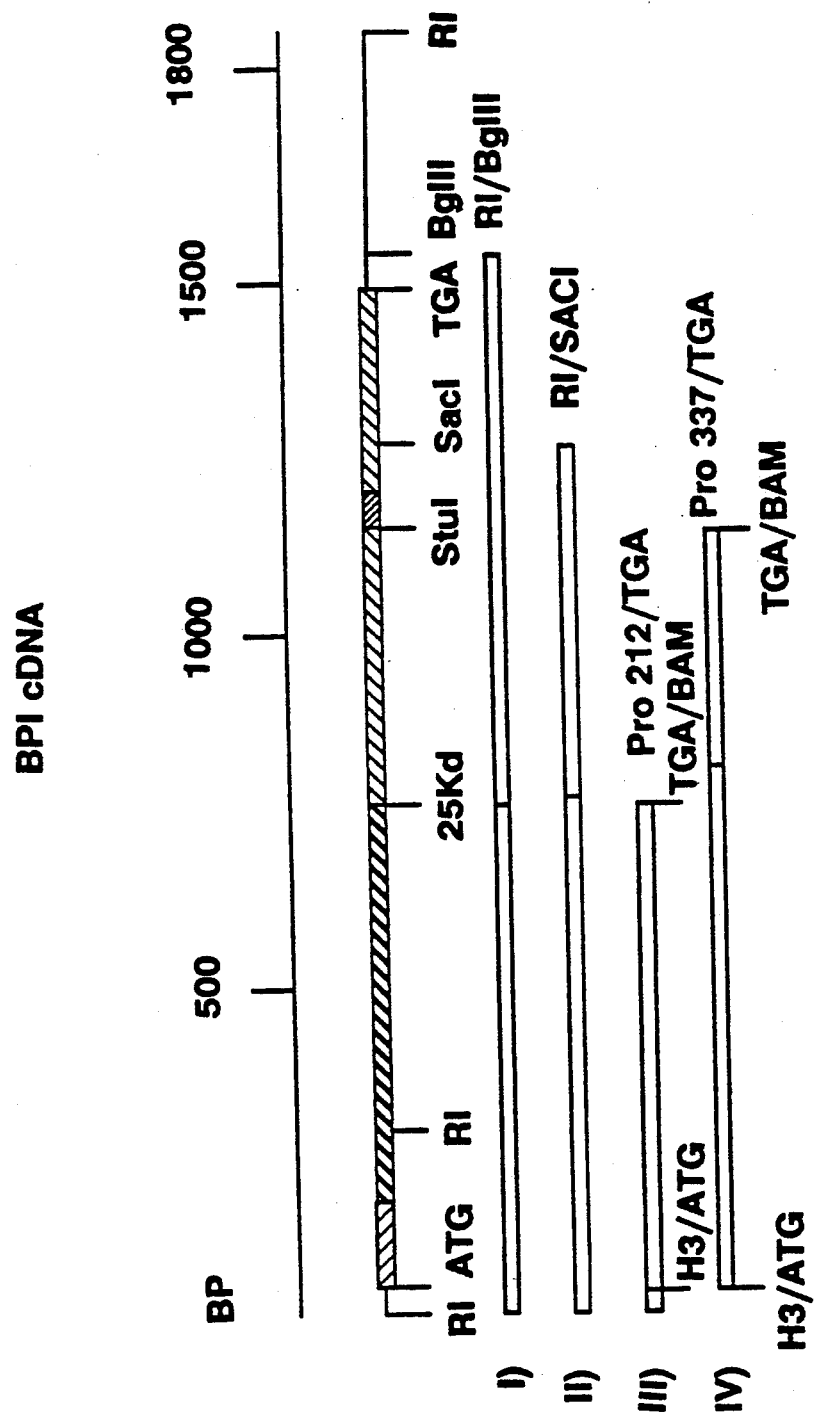

Several BPI protein cDNA-containing inserts were prepared for insertion into pSV-1. First, an insert encoding full-length BPI protein was prepared by digestion of the parent plasmid with appropriate restriction enzymes for ex. EcoRI and Bgl II, yielding two DNA fragments containing portions of the BPI protein coding sequence. These two fragments were ligated together into prepared SV-1, and the recombinant clones obtained were screened by restriction enzyme digestion for the presence of the two inserts in the proper orientation. Two cDNAs encoding truncated forms of BPI protein were generated using oligonucleotide-directed DNA amplification of the parent BPI protein insert DNA. The amplifying oligos were designed to replace codons 212 (oligo 459) (FIG. 25) and 337 (oligo 460) (FIG. 26) with stop codons, in addition to a BamHI cloning site (FIG. 24). At the 5'-e nd of both constructs, oligo 458 was used in the amplifications to create a HindIII site immediately upstream of the translational start codon ATG (FIG. 27). Thus, three BPI-encoding inserts were created, each encoding 55 kDa, 38 kDa, and 25 kDa forms of BPI, and each was ligated separately into prepared vector DNA.

Each of the three constructs was verified by restriction digest analysis, and then prepared in amounts sufficient for transfection into CHO cell line DUXB11 cells. Transfection was performed using lipofectin, and the resulting transformed cells were selected in the presence of increasing amounts of methotrexate using standard protocols (FIG. 22).

Supernatants from either transfected pools or clones derived from the pools were assayed for the presence of endotoxin binding activity by inhibition of TNr release. BPI was negligible in the vast majority of the selected cell lines. We found that only cell lines established from a 500 nM methotrexate bulk amplification produced commercially reasonable quantities of BPI. Two such cell lines are designated 3A1 and 4D6. It was unexpected that only the bulk amplification resulted in such cell lines.

B. Baculavirus Expression of rBPI in Insect Cells

Construction of plasmid expression vector: In order to produce BPI protein and/or BPI protein variants in insect cells, the cDNA sequence must first be inserted into a suitable plasmid expression vector, such as pAC373 (FIG. 29). Appropriate restriction sites for this insertion were created by standard site-directed mutagenesis procedures. The essential properties of a suitable expression vector include a transcriptional promoter such as the polyhedron gene promoter of pAC373, and flanking homologous sequences to direct recombination into the baculovirus genome. A polyadenylation signal, such as the one from the polyhedron gene present in this plasmid vector, may or may not be necessary for expression of the recombinant gene. A marker gene such as the beta-galactosidase gene of-E. coli, juxtaposed to regulatory sequences including a transcriptional promoter and possibly a polyadenylation signal, may be included in the vector but is not essential for BPI protein expression. A typical vector for such purposes pAC373, is shown in FIG. 29.

Creation of recombinant baculovirus: A chimeric baculovirus was created by homologous recombination between the expression plasmid containing the BPI protein target gene (or truncations thereof derived as described in Section A) and wild type baculovirus DNA. Plasmid and wild type baculovirus DNA were co-precipitated by the calcium phosphate technique and added to uninfected Spodoptera frugiperda (Sf9) insect cells. Four to seven days following transfection, cells exhibited a cytopathic morphology and contained the nuclear occlusion bodies typically produced by viral infection. The cell-free culture media containing both wild type and recombinant virus was harvested and assayed for BPI activity.

Identification and isolation of chimeric baculovirus: Clonal isolates of virus was obtained from this co-transfection stock by plaque purification on Sf9 cell monolayers overlaid with agarose. Candidate plaques for analysis will be identified by a plaque morphology negative for occlusion bodies. If the expression plasmid contains a marker gene such as beta galactosidase, recombinant plaques will be indicated by the blue color produced from a chromogenic substrate such as 5-bromo-4-chloryl-3-indolyl-β-D-galactopyranoside(X-gal) in the agarose plating medium. Picked plaques will be used for inoculation of cells in multiwell dishes. The resulting cell lysates and infected cell supernatants can be evaluated for expression of recombinant BPI, using standard activity or immunological assays. Positive wells may require additional rounds of plaque purification to obtain pure recombinant virus stocks free from wild type contamination.

Batch production of BPI: Sf9 cells are adapted to growth in serum-free, low protein medium such as Ex-Cell (J.R. Scientific). Cells are collected from suspension culture by gentle centrifugation and resuspended in fresh medium containing the viral inoculum at a concentration of ten million cells per ml, using a multiplicity of infection of one virus plaque forming unit per cell. After a period of two hours, the culture is diluted five fold with fresh medium and incubated two to three days. At the end of that time, the cells were pelleted by centrifugation and the conditioned medium was harvested. BPI protein was purified from the cell-free supernatant by standard means.

Characterization of insect cell derived BPI: BPI protein produced in insect cells using a baculovirus expression system is a glycosylated protein of approximate molecular weight of 55,000 kd. The N-terminal amino acid sequence is identical to that of mature mammalian cell BPI, indicating correct processing of the signal sequence. The specific activity of endotoxin binding of recombinant protein was indistinguishable from native BPI.

Construction of pT7BPI protein Plasmids: Oligonucleotides were prepared on an Applied Biosystems 380B DNA Synthesizer for use in oligonucleotide directed DNA amplification. The oligonucleotides created Nde I and BamHI restriction sites at the 5' and 3' ends, respectively, of the BPI protein DNA. In addition, another oligonucleotide containing a BamHI restriction site was used to create the truncated proline-212 version of the BPI protein DNA.

Following the amplification reactions, fragments were purified and digested with Nde I and BamHI. The plasmid, pGEMEX-1, (available from Promega) was selected as the vector for the constructions. pGEMEX-1 contains a T7 promoter which can be used for the expression of downstream sequences when placed into the proper host. The vector was cleaved with BamHI and, following purification, partially digested with Nde I to generate a vector with a single Nde I site and a single BamHI site. The fragments were ligated and transformed into the E. coli strain JM101 using the Hanahan transformation protocol (DNA Cloning Volume I, A Practical Approach, Edited by D. M. Glover, IRL Press). The transformed bacteria were plated on LB plates containing carbamicillin and incubated overnight at 37° C. Resistant colonies were selected and analyzed by preparing mini-plasmid preparations and digesting with the appropriate restriction enzymes. Digests were analyzed on both 1% agarose gels and 5% polyacrylamide gels.

The expression host, E. coli strain JM109(DE3), was transformed using 1 μl of the mini-plasmid preparation and the Hanahan transformation protocol. JM109(DE3) contains a chromosomal copy of the gene for T7 RNA polymerase which can be induced with IPTG. The transformed bacteria were plated on LB plates containing carbamicillin and incubated overnight at 37° C. Results are shown in FIG. 20.

Since the full-length and proline-212 truncated forms of BPI protein containing the signal peptide do not give colonies while those forms that do not contain the signal peptide do give colonies, the BPI protein was expressed in an active form and is processed correctly, sending the protein to the periplasmic space of the bacteria (the location in bacteria that proteins possessing a signal peptide are sent to) where the bactericidal activity kills the cell. This also implies that both the full-length form and the proline-212 truncated form are active and capable of bactericidal activity.

Whether the forms of BPI protein which do not contain the signal peptide are active or are prevented from exhibiting their bactericidal activity by being sequestered in the cell (either by the formation of inclusion bodies or by the inability to gain access to the plasma membrane due to the absence of the signal peptide or both) is not known.

Recombinant BPI produced in CHO cells binds LPS and that LPS binding can be inhibited by polymyxin B. Recombinant BPI also inhibits the release of TNF by human macrophages stimulated with LPS in vitro. Further, we show that BPI can be detected in the supernatants of FMLP/cytochalasin B treated neutrophils, and is also present on the surface of LPS, TNF or FMLP stimulated neutrophils. Degranulation and release of BPI by neutrophils at the site of infection may represent a feedback mechanism by which neutrophils negatively regulate LPS mediated induction of tumor necrosis factor. The exciting possibility that BPI may be a useful therapeutic agent to enhance the natural negative feedback mechanisms for regulating endotoxic shock is under investigation.

EXAMPLE 8

The pathophysiologic consequences of gram negative sepsis are primarily mediated by the release of bacterial endotoxin (LPS). Since BPI has LPS neutralizing activity in vitro, the effects of BPI in vivo were studied in experimental models of endotoxic shock.

Specifically, in one experiment one group of 8 rats (Sprague Dawley rats) was given a single, bolus injection of 1 mg BPI per kg body weight four hours before a single intravenous bolus of 0.5 mg/kg body weight 0111:B4 LPS obtained from Sigma. In the same experiment, a second group of 8 rats was given a single bolus injection of 1 mg BPI per kg body weight simultaneously with a single intravenous bolus of 0.5 mg/kg body weight 0111:B4 LPS. Further, a third group of 5 rats was given a single bolus injection of 1 mg BPI per kg body weight four hours after a single intravenous bolus of 0.5 mg/kg body weight 011:B4 LPS. Finally, a fourth group of 10 rats was treated with endotoxin alone. The rats were observed for 48 hours and the survival recorded for each group. The results of this experiment are shown in Table 12. Rats to which endotoxin alone was administered exhibited a mortality rate of 80%. Rats which received both BPI and endotoxin showed a significantly reduced mortality rate. The results set forth in Table 12 establish BPI is useful in vivo both to prevent and to treat disorders associated with the presence of endotoxin. High dose BPI toxicity studies revealed no evidence of toxicity when the animals were sacrificed at 7 days. We conclude BPI is a non-toxic naturally occurring protein which binds LPS, inhibits release of TNF and reduces mortality in both LPS and GNB experimental sepsis models (FIG. 36). We believe BPI offers a novel immunotherapeutic approach to the management of septic shock.

TABLE 12

INVESTIGATION OF THE POTENTIAL PROTECTIVE EFFICACY OF BPI IN THE RAT ENDOTOXIN CHALLENGE MODEL

| Endotoxin Dose Survival | BPI Dose | BPI Administration Regimen | % |
|---|---|---|---|
| 0.5 mg/kg (2/10) | — | — | 20 |
| 0.5 mg/kg (6/8) | 1 mg/kg | 4 hr pre-injection | 75 |
| 0.5 mg/kg (4/8) | 1 mg/kg | simultaneous | 50 |
| 0.5 mg/kg (4/5) | 1 mg/kg | 4 hr post-injection | 80 |

Additionally, in a second experiment with Bactericidal/Permeability Increasing Protein (BPI) neutropenic rats were challenged with Pseudomonas (PA1244) during a period of neutropenia. One group of rats was treated with 10mg BPI/kg of body weight by intravenous administration at the onset of fever at day 5 and observed through day 11. A second group of rats was treated at the onset of fever with buffer containing saline at day 5 and observed until day 11. After day 8, the rat group treated with buffer was found dead; however, the rat group treated with BPI exhibited 60% survival. The rats were observed for 11 days and the survival recorded for each group. At day 11, no additional deaths occurred for the rat group treated with BPI. The results of this experiment are shown in FIG. 34. FIG. 34 is a line graph showing that (1) during and after day 8 the rat group treated with buffer experienced a 100% mortality rate and (2) during and after day 7 the rat group treated with BPI exhibited about a 40% mortality rate. The rats which received BPI showed a significantly reduced mortality rate.

Human recombinant BPI at does up to 10 mg/kg intravenously (IV) produced no acute hexatologic, biochemical, or pathologic abnormalities in outbred CD-1 mice or Sprague-Dawley rats (Table 13). Infusion of 1 mg/kg of *E. coli* 0111:B4 LPS IV in 6 CD-1 mice resulted in a 100% (6/6) survival rate in control CD-1 mice. The survival rate in BPI treated mice infused with 1 mg/kg of *E. coli* 0111:B4 LPS IV at 1 mg/kg BPI IV, 2 mg/kg BPI IV, and 10 mg/kg BPI IV was 100% (4/4), 100% (4/4) and 100 (5/5), respectively.

Infusion of 10 mg/kg of *E. coli* 0111:B4 LPS IV in 6 CD-1 mice resulted in a 17% (1/6) survival rate in control CD-1 mice. The survival rate in BPI treated mice infused with 1 mg/kg of

TABLE 13

BPI PROTECTS AGAINST LETHALITY FROM ENDOTIXIC SHOCK (CD-1MICE)

| Endotoxin Challenge (E. Coli 0111:B4 | % SURVIVAL (NO. SURVIVORS/ TOTAL NO. ANIMALS TESTED) | | | |
|---|---|---|---|---|
| | Control (Saline) | BPI 1 mg/kgIV | BPI 2 mg/kgIV | BPI 10 mg/kgIV |
| * 1 mg/kg IV | 100 (6/6) | 100 (4/4) | 100 (4/4) | 100 (5/5) |
| * 10 mg/kg IV | 17 (1/6) | 50 (2/4) | 100 (4/4) | 100 (5/5) |
| * 50 mg/kg IV | 0 (0/6) | 25 (1/4) | 25 (1/4) | 100 (5/5) |
| * 100 mg/kg IV | 0 (0/6) | 0 (0/4) | 0 (0/4) | 80 (4/5) |
| *·200 mg/kg IV | 0 (0/6) | 0 (0/4) | 0 (0/4) | 20 (1/5) |

*E. coli* 0111:B4 LPS IV at 1 mg/kg BPI IV, 2 mg/kg BPI IV, and 10 mg/kg BPI IV was 50% (2/4), 100% (4/4) and 100 (5/5), respectively.

Infusion of 50 mg/kg of *E. coli* 0111:B4 LPS IV in 6 CD-1 mice resulted in a 0% (0/6) survival rate in control CD-1 mice. The survival rate in BPI treated mice infused with 1 mg/kg of *E. coli* 0111:B4 LPS IV at 1 mg/kg BPI IV, 2 mg/kg BPI IV, and 10 mg/kg BPI IV was 25% (1/4), 25% (1/4) and 25 (5/5), respectively.

Infusion of 100 mg/kg of *E. coli* 0111:B4 LPS IV in 6 CD-1 mice resulted in a 0% (0/6) survival rate in control CD-1 mice. The survival rate in BPI treated mice infused with 1 mg/kg of *E. coli* 0111:B4 LPS IV at 1 mg/kg BPI IV, 2 mg/kg BPI IV, and 10 mg/kg BPI IV was 0% (0/4), 0% (0/4) and 80% (4/5), respectively.

Infusion of 200 mg/kg of *E. coli* 0111:B4 LPS IV in 6 CD-1 mice resulted in a 0% (0/6) survival rate in control CD-1 mice. The survival rate in BPI treated mice infused with 1 mg/kg of *E. coli* 0111:B4 LPS IV at 1 mg/kg BPI IV, 2 mg/kg BPI IV, and 10 mg/kg BPI IV was 0% (0/4), 0% (0/4) and 20% (1/5), respectively.

In conclusion, Table 13 demonstrates that BPI is non-toxic in experimental animals and provides significant protection from lethality following endotoxin challenge (FIG. 35). This naturally occuring, neutrophil derived, antimicrobial protein provides a new therapeutic strategy in the treatment of septic shock.

Human recombinant BPI at does up to 10 mg/kg intravenously (IV) produced no acute hexatologic, biochemical, or pathologic abnormalities in outbred CD-1 mice (Table 14). Using CD-1 mice, the in vivo efficacy of BPI against LPS was tested by infusing 50 mg/kg of *E. coli* 0111:B4 LPS IV in 10 mice resulted in a 100% (0/10) survival rate in control CD-1 mice. The survival rate for BPI treated mice infused with 50 mg/kg of *E. coli* 0111:B4 LPS IV at 10 mg/kg BPI IV was 0%

(0/10). The p value is p<0.001. Further, 5 mice were infused with 50 mg/kg of 055 IV (as control) which resulted in a 0% (0/5) survival rate. The survival rate for BPI treated mice infused with of 50 mg/kg 055 IV at 10 mg/kg BPI IV was 100% (5/5). The p value is p<0.01. Additionally, 5 mice were infused with 25 mg/kg of Rc rough mutant (core glycolipid) IV (as control) which resulted in a 0% (0/5) survival rate. The survival rate for BPI treated mice infused with 25 mg/kg of Rc rough mutant (core glycolipid)IV at 10 mg/kg BPI IV was 100% (5/5). The p is p<0.01. Also, 4 mice were infused with 25 mg/kg of Lipid A IV (as control) which resulted in a 0% (0/4) survival rate. The survival rate for BPI treated mice infused with 25 mg/kg of Lipid A IV at 10 mg/kg BPI IV was 100% (5/5). The p value is p<0.05.

BPI is a non-toxic naturally occurring protein with LPS neutralizing activity which reduces mortality in both endotoxic and bacteremic models of sepsis syndrome and may be a useful immunotherapeutic approach to the management of the septic shock.

TABLE 14

EFFECT OF BPI ON LETHALITY OF VARIOUS LPS PHENOTYPES

| | % Survival (No. Surviving/No. Animals Tested) | | |
|---|---|---|---|
| LPS Phenotype | BPI 10 mg/kg | Control | p Value |
| * 0111:B4 50 mg/kg | 100 (10/10) | 0 (1/10) | p < 0.001 |
| * 055 50 mg/kg | 100 (5/5) | 0 (0/5) | P = 0.01 |
| * Rc Rough mutant (core glycolipid) 25 mg/kg | 100 (5/5) | 0 (0/5) | p = 0.01 |
| * Lipid A 25 mg/kg | 100 (5/5) | 0 (0/4) | p < 0.05 |

In order to generate a non-glycosylated form of the BPI molecule, the chinese hamster ovary (CHO) cell line which normally expresses glycosylated recombinant BPI (clone 3A1), was grown to confluence in roller bottles (Costar, Cambridge, Mass.) in REM 020 (Hazelton Inc. Denver, Pa.) containing 7.5% dialyzed bovine serum (Gibco)+2 μg/ml tunicamycin (Boehringer Mannheim, Indianapolis, Ind.). After 24 hours, the medium was discarded, and replaced with fresh complete medium containing 2 μ/ml tunicamycin. Conditioned medium was collected and replaced every 24 hours for three days. Non-glycosylated BPI was purified from conditioned medium using Superose 12 (Pharmacia) size exclusion chromatography run in 20 mM glycine+100 mM NaCl at pH 2. Fractions containing nonglycosylated BPI (identified by polyacrylamide gel electrophoresis) were pooled.

Non-glycosylated BPI was injected into mice at 10 mg/kg. Blood was collected at the indicated times through the retroorbital plexus. Blood samples were then allowed to clot, the fibrin clot was removed by centrifugation, and the BPI levels were determined by ELISA assay.

What is claimed is:

1. A method for preventing endotoxin-associated shock in a subject which comprises administering to the subject an amount of a BPI protein effective to bind to endotoxin so as to prevent endotoxin associated shock in the subject.

2. The method of claim 1, wherein the effective amount of the BPI protein is between about 0.1 and about 10 mg/kg body weight of subject.

3. The method of claim 2, wherein the effective amount is an amount between about 1 and about 10 mg/kg body weight of subject.

4. A method for treating a subject suffering from endotoxin-associated shock which comprises administering to the subject an amount of a BPI protein effective to bind endotoxin so as to treat the subject suffering from endotoxin-associated shock.

5. The method of claim 4, wherein the effective amount of the BPI protein is between about 0.1 and about 10 mg/kg body weight of subject.

6. The method of claim 5, wherein the effective amount is an amount between about 1 and about 10 mg/kg body weight of subject.

* * * * *